United States Patent
Li

(10) Patent No.: US 11,554,177 B2
(45) Date of Patent: Jan. 17, 2023

(54) ANTIBODY-DRUG CONJUGATES TARGETING HUMAN CLAUDIN 18.2

(71) Applicant: LaNova Medicines Limited Company, Shanghai (CN)

(72) Inventor: RunSheng Li, Shanghai (CN)

(73) Assignee: Lanova Medicines Limited Company, Shanghai (CN)

( * ) Notice: Subject to any disclaimer, the term of this patent is extended or adjusted under 35 U.S.C. 154(b) by 0 days.

(21) Appl. No.: 17/530,209

(22) Filed: Nov. 18, 2021

(65) Prior Publication Data

US 2022/0168437 A1 Jun. 2, 2022

Related U.S. Application Data

(63) Continuation of application No. PCT/CN2020/126780, filed on Nov. 5, 2020.

(30) Foreign Application Priority Data

Nov. 5, 2019 (WO) ................ PCT/CN2019/115760

(51) Int. Cl.
 *A61K 47/68* (2017.01)
 *A61P 35/00* (2006.01)

(52) U.S. Cl.
 CPC ...... *A61K 47/6849* (2017.08); *A61K 47/6817* (2017.08); *A61P 35/00* (2018.01)

(58) Field of Classification Search
 CPC .................. A61K 47/6817; A61K 47/6849
 See application file for complete search history.

(56) References Cited

U.S. PATENT DOCUMENTS

| | | | |
|---|---|---|---|
| 5,892,019 | A | 4/1999 | Schlom et al. |
| 6,150,584 | A | 11/2000 | Kucherlapati et al. |
| 6,420,140 | B1 | 7/2002 | Hori et al. |
| 6,458,592 | B1 | 10/2002 | Jakobovits et al. |
| 2019/0083645 | A1 | 3/2019 | Fong et al. |
| 2021/0024646 | A1 | 1/2021 | Yu et al. |

FOREIGN PATENT DOCUMENTS

| | | |
|---|---|---|
| EP | 2311877 A2 | 4/2011 |
| WO | 2013167153 A1 | 11/2013 |
| WO | 2016165762 A1 | 10/2016 |
| WO | 2016166122 A1 | 10/2016 |
| WO | 2018006882 A1 | 1/2018 |
| WO | 2019170147 A1 | 9/2019 |
| WO | 2019174617 A1 | 9/2019 |
| WO | 2019219089 A1 | 11/2019 |

OTHER PUBLICATIONS

International Search Report and Written Opinion for PCT/CN2020/126780 dated Jan. 27, 2021, 15 pages.
International Preliminary Report on Patentability received for PCT International Application No. PCT/CN2020/126780, dated May 19, 2022, 8 pages.
Chothia et al. (Aug. 20, 1987) "Canonical Structures for the Hypervariable Regions of Immunoglobulins", Journal of Molecular Biology, 196(4):901-917.
GENBANK (Jul. 31, 2022) "Claudin-18 isoform 2 [*Homo sapiens*]", Accession No. NP_001002026.1, 3 pages.
Hamers-Casterman et al. (Jun. 3, 1993) "Naturally Occurring Antibodies Devoid of Light Chains", Nature, 363(6428):446-448.
Roux et al. (Oct. 15, 1998) "Comparisons of the Ability of Human IgG3 Hinge Mutants, IgM, IgE, and IgA2, to Form Small Immune Complexes: A Role for Flexibility and Geometry", Journal of Immunology, 161(8):4083-4090.
Suzuki et al. (Jun. 2017) "Crystal Structures of Claudins: Insights into their Intermolecular Interactions", Annals of the New York Academy of Sciences, 1397(1):25-34.
Thorpe et al. (1982) "The Preparation and Cytotoxic Properties of Antibody-Toxin Conjugates", Immunological Reviews, 62:119-158.

*Primary Examiner* — Robert S Landsman
(74) *Attorney, Agent, or Firm* — Mintz, Levin, Cohn, Ferris, Glovsk

(57) ABSTRACT

Provided are antibody-drug conjugates containing a drug moiety attached to an antibody or fragment thereof having binding specificity to the wild-type human claudin 18.2 (CLDN18.2) protein. The antibody or the fragment thereof binds to the β3-β4 loop (residues 45-63 of SEQ ID NO: 30, NYQGLWRSCVRESSGFTEC) and the β5 strand (residues 169-172 of SEQ ID NO: 30, YTFG) of CLDN18.2.

22 Claims, 18 Drawing Sheets

Specification includes a Sequence Listing.

ANTIBODY-DRUG CONJUGATES TARGETING HUMAN CLAUDIN 18.2

CROSS REFERENCE TO RELATED APPLICATIONS

The present application is a continuation of International Application No. PCT/CN2020/126780, filed Nov. 5, 2020, which claims priority to PCT/CN2019/115760, filed Nov. 5, 2019, the contents of each of which is incorporated herein by reference in its entirety in the present disclosure.

SEQUENCE LISTING

This application contains a Sequence Listing which has been submitted electronically in ASCII format and is hereby incorporated by reference in its entirety. Said ASCII copy, created on Nov. 5, 2020, is named Sequence list.txt and is 146,900 bytes in size.

BACKGROUND

Claudins, such as claudin 18.2, are considered promising targets for cancer immunotherapy. Claudins are a family of proteins that form the important components of the tight cell junctions. They establish a paracellular barrier which controls the flow of molecules between the cells. The proteins have N-terminus and a C-terminus in the cytoplasm. Different claudins are expressed on different tissues, their altered function has linked to formation of cancers of respective tissues. Claudin-1 is expressed in colon cancer, claudin-18 is expressed in gastric cancer, and claudin-10 is expressed in hepatocellular carcinoma.

Claudin-18 has two isoforms, isoform 1 and isoform 2. Isoform 2 (Claudin 18.2 or CLDN18.2) is a highly selective cell lineage marker. Claudin 18.2's expression in normal tissues is strictly confined to differentiated epithelial cells of the gastric mucosa, but it was absent from the gastric stem cell zone. Claudin 18.2 was retained on malignant transformation and was expressed in a significant proportion of primary gastric cancers and its metastases. Frequently ectopic activation of claudin 18.2 was also found in pancreatic, esophageal, ovarian, and lung tumors. These data suggested that CLDN18.2 has highly restricted expression pattern in normal tissues, with frequent ectopic activation in a diversity of human cancers.

SUMMARY

Anti-claudin 18.2 antibodies are discovered herein that selectively bind to wild-type claudin 18.2 and a common mutant M149L, and do not bind to other claudin 18 isoforms, such as claudin 18.1. In a surprising and unexpected discovery, the present disclosure demonstrates that these antibodies are highly effective in inducing receptor-mediated antibody internalization, in particular when compared to IMAB362 (claudiximab), a lead anti-claudin 18.2 antibody under clinical development. Therefore, when conjugated to a drug moiety, these antibodies are capable of efficiently delivering the drug into target cells, such as cancer cells overexpressing the claudin 18.2 protein.

The greatly increased ability to induce receptor-mediated antibody internalization of the presently disclosed antibodies may be attributed to the way these antibodies bind to the claudin 18.2 protein. As demonstrated in Example 14 and illustrated in FIG. 20, amino acid residues on the claudin 18.2 protein that are important for the binding to the antibodies include those that are important for stabilizing the conformation of the extracellular loops (e.g., W30, L49, W50, C53, C63 and R80). More important, the residues that are involved in binding to the antibodies are contemplated to include N45, Y46, G48, V54, R55, E56, S58, F60, and E62, which are located between the β3 and β4 strands of the first extracellular loop, and Y169 and G172, which are in β5 of the second extracellular loop. By contrast, it is believed that known anti-claudin 18.2 antibodies only bind to one of the extracellular loops.

In accordance with one embodiment of the present disclosure, provided is an antibody-drug conjugate, comprising a drug moiety covalently attached to an antibody or fragment thereof having binding specificity to a wild-type human claudin 18.2 (CLDN18.2) protein, wherein the antibody or the fragment thereof binds to the β3-β4 loop and the β5 strand of CLDN18.2. The β3-β4 loop consists of residues 45-63 of SEQ ID NO:30 (NYQGLWRSCVRESSGFTEC), and the β5 strand consists of residues 169-172 of SEQ ID NO:30 (YTFG).

In some embodiments, the ratio of the number of drug moieties to the number of antibody or fragment is 1:1 to 20:1. In some embodiments, the ratio is 2:1 to 10:1. In some embodiments, the ratio is 2:1 to 6:1. In some embodiments, the ratio is about 2:1, 2.5:1, 3:1, 3.5:1, 4:1, 4.5:1 or 5:1.

In some embodiments, the antibody or the fragment thereof does not bind to β1 and β2, or binds to β1 or β2 at an affinity that is at least 10 fold lower than to the β3-β4 loop or the β5 strand. In some embodiments, the antibody or the fragment thereof does not bind to the CLDN18.1 protein or binds to CLDN18.1 at an affinity that is at least 10 fold lower than to CLDN18.2.

In some embodiments, the antibody or the fragment thereof binds to the CLDN18.2 M149L mutant at an affinity that is at least 1% of the affinity to the wild-type CLDN18.2 protein.

In some embodiments, the antibody or the fragment thereof binds to at least an amino acid residue selected from the group consisting of N45, Y46, G48, V54, R55, E56, S58, F60, and E62; and at least an amino acid residue selected from the group consisting of Y169 and G172, of SEQ ID NO:30.

The drug moiety may be a cytotoxic or cytostatic agent, an immunosuppressive agent, a radioisotope, a toxin, or the like. The drug moiety, once released in cancer cell, can inhibit the multiplication of the cancer cell, or causing apoptosis in the cancer cell. Examples of drug moieties are selected from the group consisting of DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl]amino]propyl]-1-pyrrolidinyl]-1-[(1S)-1-methylpropyl]-4-oxobutyl]-N-methyl-(9CI)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-(αR,βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino] phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1- pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives.

Methods and uses for the treatment of diseases and conditions are also provided. In one embodiment, provided is a method of treating cancer in a patient in need thereof, comprising administering to the patient the antibody-drug conjugate of the present disclosure.

DETAILED DESCRIPTION

Definitions

Figure 1:
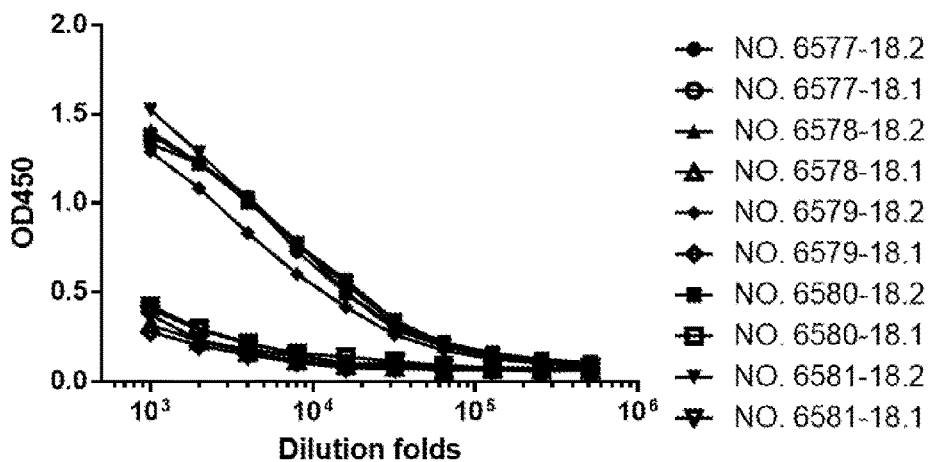
FIG. 1 shows that the mouse sera from all mice after DNA immunisation have high titration reacted with HEK293 cells transfected with CLD 18A2 by flow cytometry, CLD 18A1 as negative control.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., saltbridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\varepsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab)$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a $\beta$-sheet conformation and the CDRs form loops which connect, and in some cases form part of, the $\beta$-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.,* 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|         | Kabat  | Chothia |
|---------|--------|---------|
| CDR-H1  | 31-35  | 26-32   |
| CDR-H2  | 50-65  | 52-58   |
| CDR-H3  | 95-102 | 95-102  |
| CDR-L1  | 24-34  | 26-32   |
| CDR-L2  | 50-56  | 50-52   |
| CDR-L3  | 89-97  | 91-96   |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-Claudin 18.2 Antibodies and Fragments

The present disclosure provides anti-claudin 18.2 antibodies with high affinity to both the wild-type claudin 18.2 and a common mutant, M149L (the SU620 cell endogenously expressing this mutation). To the best knowledge of the inventors, all currently known anti-claudin 18.2 proteins do not bind to this mutant. The antibodies of the present disclosure, therefore, have the unique advantage of being capable of targeting both the wild-type and the M149L mutant claudin 18.2 protein. This advantage is important because a significant portion of cancer patients harbor this common mutation. It is also worth noting that the antibodies of the present disclosure do not bind to the other claudin 18 isoform, claudin 18.1 (or binds claudin 18.1 at a much lower affinity).

The antibodies and fragments of the present disclosure exhibited superior properties even when using a clinical candidate as a reference. 175D10 (IMAB362; claudiximab) is currently undergoing phase III clinical trials for treating gastric and gastroesophageal junction adenocarcinoma. The instant antibodies and fragment not only showed stronger binding activities, they also exhibited higher ADCC and ADCP activities under various different conditions, as compared to 175D10.

Also important, the present disclosure demonstrates that these antibodies are highly effective in inducing receptor-mediated antibody internalization, even when compared to IMAB362. The greatly increased ability to induce receptor-mediated antibody internalization of the presently disclosed antibodies, it is contemplated, can be attributed to how these antibodies bind to the claudin 18.2 protein. As demonstrated in Example 14 and illustrated in FIG. 20, amino acid residues on the claudin 18.2 protein that are important for the binding to the antibodies include those that are important for stabilizing the conformation of the extracellular loops (e.g., W30, L49, W50, C53, C63 and R80). W30, L49 and W50 are part of the W-LW-C-C consensus motif that helps to stabilize the conformation of loop 1. C53 and C63 form an inter-beta-strand disulfide bond. R80 is likely important for maintaining the interaction between parallel claudin 18.2 molecules on the cell surface, or for stabilizing the conformation of loop 1.

Also important for the antibody binding are residues N45, Y46, G48, V54, R55, E56, S58, F60, E62, Y169 and G172. Among them, N45, Y46, G48, V54, R55, E56, S58, F60 and E62 are located within the β3 strand, or through C63 in the β4 strand. This region, consisting of residues 45-63 of SEQ ID NO:30 (NYQGLWRSCVRESSGFTEC), is hereby referred to as the "β3 to β4 loop," which is part of the first extracellular loop (loop 1) of claudin 18.2. Y169 and G172, by contrast, are part of the β5 strand (residues 169-172 of SEQ ID NO:30; YTFG) of the second extracellular loop (loop 2).

The greatly increased activity by the presently disclosed antibodies to induce receptor-mediated antibody internalization, it is contemplated, is due to their ability to bind to residues in both the β3 to β4 loop and the β5 strand. In this context, it is believed that known anti-claudin 18.2 antibodies only bind to one of the loops.

The experimental data also show that the presently disclosed antibodies have higher binding specificity and improved ADCC and ADCP as compared to known ones.

Human Claudin 18.2 Sequence

2%, 3%, 5%, 10%, 15%, 20%, 25%, 30%, 35%, 40%, 45%, 50%, 60%, 70%, 80%, 90%, 95%, 98%, or 99% of the affinity to the wild-type CLDN18.2 protein.

In some embodiments, the antibodies or fragments thereof do not bind human CLDN18.1. In some embodiments, the antibodies or fragments thereof, as compared to binding to CLDN18.2, have a much weaker binding to human CLDN18.1, e.g., not greater than 10%, 5%, 2%, 1%, 0.5%, 0.1%, 0.05%, 0.01%, 0.005%, or 0.001%, without limitation.

Figure 4:
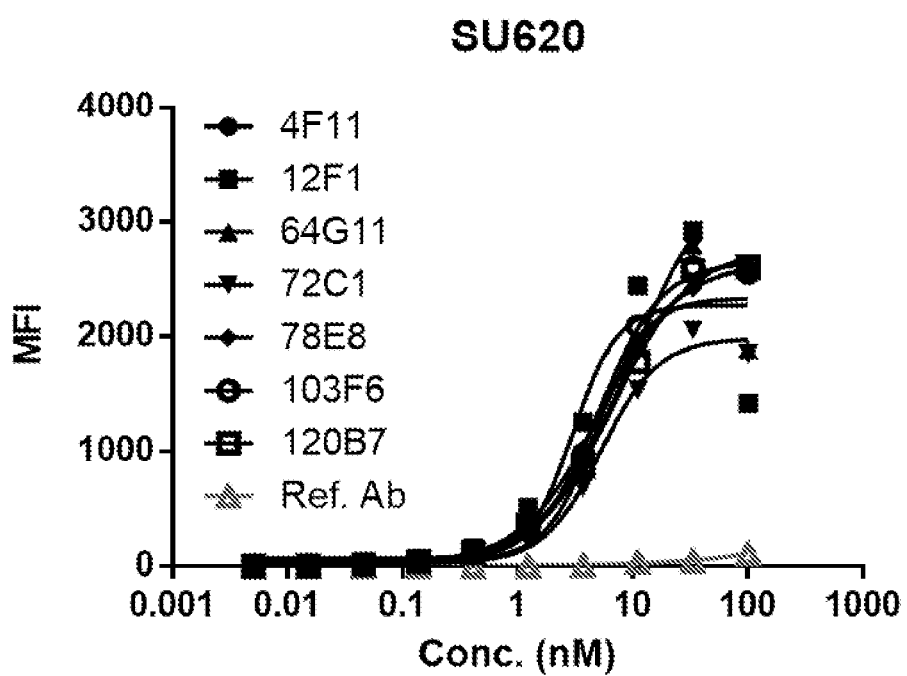
FIG. 4 shows that the purified murine antibodies can bind to SU620 cells endogenously expressing human CLD18A2 bearing M149L mutation by flow cytometry with high EC50, while the reference antibody did not.

As described above, the antibodies and fragments thereof of the present disclosure bind to the claudin 18.2 protein at an epitope that is different from known antibodies (see FIG. 4; at least the reference antibody interacts with M149 whereas the presently disclosed ones do not). In one embodiment, therefore, provided is an antibody or fragment thereof having binding specificity to a wild-type human claudin 18.2

| Name | Sequence (SEQ ID NO: 30) |
|---|---|
| Human Claudin 18.2 (NP_001002026) | 1 MAVTACQGLG FVVSLIGIAG IIAATCM<u>DQW</u> ST<u>Q</u>DLYNNPV TAVFNYQGLW |
| | 51 RSCVRESSGF TECRGYFTLL GLPAMLQAVR ALMIVGIVLG AIGLLVSIFA<br>        --------------<br>        β3-β4 loop |
| | 101 LKCIRIGSME DSAKANMTLT SGIMFIVSGL CAIAGVSVFA NMLVTNFWMS |
| | 151 TANMYTGMGG MVQTVQTR<u>Y</u>T F<u>G</u>AALFVGWV AGGLTLIGGV MMCIACRGLA<br>                     -- --<br>                      β5 |
| | 201 PEETNYKAVS YHASGHSVAY KPGGFKASTG FGSNTKNKKI YDGGARTEDE |
| | 251 VQSYPSKHDY V |

In accordance with one embodiment of the present disclosure, provided is an antibody or fragment thereof having binding specificity to a wild-type human claudin 18.2 (CLDN18.2) protein, wherein the antibody or the fragment thereof binds to both the first extracellular loop and the second extracellular loop of CLDN18.2. In some embodiments, the antibody or the fragment thereof binds to both the β3-β4 loop and the β5 strand of CLDN18.2.

In accordance with another embodiment of the present disclosure, provided is an antibody or fragment thereof having binding specificity to a wild-type human claudin 18.2 (CLDN18.2) protein, wherein the antibody or fragment further binds to a M149L mutant of the CLDN18.2 protein. In some embodiments, the antibody or fragment does not bind to a human wild-type claudin 18.1 (CLDN18.1) protein, or does not bind CLDN18.1 at an affinity that is greater than about 1% of the affinity to the wild-type CLDN18.2 protein.

The binding affinity of an antibody or fragment to a protein can be measured with many methods known in the art. For examples, it can be measured cell-free assays with standalone CLDN18.1 or CLDN18.2 proteins. Preferably, however, the measurement is done with the CLDN18.1 or CLDN18.2 protein on a cell surface mimicking the actual binding environment. Such binding assays are adequately exemplified in the experimental examples.

In some embodiments, the antibodies or fragments thereof have a binding affinity to the M149L mutant that is at least 1%, or alternatively at least 0.001%, 0.01%, 0.1%, 0.5%, (CLDN18.2) protein, wherein the binding between the antibody or fragment thereof and the wild-type CLDN18.2 protein involves amino acid residues comprising at least an amino acid residue selected from the group consisting of N45, Y46, G48, V54, R55, E56, S58, F60, and E62; and at least an amino acid residue selected from the group consisting of Y169 and G172, of the wild-type CLDN18.2 protein.

In some embodiments, the antibody or fragment thereof binds to N45 of CLDN18.2. In some embodiments, the antibody or fragment thereof binds to Y46 of CLDN18.2. In some embodiments, the antibody or fragment thereof binds to G48 of CLDN18.2. In some embodiments, the antibody or fragment thereof binds to L49 of CLDN18.2. In some embodiments, the antibody or fragment thereof binds to W50 of CLDN18.2. In some embodiments, the antibody or fragment thereof binds to C53 of CLDN18.2. In some embodiments, the antibody or fragment thereof binds to V54 of CLDN18.2. In some embodiments, the antibody or fragment thereof binds to R55 of CLDN18.2. In some embodiments, the antibody or fragment thereof binds to E56 of CLDN18.2. In some embodiments, the antibody or fragment thereof binds to E58 of CLDN18.2. In some embodiments, the antibody or fragment thereof binds to F60 of CLDN18.2. In some embodiments, the antibody or fragment thereof binds to E62 of CLDN18.2. In some embodiments, the antibody or fragment thereof binds to C63 of CLDN18.2.

In some embodiments, the antibody or fragment thereof binds to at least two amino acid residues selected from N45, Y46, G48, V54, R55, E56, S58, F60, and E62. In some embodiments, the antibody or fragment thereof binds to at least three amino acid residues selected from N45, Y46, G48, V54, R55, E56, S58, F60, and E62. In some embodiments, the antibody or fragment thereof binds to at least four amino acid residues selected from N45, Y46, G48, V54, R55, E56, S58, F60, and E62. In some embodiments, the antibody or fragment thereof binds to at least five amino acid residues selected from N45, Y46, G48, V54, R55, E56, S58, F60, and E62.

In some embodiments, the antibody or fragment thereof binds to at least Y169 of CLDN18.2. In some embodiments, the antibody or fragment thereof binds to at least G172 of CLDN18.2. In some embodiments, the antibody or fragment thereof binds to at least two amino acid residues selected from Y169 and G172 of CLDN18.2.

In some embodiments, the binding involves amino acid residues comprising W30; two, three, four, five or more amino acid residues selected from the group consisting of N45, Y46, G48, V54, R55, E56, S58, F60, and E62; and at least an amino acid residue selected from the group consisting of Y169 and G172, of the wild-type CLDN18.2 protein. In some embodiments, the binding involves amino acid residues comprising W30, N45, Y46, G48, V54, R55, E56, S58, F60, E62 and Y169 of the wild-type CLDN18.2 protein.

The weaker bindings to these amino acids on CLDN18.2 may be as compared to the other amino acids, such as G48, L49, W50, C53, V54, R55, E56. In some embodiments, the comparison is to the binding at the same amino acid to 175D10. For instance, the binding of the antibody or fragment of the present disclosure is weaker than that of 175D10 (IMGT/2Dstructure-DB card No: 10473) to at least one, two, three, four, five or all of D28, Q33, N38, V43, G59 and V79.

In some embodiments, the antibody or fragment thereof does not bind M149L of the CLDN18.2 protein. In some embodiments, the antibody or fragment thereof binds to a M149L mutant of the CLDN18.2 protein.

In accordance with one embodiment of the present disclosure, provided is an antibody or fragment thereof that includes the heavy chain and light chain variable domains with the CDR regions as shown in the CDR combinations of Table A.

TABLE A

| | | CDR combinations of tested antibodies (Kabat numbering) | | | | | |
|---|---|---|---|---|---|---|---|
| Comb No. | Antibody | CDRL1 (SEQ ID NO:) | CDRL2 (SEQ ID NO:) | CDRL3 (SEQ ID NO:) | CDRH1 (SEQ ID NO:) | CDRH2 (SEQ ID NO:) | CDRH3 (SEQ ID NO:) |
| 1 | 64G11B4 | KSSQSLLNSGNQRNYLT (208) | WASTRES (227) | QNDYFYPFT (42) | NYLLE (234) | EINPGNGGSNYNEKFKG (255) | IYYGNSFAY (281) |
| 2 | 65G8B8 | KSSQSLLNSGNLKNYLT (209) | WASTRES (227) | QNVYIYPFT (43) | SYGVS (235) | VIWGDGNTIYHSALKS (256) | QGLYGHAMDY (282) |
| 3 | 56E8F10F4 | KSSQSLLNSGNQKNYLT (210) | WASTRES (227) | QNDYYFPFT (44) | SFGMN (236) | FISGGSNTIHYLDTVKG (257) | LALGNAMDY (283) |
| 4 | 54A2C4 | KSSQSLLNGGNQKNYLA (211) | GASTRES (228) | QNDLYYPWT (45) | TNAMN (237) | RIRSKSNNYATYYADSVKD (258) | GAYYGNSKAFDY (284) |
| 5 | 54A2C4' | KSSQSLLNGGNQKNYLA (211) | GASTRES (228) | QNDLYYPWT (45) | NYLLE (234) | EINPGNGGSNYNEKFKG (255) | IYYGNSFAY (281) |
| 6 | 54A2C4" | KSSQSLLNGGNQKNYLA (211) | GASTRES (228) | QNDLYYPWT (45) | TYSIH (238) | YINPSTIYTNYNQKFKY (259) | EGYGRGNAMDY (285) |
| 7 | 44F6B11 | KSNQSLLNSGNQKKYLT (212) | WASTRES (227) | QNGYSYPFT (46) | NYGMS (239) | TFSYGDSHNYSDSVKG (260) | FGRGNTMDY (286) |

TABLE A-continued

CDR combinations of tested antibodies (Kabat numbering)

| Comb No. | Antibody | CDRL1 (SEQ ID NO:) | CDRL2 (SEQ ID NO:) | CDRL3 (SEQ ID NO:) | CDRH1 (SEQ ID NO:) | CDRH2 (SEQ ID NO:) | CDRH3 (SEQ ID NO:) |
|---|---|---|---|---|---|---|---|
| 8 | 15C2B7 | KSSQSLLNSGNQKNYLT (210) | WASTRES (227) | QNNYYFPLT (47) | NYGMN (240) | WINANTGEPTYAEEFKG (261) | LTRGNSFDY (287) |
| 9 | 20F1E10 | KSSQSLFNSGNQRNYLT (213) | WASTRES (227) | QNVYSYPLT (48) | KYGMN (241) | WISTNTGEPTYAEEFKG (262) | LVRGNSFDF (288) |
| 10 | 72C1B6A3 | KSSQSLLNSGNQKNYLT (210) | RASSRES (229) | QNDYIYPYT (8) | TYPIE (242) | NFHPYNDDTKYNEKFKG (263) | RAYGYPYAMDY (289) |
| 11 | 58G2C2 | KSSQSLLNSGNQKNYLT (210) | WAFTRES (230) | QNSYSYPFT (49) | NYLIE (243) | VINPGRSGTNYNEKFKG (264) | TRYGGNAMDY (290) |
| 12 | 101C4F12 | KSSQSLLNSGNQRNYLT (208) | WSSTRDS (231) | QNNFIYPLT (50) | SYGVH (244) | VIWAGGSTNYDSALMS (265) | SLYGNSLDS (291) |
| 13 | 103A10B2 | RSSMSLFNSGNQKSYLS (214) | WASTRDS (232) | HNDYIYPLT (51) | SFGVH (245) | VIWAGGSTNYNSALMS (266) | SLYGNSFDY (292) |
| 14 | 78E8G9G6 | RSIQSLLNSGNQKNYLS (215) | WASTRES (227) | QNSYSYPFT (49) | SYGVH (244) | VIWAGGRTNYNSALMS (267) | DRYGGNSLDY (293) |
| 15 | 4F11E2 | RSSQSLLNSGNRKNYLT (216) | WASTRES (227) | QNAYSYPFT (13) | TFGMH (246) | YITSGNSPIYFTDTVKG (268) | SSYYGNSMDY (294) |
| 16 | 10G7G11 | KSSQSLFNSGNQRNYLT (213) | WASTRES (227) | QNAYYFPFT (19) | TYGVH (247) | VMLSDGNTVYNSSLKS (269) | HKAYGNAMDY (295) |
| 17 | 12F1F4 | KSSQSLFNSGNQRNYLT (213) | WSSTRES (233) | QNNYYYPFT (52) | NYGVS (248) | VIWGDGNTNYQSALRS (270) | VGRGNAMDH (296) |
| 18 | 78C10B6G4 | KSSQSLLNSGNQKNYLT (210) | RASSRES (229) | QNDYIYPYT (8) | NYGVS (248) | VIRGDGNTNYQSALRS (271) | VGRGNAMDH (296) |
| 19 | 119G11D9 | RSTQSLFNSGNQKNYLT (217) | WASTRES (227) | QNAYYYPLT (53) | GFLMH (249) | YINPYNDGTKYSEKFKG (272) | LDYGNAMDY (297) |

TABLE A-continued

CDR combinations of tested antibodies (Kabat numbering)

| Comb No. | Antibody | CDRL1 (SEQ ID NO:) | CDRL2 (SEQ ID NO:) | CDRL3 (SEQ ID NO:) | CDRH1 (SEQ ID NO:) | CDRH2 (SEQ ID NO:) | CDRH3 (SEQ ID NO:) |
|---|---|---|---|---|---|---|---|
| 20 | 113G12E5E6 | KPSQSLLNSGNQKNYLA (218) | WASTRES (227) | QNAYFYPCT (54) | KYGVH (250) | VIWTGGNTDYNPALIP (273) | NGYYGNAMDY (298) |
| 21 | 116A8B7 | RSTQSLFNSGNQRNYLT (219) | WASTRES (227) | QNAYYYPLT (53) | GFLMH (249) | YINPYNDGTKYSEKFKG (272) | LDYGNAMDY (297) |
| 22 | 105F7G12 | KSSQSLLNSGNQKNYLA (220) | WASTRES (227) | QNAYFYPCT (54) | KYGVH (250) | VIWTGGNTDYNPALIP (273) | NGYYGNAMDY (298) |
| 23 | 84E9E12 | KSSQSVFNSGNQKNYLT (221) | WASTRES (227) | QNDYYFPLT (55) | SGYFW (251) | YISYDGSNNYNPSLKN (274) | FRFFAY (299) |
| 24 | 103F4D4 | RSSQSLLNGGNQKNYLT (222) | WASTRES (227) | QNAYFYPFT (56) | TYSIH (238) | YINPSTIYTNYNQKFKY (259) | EGYGRGNAMDY (285) |
| 25 | 110C12B6 | RSTQSLFNSGNQRNYLT (219) | WASTRES (227) | QNAYYYPLT (53) | GFLMH (249) | YINPYNDGTKYSEKFKG (272) | LDYGNAMDY (297) |
| 26 | 85H12E8 | KSSQSLLNSGNQRNYLS (223) | WASTRES (227) | QNAYFYPFT (56) | NYGVS (248) | VIWAGGNTNYNSALMS (275) | HGYGKGNAMDN (300) |
| 27 | 103H2B4 | KSSQSLLNSGNQKNYLT (210) | WASTRES (227) | QNNYFYPLT (57) | NFLTH (252) | EINPTNGRTYYNEKFKR (276) | IYYGNSMDY (301) |
| 28 | 103F6D3 | RSSQSLLNGGNQKNYLT (222) | WASTRES (227) | QNAYFYPFT (56) | TYSIH (238) | YINPNTIYTNYNQKFKY (277) | EGYGRGNAMDY (285) |
| 29 | 113E12F7 | KSSQSLFNSGNQKNYLT (224) | WASTRES (227) | QNNYIYPLA (58) | SYGVH (244) | VIWAGGSTNYDSALMS (265) | SLYGNSFDH (302) |
| 30 | 1206762 | KSSQSLLNSGNQKNYLT (210) | WASTRES (227) | QNGYYFPFT (3) | GYIIQ (253) | FINPYNDGTKYNEQFKG (278) | AYFGNSFAY (303) |
| 31 | 111812D11 | RSSQSLFNSGNQRNYLT (225) | WASTRES (227) | QNNYIYPLA (58) | SYGVH (244) | VIWAGGSTNYDSTLMS (279) | SLYGNSFDH (302) |

TABLE A-continued

CDR combinations of tested antibodies (Kabat numbering)

| Comb No. | Antibody | CDRL1 (SEQ ID NO:) | CDRL2 (SEQ ID NO:) | CDRL3 (SEQ ID NO:) | CDRH1 (SEQ ID NO:) | CDRH2 (SEQ ID NO:) | CDRH3 (SEQ ID NO:) |
|---|---|---|---|---|---|---|---|
| 32 | 111E7E2 | KSSQSLFNSGNQKNYLT (224) | WASTRES (227) | QNNYIYPLA (58) | SYGAH (254) | VIWAGSTNYDSALMS (265) | SLYGNSFDH (302) |
| 33 | 100F4G12 | KSTQSLLNSGNQRNYLT (226) | WASTRES (227) | QNAYYYPLT (53) | GFLMH (249) | YINPYNDGTKYSERFKG (280) | LDYGNAMDY (297) |

TABLE B

CDRs of 120B7B2 (Kabat numbering)

| CDR | Sequence (SEQ ID NO:) | De-Risked Versions (SEQ ID NO:) |
|---|---|---|
| CDRL1 | KSSQSLLNSGNQKNYLT (210) | KSSQSLLNAGNQKNYLT (304)<br>KSSQSLLESGNQKNYLT (305) |
| CDRL2 | WASTRES (227) | |
| CDRL3 | QNGYYFPFT (3) | QNAYYFPFT (19)<br>QEGYYFPFT (20) |
| CDRH1 | GYIIQ (253) | |
| CDRH2 | FINPYNDGTKYNEQFKG (278) | FINPYNDDTKYNEQFKG (306) |
| CDRH3 | AYFGNSFAY (303) | AYFGNAFAY (307) |

TABLE C

CDRs of 72C1B6A3 (Kabat numbering)

| CDR | Sequence (SEQ ID NO:) | De-Risked Versions (SEQ ID NO:) |
|---|---|---|
| CDRL1 | KSSQSLLNSGNQKNYLT (210) | KSSQSLLNAGNQKNYLT (304)<br>KSSQSLLESGNQKNYLT (305) |
| CDRL2 | RASSRES (229) | |
| CDRL3 | QNDYIYPYT (8) | |
| CDRH1 | TYPIE (242) | |
| CDRH2 | NFHPYNDDTKYNEKFKG (263) | |
| CDRH3 | RAYGYPYAMDY (289) | |

TABLE D

CDRs of 4F11E2 (Kabat numbering)

| CDR | Sequence (SEQ ID NO:) | De-Risked Versions (SEQ ID NO:) |
|---|---|---|
| CDRL1 | RSSQSLLNSGNRKNYLT (216) | RSSQSLLESGNRKNYLT (308)<br>RSSQSLLNAGNRKNYLT (309) |
| CDRL2 | WASTRES (227) | |
| CDRL3 | QNAYSYPFT (13) | |
| CDRH1 | TFGMH (246) | |
| CDRH2 | YITSGNSPIYFTDTVKG (268) | YITSGQSPIYFTDTVKG (310)<br>YITSGESPIYFTDTVKG (311) |
| CDRH3 | SSYYGNSMDY (294) | SSYYGgSMDY (312)<br>SSYYGESMDY (313)<br>SSYYGNAMDY (314) |

The antibodies that contained these CDR regions, whether mouse, humanized or chimeric, had potent claudin 18.2 binding and inhibitory activities. As shown in Examples 11 and 12, certain residues within the CDR can be modified to retain or improve the property or reduce their potential to have post-translational modifications (PTMs). Such modified CDR can be referred to as affinity matured or de-risked CDRs.

Non-limiting examples of de-risked CDRs are provided in Tables B-D, in the third columns. Affinity matured ones can include those having one, two or three amino acid addition, deletion and/or substitutions. In some embodiments, the substitutions can be conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE E

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE F

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |

TABLE F-continued

Conservative Amino Acid Substitutions

| For Amino Acid | Substitution With |
|---|---|
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |

TABLE F-continued

Conservative Amino Acid Substitutions

| For Amino Acid | Substitution With |
|---|---|
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |

TABLE F-continued

Conservative Amino Acid Substitutions

| For Amino Acid | Substitution With |
|---|---|
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In one embodiment, therefore, provided is an antibody or fragment thereof having binding specificity to a wild-type human claudin 18.2 (CLDN18.2) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein the CDRL1, CDRL2, CDRL3, CDRH1, CDRH2, and CDRH3 are selected from combinations 1-33 of Table A or each of the combinations 1-33 in which one or more of the CDRL1, CDRL2, CDRL3, CDRH1, CDRH2, and CDRH3 each includes one, two, or three amino acid addition, deletion, conservative amino acid substitution or the combinations thereof.

In some embodiments, an anti-CLDN18.2 antibody or fragment is provided that includes CDRL1, CDRL2, CDRL3, CDRH1, CDRH2, and CDRH3, each of which is selected from Table A or Tables B-D. For instance, provided is an antibody or fragment thereof having binding specificity to a wild-type human claudin 18.2 (CLDN18.2) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises an amino acid sequence selected from the group of SEQ ID NO:208-226, or comprises an amino acid sequence derived anyone of SEQ ID NO:208-226 by one, two, or three amino acid addition, deletion, amino acid substitution; the CDRL2 comprises an amino acid sequence selected from the group of SEQ ID NO:227-233, or comprises an amino acid sequence derived anyone of SEQ ID NO:227-233 by an amino acid addition, deletion, amino acid substitution; the CDRL3 comprises an amino acid sequence selected from the group of SEQ ID NO:3, 8, 13, 19 and 42-58, or comprises an amino acid sequence derived anyone of SEQ ID NO: 3, 8, 13, 19 and 42-58 by one, two, or three amino acid addition, deletion, amino acid substitution; the CDRH1 comprises an amino acid sequence selected from the group of SEQ ID NO:234-254, or comprises an amino acid sequence derived anyone of SEQ ID NO:234-254 by one, two, or three amino acid addition, deletion, amino acid substitution; the CDRH2 comprises an amino acid sequence selected from the group of SEQ ID NO:255-280, or comprises an amino acid sequence derived anyone of SEQ ID NO:255-280 by one, two, or three amino acid addition, deletion, amino acid substitution; and the CDRH3 comprises an amino acid sequence selected from the group of SEQ ID NO:281-303, or comprises an amino acid sequence derived anyone of SEQ ID NO:281-303 by one, two, or three amino acid addition, deletion, amino acid substitution.

In some embodiments, the CDRL1 comprises an amino acid sequence selected from the group of SEQ ID NO:208-226, 304-305 and 308-309; the CDRL2 comprises an amino acid sequence selected from the group of SEQ ID NO:227-233; the CDRL3 comprises an amino acid sequence selected from the group of SEQ ID NO:3, 8, 13, 19, 20 and 42-58; the CDRH1 comprises an amino acid sequence selected from the group of SEQ ID NO:234-254; the CDRH2 comprises an amino acid sequence selected from the group of SEQ ID NO:255-280, 306, 310 and 311; and the CDRH3 comprises an amino acid sequence selected from the group of SEQ ID NO:281-303, 307, and 312-314.

The antibody 120B7B2 has been demonstrated to be potent inhibitor of claudin 18.2. Its CDR sequences, along with a few de-risked versions, are provided in Table B. In one embodiment, the present disclosure provides an antibody or fragment thereof having binding specificity to a wild-type human claudin 18.2 (CLDN18.2) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises the amino acid sequence of QSLLNSGNQKNY (SEQ ID NO:1), QSLLNAGNQKNY (SEQ ID NO:17) or QSLLESGNQKNY (SEQ ID NO:18) or an amino acid sequence having one, two or three amino acid substitution from SEQ ID NO:1, 17 or 18, the CDRL2 comprises the amino acid sequence of WAS (SEQ ID NO:2) or an amino acid sequence having one or two amino acid substitution from SEQ ID NO:2, the CDRL3 comprises the amino acid sequence of CQNGYYFPFT (SEQ ID NO:3), QNAYYFPFT (SEQ ID NO:19) or QEGYYFPFT (SEQ ID NO:20) or an amino acid sequence having one, two or three amino acid substitution from SEQ ID NO:3, 19 or 20, the CDRH1 comprises the amino acid sequence of GYTFTGYI (SEQ ID NO:4) or an amino acid sequence having one, two or three amino acid substitution from SEQ ID NO:4, the CDRH2 comprises the amino acid sequence of INPYNDGT (SEQ ID NO:5) or INPYNDDT (SEQ ID NO:21) or an amino acid sequence having one, two or three amino acid substitution from SEQ ID NO:5 or 21, and the CDRH3 comprises the amino acid sequence of ARAYFGNSFAY (SEQ ID NO:6) or ARAYFGNAFAY (SEQ ID NO:22) or an amino acid sequence having one, two or three amino acid substitution from SEQ ID NO:6 or 22.

It is interesting to note (see Table A) that the CDRs from different antibody share great homology. It is then contemplated that each corresponding CDR can be interchanged without greatly impacting the antibody or fragment's binding affinity or activity. Alternatively, each particular amino acid in a CDR can be substituted with another amino acid present in a corresponding CDR from a different antibody.

In some embodiments, an antibody or fragment thereof is provided having binding specificity to a wild-type human claudin 18.2 (CLDN18.2) protein. In some embodiments, the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises the amino acid sequence of SEQ ID NO:210, 304 or 305 or an amino acid sequence having one, two or three amino acid substitution from SEQ ID NO:210, 304 or 305, the CDRL2 comprises the amino acid sequence of SEQ ID NO:227 or an amino acid sequence having one or two amino acid substitution from SEQ ID NO:227, the CDRL3 comprises the amino acid sequence of SEQ ID NO:3, 19 or 20 or an amino acid sequence having one, two or three amino acid substitution from SEQ ID NO:3, 19 or 20, the CDRH1 comprises the amino acid sequence of SEQ ID NO:253 or an amino acid sequence having one, two or three amino acid substitution from SEQ ID NO: 253, the CDRH2 comprises the amino acid sequence of SEQ ID NO:278 or 306 or an amino acid sequence having one, two or three amino acid substitution from SEQ ID NO:278 or 306, and the CDRH3 comprises the amino acid sequence of SEQ ID NO:303 or 307 or an amino acid sequence having one, two or three amino acid substitution from SEQ ID NO:303 or 307.

In some embodiments, the CDRL1 comprises the amino acid sequence of SEQ ID NO:210, 304 or 305, the CDRL2 comprises the amino acid sequence of SEQ ID NO:227, the CDRL3 comprises the amino acid sequence of SEQ ID NO:3, 19 or 20, the CDRH1 comprises the amino acid sequence of SEQ ID NO:253, the CDRH2 comprises the amino acid sequence of SEQ ID NO:278 or 306, and the CDRH3 comprises the amino acid sequence of SEQ ID NO:303 or 307.

Non-limiting examples of a light chain variable region includes an amino acid sequence selected from the group consisting of SEQ ID NO:141, 192-195 and 206-207, or a biological equivalent, such as a peptide having at least 90% sequence identity to an amino acid sequence selected from the group consisting of SEQ ID NO:141, 192-195 and 206-207.

Non-limiting examples of a heavy chain variable region include an amino acid sequence selected from the group consisting of SEQ ID NO:171, 188-191 and 205, or a biological equivalent, such as a peptide having at least 90% sequence identity to an amino acid sequence selected from the group consisting of SEQ ID NO:171, 188-191 and 205.

In some embodiments, the CDRL1 comprises the amino acid sequence of SEQ ID NO:304, the CDRL2 comprises the amino acid sequence of SEQ ID NO:227, the CDRL3 comprises the amino acid sequence of SEQ ID NO:19, the CDRH1 comprises the amino acid sequence of SEQ ID NO:253, the CDRH2 comprises the amino acid sequence of SEQ ID NO:306, and the CDRH3 comprises the amino acid sequence of SEQ ID NO:307. A non-limiting example of the antibody or fragment includes a light chain variable region comprising an amino acid sequence of SEQ ID NO:206 and a heavy chain variable region comprising an amino acid sequence of SEQ ID NO:205.

Likewise, 72C1B6A3 has been shown to be a good antibody. In another embodiment, therefore, provided is an antibody or fragment thereof having binding specificity to a wild-type human claudin 18.2 (CLDN18.2) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises the amino acid sequence of SEQ ID NO:210, 304 or 305 or an amino acid sequence having one, two or three amino acid substitution from SEQ ID NO:210, 304 or 305, the CDRL2 comprises the amino acid sequence of SEQ ID NO:229 or an amino acid sequence having one or two amino acid substitution from SEQ ID NO:229, the CDRL3 comprises the amino acid sequence of SEQ ID NO:8 or an amino acid sequence having one, two or three amino acid substitution from SEQ ID NO:8, the CDRH1 comprises the amino acid sequence of SEQ ID NO:242 or an amino acid sequence having one, two or three amino acid substitution from SEQ ID NO:242, the CDRH2 comprises the amino acid sequence of SEQ ID NO:263 or an amino acid sequence having one, two or three amino acid substitution from SEQ ID NO:263, and the CDRH3 comprises the amino acid sequence of SEQ ID NO:289 or an amino acid sequence having one, two or three amino acid substitution from SEQ ID NO:289.

In some embodiments, the CDRL1 comprises the amino acid sequence of SEQ ID NO:210, 304 or 305, the CDRL2 comprises the amino acid sequence of SEQ ID NO:229, the CDRL3 comprises the amino acid sequence of SEQ ID NO:8, the CDRH1 comprises the amino acid sequence of SEQ ID NO:242, the CDRH2 comprises the amino acid sequence of SEQ ID NO:263, and the CDRH3 comprises the amino acid sequence of SEQ ID NO:289.

Non-limiting examples of a light chain variable region include an amino acid sequence selected from the group consisting of SEQ ID NO:124, 185-187 and 203-204, or a biological equivalent, such as a peptide having at least 90% sequence identity to an amino acid sequence selected from the group consisting of SEQ ID NO:124, 185-187 and 203-204.

Non-limiting examples of a heavy chain variable region comprising an amino acid sequence selected from the group consisting of SEQ ID NO:153 and 181-184, or a biological equivalent, such as a peptide having at least 90% sequence identity to an amino acid sequence selected from the group consisting of SEQ ID NO:153 and 181-184.

In some embodiments, the CDRL1 comprises the amino acid sequence of SEQ ID NO:304, the CDRL2 comprises the amino acid sequence of SEQ ID NO:229, the CDRL3 comprises the amino acid sequence of SEQ ID NO:8, the CDRH1 comprises the amino acid sequence of SEQ ID NO:242, the CDRH2 comprises the amino acid sequence of SEQ ID NO:263, and the CDRH3 comprises the amino acid sequence of SEQ ID NO:289. A non-limiting example antibody or fragment thereof includes a light chain variable region comprising an amino acid sequence of SEQ ID NO:203 and a heavy chain variable region comprising an amino acid sequence of SEQ ID NO:181.

Also, 4F11E2 has been shown to be a good antibody. In another embodiment, therefore, provided is an antibody or fragment thereof having binding specificity to a wild-type human claudin 18.2 (CLDN18.2) protein, wherein the antibody or fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, and wherein: the CDRL1 comprises the amino acid sequence of SEQ ID NO:216, 308 or 309 or an amino acid sequence having one, two or three amino acid substitution from SEQ ID NO:216, 308 or 309, the CDRL2 comprises the amino acid sequence of SEQ ID NO:227 or an amino acid sequence having one or two amino acid substitution from SEQ ID NO:227, the CDRL3 comprises the amino acid sequence of SEQ ID NO:13 or an amino acid sequence having one, two or three amino acid substitution from SEQ ID NO:13, the CDRH1 comprises the amino acid sequence of SEQ ID NO:246 or an amino acid sequence having one, two or three amino acid substitution from SEQ ID NO:246, the CDRH2 comprises the amino acid sequence of SEQ ID NO:268, 310 or 311 or an amino acid sequence having one, two or three amino acid substitution from SEQ ID NO:268, 310 or 311, and the CDRH3 comprises the amino acid sequence of SEQ ID NO:294, 312, 313 or 314, or an amino acid sequence having one, two or three amino acid substitution from SEQ ID NO:294, 312, 313 or 314.

In some embodiments, the CDRL1 comprises the amino acid sequence of SEQ ID NO:216, 308 or 309, the CDRL2 comprises the amino acid sequence of SEQ ID NO:227, the CDRL3 comprises the amino acid sequence of SEQ ID NO:13, the CDRH1 comprises the amino acid sequence of SEQ ID NO:246, the CDRH2 comprises the amino acid sequence of SEQ ID NO:268, 310 or 311, and the CDRH3 comprises the amino acid sequence of SEQ ID NO:294, 312, 313 or 314.

Non-limiting examples of a light chain variable region include an amino acid sequence selected from the group consisting of SEQ ID NO:129, 178-180 and 201-202, or a biological equivalent, such as a peptide having at least 90% sequence identity to an amino acid sequence selected from the group consisting of SEQ ID NO:129, 178-180 and 201-202.

Non-limiting examples of a heavy chain variable region comprising an amino acid sequence selected from the group consisting of SEQ ID NO:159, 175-177 and 196-200, or a biological equivalents, such as a peptide having at least 90% sequence identity to an amino acid sequence selected from the group consisting of SEQ ID NO:159, 175-177 and 196-200.

In some embodiments, the CDRL1 comprises the amino acid sequence of SEQ ID NO:309, the CDRL2 comprises the amino acid sequence of SEQ ID NO:227, the CDRL3 comprises the amino acid sequence of SEQ ID NO:13, the CDRH1 comprises the amino acid sequence of SEQ ID NO:246, the CDRH2 comprises the amino acid sequence of SEQ ID NO:311, and the CDRH3 comprises the amino acid sequence of SEQ ID NO:294. A non-limiting example of the antibody or fragment includes a light chain variable region comprising an amino acid sequence of SEQ ID NO:202 and a heavy chain variable region comprising an amino acid sequence of SEQ ID NO:197.

In some embodiments, the antibodies are humanized antibodies. Humanized antibodies, as shown in Example 9, can include one or more back mutations to the mouse counterpart. Examples of such back mutations are shown in Table 3. In some embodiments, the antibody or fragment can include one, two, three, four, five or more of the back mutations.

In some embodiments, the anti-claudin 18.2 antibody of the present disclosure includes a VL of any one of SEQ ID NO: 117-144, 178-180, 185-187, 192-195, 201-202, 203-204 or 206-207, and a VH of any one of SEQ ID NO: 145-174, 175-177, 181-184, 188-191, 196-200, or 205 or their respective biological equivalents. A biological equivalent of a VH or VL is a sequence that includes the designated amino acids while having an overall 80%, 85%, 90%, 95%, 98% or 99% sequence identity. A biological equivalent of SEQ ID NO:145, therefore, can be a VH that has an overall 80%, 85%, 90%, 95%, 98% or 99% sequence identity to SEQ ID NO:145 but retains the CDRs, and optionally retains one or more, or all of the back-mutations.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

Antibody-Drug Conjugates

In some embodiments, the antibodies or fragments may be conjugated to therapeutic agents, prodrugs, peptides, proteins, enzymes, viruses, lipids, biological response modifiers, pharmaceutical agents, or PEG.

In one embodiment, the antibodies or fragments of the disclosure are covalently attached to a drug moiety. The drug moiety may be, or be modified to include, a group reactive with a conjugation point on the antibody. For example, a drug moiety can be attached by alkylation (e.g., at the epsilon-amino group lysines or the N-terminus of antibodies), reductive amination of oxidized carbohydrate, transesterification between hydroxyl and carboxyl groups, amidation at amino groups or carboxyl groups, and conjugation to thiols.

In some embodiments, the number of drug moieties, p, conjugated per antibody molecule ranges from an average of 1 to 8; 1 to 7, 1 to 6, 1 to 5, 1 to 4, 1 to 3, or 1 to 2. In some embodiments, p ranges from an average of 2 to 8, 2 to 7, 2 to 6, 2 to 5, 2 to 4 or 2 to 3. In other embodiments, p is an average of 1, 2, 3, 4, 5, 6, 7 or 8. In some embodiments, p ranges from an average of about 1 to about 20, about 1 to about 10, about 2 to about 10, about 2 to about 9, about 1 to about 8, about 1 to about 7, about 1 to about 6, about 1 to about 5, about 1 to about 4, about 1 to about 3, or about 1 to about 2. In some embodiments, p ranges from about 2 to about 8, about 2 to about 7, about 2 to about 6, about 2 to about 5, about 2 to about 4 or about 2 to about 3.

For example, when chemical activation of the protein results in formation of free thiol groups, the protein may be conjugated with a sulfhydryl reactive agent. In one aspect, the agent is one which is substantially specific for free thiol groups. Such agents include, for example, malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio.

The drug can be linked to the antibody or fragment by a linker. Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-4-[N-maleimidomethyl]cyclohexane-1-carboxylate (smcc). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (mc). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

A linker can include a group for linkage to the antibody. For example, linker can include an amino, hydroxyl, carboxyl or sulfhydryl reactive groups (e.g., malemide, haloacetamides (e.g., iodo, bromo or chloro), haloesters (e.g., iodo, bromo or chloro), halomethyl ketones (e.g., iodo, bromo or chloro), benzylic halides (e.g., iodide, bromide or chloride), vinyl sulfone and pyridylthio).

In some embodiments, the drug moiety is a cytotoxic or cytostatic agent, an immunosuppressive agent, a radioisotope, a toxin, or the like. The conjugate can be used for inhibiting the multiplication of a tumor cell or cancer cell, causing apoptosis in a tumor or cancer cell, or for treating cancer in a patient. The conjugate can be used accordingly in a variety of settings for the treatment of animal cancers. The conjugate can be used to deliver a drug to a tumor cell or cancer cell. Without being bound by theory, in some embodiments, the conjugate binds to or associates with a cancer cell expressing claudin 18.2, and the conjugate and/or drug can be taken up inside a tumor cell or cancer cell through receptor-mediated endocytosis.

Once inside the cell, one or more specific peptide sequences within the conjugate (e.g., in a linker) are hydrolytically cleaved by one or more tumor-cell or cancer-cell-associated proteases, resulting in release of the drug. The released drug is then free to migrate within the cell and induce cytotoxic or cytostatic or other activities. In some embodiments, the drug is cleaved from the antibody outside the tumor cell or cancer cell, and the drug subsequently penetrates the cell, or acts at the cell surface.

Examples of drug moieties or payloads are selected from the group consisting of DM1 (maytansine, N2'-deacetyl-N2'-(3-mercapto-1-oxopropyl)- or N2'-deacetyl-N2'-(3-mercapto-1-oxopropyl)-maytansine), mc-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl]amino]propyl]-1-pyr rolidinyl]-1-[(1S)-1-methylpropyl]-4-oxobutyl]-N-methyl-(9Cl)-L-valinamide), mc-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-(αR,βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino]phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives. In some embodiments, the drug moiety is selected from the group consisting of mc-MMAF and mc-Val-Cit-PABA-MMAE. In some embodiments, the drug moiety is a maytansinoid or an auristatin.

The antibodies or fragments may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylentriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants, derivatives or antibody-drug conjugates of the present disclosure may be used in certain treatment and diagnostic methods.

The present disclosure is further directed to antibody-based therapies which involve administering the antibodies, fragments, or antibody-drug conjugates of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. As provided above, claudin 18.2 can be overexpressed in tumor cells, in particular gastric, pancreatic, esophageal, ovarian, and lung tumors. Inhibition of claudin 18.2 has been shown to be useful for treating the tumors.

Accordingly, in some embodiments, provided are methods for treating a cancer in a patient in need thereof. The method, in one embodiment, entails administering to the patient an effective amount of an antibody, fragment, or antibody-drug conjugate of the present disclosure. In some embodiments, at least one of the cancer cells (e.g., stromal cells) in the patient over-express claudin 18.2.

Cellular therapies, such as chimeric antigen receptor (CAR) T-cell therapies, are also provided in the present disclosure. A suitable cell can be used, that is put in contact with an anti-claudin 18.2 antibody of the present disclosure (or alternatively engineered to express an anti-claudin 18.2 antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is one or more of gastric, pancreatic, esophageal, ovarian, and lung cancers.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, fragments, or antibody-drug conjugates or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as silastic membranes, or fibers. Preferably, when administering a protein, including an antibody, of the disclosure, care must be taken to use materials to which the protein does not absorb.

The amount of the antibodies, fragments, or antibody-drug conjugates of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antibodies, fragments, or antibody-drug conjugates of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Compositions

The present disclosure also provides pharmaceutical compositions. Such compositions comprise an effective amount of an antibody, fragment, or antibody-drug conjugate, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Murine Monoclonal Antibodies Against Human Claudin 18 Isoform 2 (CLD 18A2)

a. Immunizations:

Balb/c and C57/BL6 mice were immunized with eukaryotic expression vectors, encoding human claudin 18.2 (CLD 18A2) fragments. 50 µg of plasmid DNA was injected into the quadriceps (intramuscular, i.m.) on day 1 and 10. The presence of antibodies directed against human CLD 18A2 in the serum of the mice was monitored on day 20 by flow cytometry, using HEK293 cells transiently transfected with a nucleic acid encoding human CLD 18A2. Mice with detectable immune responses (FIG. 1) were boosted three and two days prior to fusion by intraperitoneal injection of $5 \times 10^7$ HEK293 cells transiently transfected with a nucleic acid encoding human CLD 18A2.

b. Generation of Hybridomas Producing Human Monoclonal Antibodies to CLD18A2:

Mouse splenocytes were isolated and fused with PEG to a mouse myeloma cell line based on standard protocols. The resulting hybridomas were then screened for production of immunoglobulins with CLD 18A2 specificity using HEK293 cells transfected with a nucleic acid encoding human CLD18 by cell ELISA.

Figure 2:
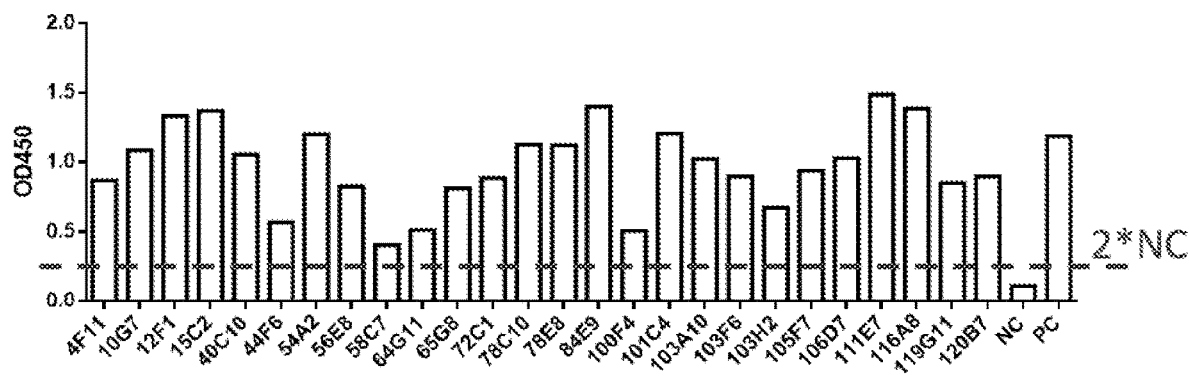
FIG. 2 shows that the hybridoma supernatants can bind to HEK293 cells transfected with human CLD18A2 by cell ELISA or flow cytometry.
Figure 2:
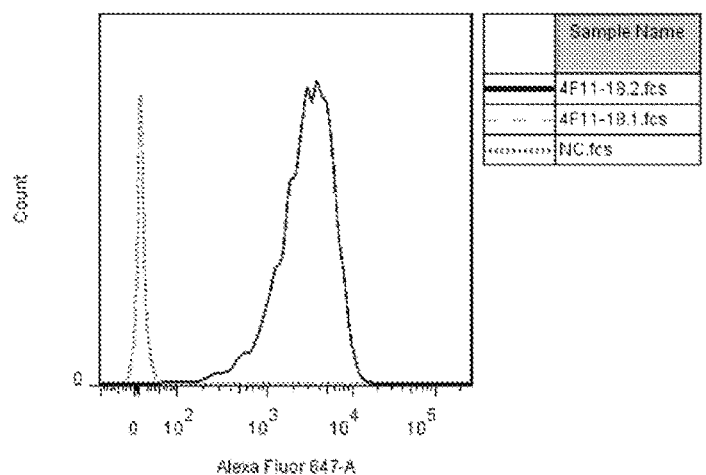

Single cell suspensions of splenic lymphocytes from immunized mice were fused with P3X63Ag8U.1 non-secreting mouse myeloma cells (ATCC, CRL 1597) in a 2:1 ratio using 50% PEG (Roche Diagnostics, CRL 738641). Cells were plated at approximately $3 \times 10^4$/well in flat bottom microtiter plates, followed by about two weeks incubation in selective medium containing 10% fetal bovine serum, 2% hybridoma fusion and cloning supplement (HFCS, Roche Diagnostics, CRL 1 363 735) plus 10 mM HEPES, 0.055 mM 2-mercaptoethanol, 50 µg/ml gentamycin and 1×HAT (Sigma, CRL H0262). After 10 to 14 days individual wells were screened by Cell ELISA for anti-CLD 18A2 monoclonal antibodies (FIG. 2). The antibody secreting hybridomas were re-plated, screened again with HEK293 expressing CLD 18A2 or CLD 18A1 by FACS and, if still positive for CLD18A2 and negative for CLD18A1, were subcloned by limiting dilution. The stable subclones were then cultured in vitro to generate small amounts of antibody in tissue culture medium for characterization. At least one clone from each hybridoma, which retained the reactivity of parent cells (by FACS), was chosen. Three vial cell banks were generated for each clone and stored in liquid nitrogen.

c. Selection of Monoclonal Antibodies Binding to CLD 18A2 not to CLD18A1:

To determine the isotype of antibodies, an isotype ELISA was performed. The mouse monoAB ID Kit (Zymed, CRL 90-6550) was used to determine Ig subclasses of the identified CLD18A2 reactive monoclonal antibodies. Thirty-two hybridoma cell lines were generated: 64G11B4, 65G8B8, 56E8F10F4, 54A2C4, 44F6B11, 15C2B7, 20F1E10, 72C1B6A3, 58G2C2, 101C4F12, 103A10B2, 40C10E3, 78E8G9G6, 4F11E2, 10G7G11, 12F1F4, 78C10B6G4, 119G11D9, 113G12E5E6, 116A8B7, 105F7G12, 84E9E12, 103F4D4, 110C12B6, 85H12E8, 103H2B4, 103F6D3, 113E12F7, 120B7B2, 111B12D11, 111E7E2, and 100F4G12, with further details as shown below:

64G11B4, mouse monoclonal IgG1, κ antibody
65G8B8, mouse monoclonal IgG1, κ antibody
56E8F10F4, mouse monoclonal IgG1, κ antibody
54A2C4, mouse monoclonal IgG1, κ antibody
44F6B11, mouse monoclonal IgG1, κ antibody
15C2B7, mouse monoclonal IgG1, κ antibody
20F1E10, mouse monoclonal IgG1, κ antibody
72C1B6A3, mouse monoclonal IgG1, κ antibody
58G2C2, mouse monoclonal IgG2a, κ antibody
101C4F12, mouse monoclonal IgG2b, κ antibody
103A10B2, mouse monoclonal IgG2b, κ antibody
40C10E3, mouse monoclonal IgG1, λ antibody
78E8G9G6, mouse monoclonal IgG1, κ antibody
4F11E2, mouse monoclonal IgG1, κ antibody
10G7G11, mouse monoclonal IgG1, κ antibody
12F1F4, mouse monoclonal IgG1, κ antibody
78C10B6G4, mouse monoclonal IgG1, κ antibody
119G11D9, mouse monoclonal IgG1, κ antibody
113G12E5E6, mouse monoclonal IgG1, κ antibody
116A8B7, mouse monoclonal IgG1, κ antibody
105F7G12, mouse monoclonal IgG1, κ antibody
84E9E12, mouse monoclonal IgG1, κ antibody
103F4D4, mouse monoclonal IgG1, κ antibody
110C12B6, mouse monoclonal IgG1, κ antibody
85H12E8, mouse monoclonal IgG1, κ antibody
103H2B4, mouse monoclonal IgG1, κ antibody
103F6D3, mouse monoclonal IgG1, κ antibody
113E12F7, mouse monoclonal IgG2a, κ antibody
120B7B2, mouse monoclonal IgG2a, κ antibody
111B12D11, mouse monoclonal IgG2a, κ antibody
111E7E2, mouse monoclonal IgG2a, κ antibody
100F4G12, mouse monoclonal IgG3, κ antibody.

Example 2. Hybridoma Sequencing

Hybridoma cells ($1 \times 10^7$) were harvested and total RNA was extracted using Tri Reagent as described above for spleen tissue. cDNA was prepared using SuperScript III kit according to the manufacturer's instruction, described above. The resulting cDNA product was used as template for PCR with primers VhRevU and VhForU, the resulting 300 bp PCR product was cleaned up using a PCR clean-up kit and sequenced with the same primer. PCR reaction was also performed with light chain V-region specific primer VkRev7 and VkFor (for variable region only) or KappaFor primers (for entire kappa light chain). Sequencing reactions were performed on cleaned PCR product to obtain DNA sequences for the antibodies, 64G11B4, 65G8B8, 56E8F10F4, 54A2C4, 44F6B11, 15C2B7, 20F1E10, 72C1B6A3, 58G2C2, 101C4F12, 103A10B2, 40C10E3, 78E8G9G6, 4F11E2, 10G7G11, 12F1F4, 78C10B6G4, 119G11D9, 113G12E5E6, 116A8B7, 105F7G12, 84E9E12, 103F4D4, 110C12B6, 85H12E8, 103H2B4, 103F6D3, 113E12F7, 120B7B2, 111B12D11, 111E7E2, and 100F4G12. Their variable (VH and VL) sequences are shown in Table 1 below.

TABLE 1

Sequences of the variable regions of the antibodies

| Antibody chain | Sequence | SEQ ID NO: |
|---|---|---|
| Light chains | | |
| 64G11B4 | DIVMTQSPSSLTVTAGEKVTMNCKS SQSLLNSGNQRNYLTWYQQKPGQPP KLLIYWASTRESGVPDRFTGSGSGT DFTLTISSVQADDLAVYYCQNDYFY PFTFGAGTNLELK | 117 |
| 65G8B8 | DIMMTQSPSSLTVTTGEKVTLTCKS SQSLLNSGNLKNYLTWYQQKPGHPP KLLIYWASTRESGVPVRFTGSGSGT DFTLTISSVQAEDLTVYYCQNVYIY PFTFGSGTKLEMR | 118 |
| 56E8F10F4 | DIVMTQSPSSLTVTAGEKVTMSCKS SQSLLNSGNQKNYLTWYQQKPGQPP KLLIYWASTRESGVPDRFTGSGSGT YFTLTISSVQADLAVYYCQNDYYF PFTFGSGTKLEIK | 119 |
| 54A2C4 | DTVMTQFPSSLSVSAGEKVTMSCKS SQSLLNGGNQKNYLAWYQQKPGQPP KLLIYGASTRESGVPDRFTGSGSGT DFTLTISSVQAEDLAVYYCQNDLYY PWTFGGGTKLEFK | 120 |
| 44F6B11 | DIVMTQSPSSLTVTAGEKVTIMSCKS NQSLLNSGNQKKYLTWYQQKPGQSP KLLIYWASTRESGVPDRFTGSESGT DFTLTISSVRAEDLAVYYCQNGYSY PFTFGSGTKLEMK | 121 |
| 15C2B7 | DIVMTQSPSSLTVTAGGKVTVSCKS SQSLLNSGNQKNYLTWYQQKPGQPP KLLIYWASTRESGVPDRFTGSGSGT DFTLTISSVQTEDLAVYYCQNNYYF PLTFGAGTKLELK | 122 |
| 20F1E10 | DIVMTQSPSSLTVTAGEKVTMSCKS SQSLFNSGNQRNYLTWYQQKPGQPP KLLIYWASTRESGVPDRFTGSGSGT DFILTITKVQAEDLAVYYCQNVYSY PLTFGAGTKLELK | 123 |
| 72C1B6A3 | DIVMTQSPSSLTVTAGEKVTMSCKS SQSLLNSGNQKNYLTWYQQRPGQPP KLLIYRASSRESGVPVRFTGSGSGT DFTLTISSVQAEDLAVYYCQNDYIY PYTFGGGTKLEMN | 124 |
| 58G2C2 | DIVMTQSPSSLTVTAGEKVTMSCKS SQSLLNSGNQKNYLTWYQQKPGQPP TLLIFWAFTRESGVPDRFTGSGSGT DFTLTINSVQAEDLAVYYCQNSYSY PFTFGSGTKLEIK | 125 |
| 101C4F12 | DIVMTQSPSSLTVTAGEKVTMSCKS SQSLLNSGNQRNYLTWYQQKPGQPP RLLIYWSSTRDSGVPDRFTGSGSRT DFTLTISSVQAEDLAVYYCQNNFIY PLTFGAGTKLELK | 126 |
| 103B2 | DIVMTQSPSSLTVTPGEKVTMSCRS SMSLFNSGNQKSYLSWYHQKPGQPP KLLIYWASTRDSGVPVRFTGSGSGT DFTLTISSVQAEDLAVYYCHNDYIY PLTFGAGTKLELK | 127 |
| 78E8G9G6 | DIVMTQSPSSLTVTAGEKVTMNCRS IQSLLNSGNQKNYLSWYQQKPGQPP KLLIYWASTRESGVPDRFTGSGSGT DFTLTIRSVLDEDLAVYYCQNSYSY PFTFGSGTKLEMK | 128 |
| 4F11E2 | DIVMTQSPSSLTVTAGEKVTLTCRS SQSLLNSGNRKNYLTWYQQIPGQPP KLLIYWASTRESGVPDRFTGSGSGT YFTLTISSVQAEDLAVYYCQNAYSY PFTFGSGTKLEKK | 129 |
| 10G7G11 | DIVMTQSPSSLTVTAGEKVTMTCKS SQSLFNSGNQRNYLTWYQRKPGQPP KLLIYWASTRESGVPDRFTGSGSGT YFTLTVSSVQAEDLAVYYCQNAYYF PFTFGSGTKLEKK | 130 |
| 12F1F4 | DIVMTQSPSSLTVTARERVSMTCKS SQSLFNSGNQRNYLTWYQQKPGQPP KLLIYWSSTRESGVPDRFTGSGSGT DFTLTISSVQAEDLAIYFCQNNYYY PFTFGSGTKLEIK | 131 |
| 78C10B6G4 | DIVMTQSPSSLTVTAGEKVTMSCKS SQSLLNSGNQKNYLTWYQQRPGQPP KLLIYRASSRESGVPVRFTGSGSGT DFTLTISSVQAEDLAVYYCQNDYIY PYTFGGGTKLEMN | 124 |
| 119G11D9 | DIVMTQSPSSLTVTAGERVTMRCRS TQSLFNSGNQKNYLTWYQQKPGQPP KLLIYVJASTRESGVPDRFTGGGSG TDFTLTISSVQAEDLAVYYCQNAYY YPLTFGAGTKLERK | 132 |
| 113G12E5E6 | DIVMTQSPSSLTVTAGERVTMSCKP SQSLLNSGNQKNYLAWYQQKPGQPP KLLLYWASTRESGVPDRFKGSGSGT DFTLTISSVQAEDLAVYYCQNAFYF PCTFGGGTKLEMK | 133 |
| 116A8B7 | DIVMTQSPSSLTVTAGEKVTMRCRS TQSLFNSGNQRNYLTWYQQKPGQPP KLLIYWASTRESGVPDRFTGSGSGT DFTLTISSVQAEDLAVYYCQNAYYY PLTFGVGTKLERK | 134 |
| 105F7G12 | DIVMTQSPSSLTVTAGERVTMSCRS SQSLLNSGNQKNYLAWYQQKPGQPP KLLLYWASTRESGVPDRFKGSGSGT DFTLTISSVQAEDLAVYYCQNAFYF PCTFGGGTKLEMK | 135 |
| 84E9E12 | DIVMTQSPSSLTVTTGEKVTMSCKS SQSVFNSGNQKNYLTWYQQKPGQPP KLLVYWASTRESGVPARFTGSGSGT VFTLTISSVQAEDLAVYYCQNDYYF PLTFGAGTRLELK | 136 |
| 103F4D4 | DIVMTQSPSSQTVTAGEKVTLSCRS SQSLLNGGNQKNYLTWYQQKPGQPP KLLIYWASTRESGVPDRFTGSGSGT YFTFTISSVQAEDLAVYYCQNAFYF PFTFGAGTKLELK | 137 |
| 110C12B6 | DIVMTQSPSSLTVTAGEKVTMRCRS TQSLFNSGNQRNYLTWYQQKPGQPP KLLIYWASTRESGVPDRFTGSGSGT DFTLTISSVQAEDLAVYYCQNAYYY PLTFGVGTKLERK | 134 |
| 85H12E8 | DIVMTQSPSSLTVTAGEKVTMNCKS SQSLLNSGNQRNYLSWYQQEPGQPP KLLIYWASTRESGVPDRFTGSGSGT DFTLTISNIQAEDLALYFCQNAFYF PFTFGSGTKLEIK | 138 |

TABLE 1-continued

Sequences of the variable regions of the antibodies

| Antibody chain | Sequence | SEQ ID NO: |
| --- | --- | --- |
| 103H2B4 | DILMTQSPSSLTVTAGEKVTMSCKS SQSLLNSGNQKNYLTWYQQKPGQSP KLLIYWASTRESGVPDRFTGSGSGT DFTLTISSVQAEDLAVYYCQNNYFY PLTFGVGTKLELK | 139 |
| 103F6D3 | DIVMTQSPSSQTVTAGEKVTLSCRS SQSLLNGGNQKNYLTWYQQKPGQPP KLLIYWASTRESGVPDRFTGSGSGT YFTFTISSVQAEDLAVYYCQNAYFY PFTFGAGTKLELK | 137 |
| 113E12F7 | DIVMTQSPSSLTVTTGEKVTMSCKS SQSLFNSGNQKNYLTWYQQKPGQSP KLLIYWASTRESGVPDRFTGSGSGT YFTLTISSVQAEDLAVYYCQNNYIY PLAFGTGTKLELK | 140 |
| 120B7B2 | DIVMTQSPSSLTVTAGEKVTMSCKS SQSLLNSGNQKNYLTWYQQRPGQPP KLLMYWASTRESGVPDRFTGSGSGT DFTLTISSGQAEDLAIYFCQNGYYF PFTFGSGTKLETK | 141 |
| 111B12D 11 | DIVMTQSPSSLTVTAGEKVTMRCRS SQSLFNSGNQRNYLTWYQQKPGQPP KLLIYWASTRESGVPDRFTGSGSGT DFTLTISSVQAEDLAVYYCQNNYIY PLAFGAGTKLELK | 142 |
| 111E7E2 | DIVMTQSPSSLTVTAGEKVTMSCKS SQSLFNSGNQKNYLTWYQQKPGQPP KLLIYWASTRESGVPDRFTGSGSGT DFTLTISSVQAEDLAVYYCQNNYIY PLAFGAGTKLELK | 143 |
| 100F4G12 | DIVMTQSPSSLTVTAGEKVTMRCKS TQSLLNSGNQRNYLTWYQQKPGQSP KLLIYWASTRESGVPERFTGSGSGT DFTLTISSVQAEDLAVYYCQNAYYY PLTFGPGTKLERK | 144 |

Heavy Chain

| Antibody chain | Sequence | SEQ ID NO: |
| --- | --- | --- |
| 64G11B4 | QVQLHQSGTELVRPGTSVKVSCKAS GYAFTNYLLEWVKQRPGQGLEWIGE INPGNGGSYNYEKFKGKATLTADKS SSTAYMQLSSLTSVDSAVYFCARIY YGNSFAYWGQGTLVTVSA | 145 |
| 65G8B8 | QVQLKESGPGLVAPSQSLSITCTVS GFSLTSYGVSWVRQPPGKGLEWLGV IWGDGNTIYHSALKSRLSISRDNSK RQVFLKVNSLQIDDTATYYCAKQGL YGHAMDYWGQGTSVIVSS | 146 |
| 56E8F10F4 | DVQLVESGGGLVQPGGSRKLSCTAS GFTFNSFGMNWVRQAPEKGLEWVAF ISGGSNTIHYLDTVKGRFTISRDNP KNTLFLQMTSLRSEDTAMYYCTRLA LGNAMDYWGQGTSVIVSS | 147 |
| 54A2C4 | EVQHVETGGGLVQPKGSLKLSCAAS GFTFNTNAMNWVRQAPGKGLEWVAR IRSKSNNYATYYADSVKDRFTISRD DSQSMLYVQMNNLKTEDTAMYYCVS GAYYGNSKAFDYWGQGTLVTVSA | 148 |
| 54A2C4' | QVQLHQSGTELVRPGTSVKVSCKAS GYAFTNYLLEWVKQRPGQGLEWIGE INPGNGGSYNEKFKGKATLTADKS SSTAYMQLSSLTSVDSAVYFCARIY YGNSFAYWGQGTLVTVSA | 145 |
| 54A2C4" | QVQLQQSGAELARPGASVKMSCKAS GYTFPTYSIHWLKQGPGQGLEWIGY INPSTIYTNYNQKFKYKATLTADKS SSTAYIQLSSLTSDDSAVYYCAREG YGRGNAMDYWGQGTSVTVSS | 149 |
| 44F6B11 | EVQLVESGGDLVKPGGSLKLSCAAS GFTFSNYGMSWVRQTPDKRLEWVAT FSYGDSHNYYSDSVKGRFTISRDIA KDALYLQMSSLRSEDTAIYYCARFG RGNTMDYWGQGTSVTVSL | 150 |
| 15C2B7 | QIQLVQSGPELRKPGETVKISCKAS GYTFTNYGMNWVKQAPGKGLKWMAW INANTGEPTYAEEFKGRFAFSLETS ARSAYLQINSLKNEDTATYFCARLT RGNSFDYWGQGTTLTVSS | 151 |
| 20F1E10 | QIQLVQSGPELKKPGETVKISCKAS GYTFTKYGMNWVRQAPGKGLKWMGW ISTNTGEPTYAEEFKGRFAFSLETS ASTAFLQINNLKNEDTATYFCARLV RGNSFDWGQGITLTVSS | 152 |
| 72C1B6A3 | QVQLQQSGGELVKPGASVKMSCKAF GYTFTTYPIEWMKQNHGKSLEWIGN FHPYNDDTKYNEKFKGKAKLTVEKS SSTVYLEVSRLTSDDSAVYYCARRA YGYPYAMDYWGQGTSVTVSS | 153 |
| 58G2C2 | QVHLQQSGAEWRPGTSVKVSCKASG YAFTNYLIEWIKKRPGQGLEWVGVI NPGRSGTNYNEKFKGKATLTADKSS STAYMQLSSLTSDDSAVYFCARTRY GGNAMDYWGQGTSVTVSS | 154 |
| 101C4F12 | QVQLKESGPGQVAPSQSLSIACTVS GFSLSSYGVHWVRQPPGKGLEWLGV IWAGGSTNYDSALMSRLTISKDNSR TRVFLKMNSLQTDDTAIYYCARSLY GNSLDSWGPGTTLTVSS | 155 |
| 103B2 | QVQLKESGPGLVAPSQSLSITCTVS GLSLTSFGVHWIRQPPGKGLEWLGV IWAGGSTNYNSALMSRLSISKDNSK SQVYLKMHSLQTDDTAMYYCARSLY GNSFDYWGQGTALTVSS | 156 |
| 40C10E3 | QVQLKESGPGLVAPSQSLSITCTVS GFSLSSYGVNWVRQPPGKGLEWLAA IRSDGIITYNSVLKSRLRISKDNSK SQVFLKMNSLQTDDTAMFYCARWFR GNVLDYWGQGTSVTVSS | 157 |
| 78E8G9G6 | QVQLKESGPGLVAPSQSLSITCTVS GFSLISYGVHWVRQPPGKGLEWLGV IWAGGRTNYNSALMSRLSISKDNSK SQVFLKMNSLQTYDTAMYYCARDRY GGNSLDYWGQGTSVTVSS | 158 |
| 4F11E2 | DVQLVESGGGLVQPGGSRKLSCAAS GFTFSTFGMHWVRQAPEKGLEWVAY ITSGNSPIYFTDTVKGRFTISRDNP KNTLFLQMTSLGSEDTAVYYCARSS YYGNSMDYWGQGTSVTVSS | 159 |
| 10G7G11 | QVQLKESGPGLVAPSQSLSITCTIS GFSLNTYGVHWVRQPPGKGLEWLWM LSDGNTVYNSSLKSRLSLTKDNSKS QLLLKMNSLQTDDTAIYYCARHKAY GNAMDYWGQGTSVTVSS | 160 |

TABLE 1-continued

Sequences of the variable regions of the antibodies

| Antibody chain | Sequence | SEQ ID NO: |
|---|---|---|
| 12F1F4 | QVQLKESGPGLVAPSQSLSITCTVSGFSLINYGVSWVRQPPGKGLEWLGVIWGDGNTNYQSALRSRLSIRKDTSKSQVFLKLNSVHTDGTATYYCAKVGRGNAMDHWGQGISVIVSS | 161 |
| 78C10B6G4 | QVQLKESGPGLVAPSQSLSITCTVSGFSLINYGVSWVRQPPGKGLEWLGVIRGDGNTNYQSALRSRLSIRKDTSKSQVFLKLNSVHTDGTATYYCAKVGRGNAMDHWGQGISVIVSS | 162 |
| 119G11D9 | EVQLQQSGPELVKPGASVKMSCKASGYTFTGFLMHWVKQKPGQGLEWIGYINPYNDGTKYSEKFKGKATLTSDKSSSTAFMELSSLTSDDSAVYYCARLDYGNAMDYWGQGTSVTVSS | 163 |
| 113G12E5E6 | QVQLKQSGPGLVQPSQSLSITCTVSDFSLTKYGVHWFRQSPGKGLEWLGVIWTGGNTDYNPALIPRLSFRKDNSKSQVFFKMNSLQSSDTAVYYCARNGYYGNAMDYWGQGTSVTVSS | 164 |
| 116A8B7 | EVQLQQSGPELVKPGASVKMSCKSSGYTFTGFLMHWVKQKPGQGLEWIGYINPYNDGTKYSEKFKGKATLTSDKSSSTAYMELSSLTSDDSAVYYCGRLDYGNAMDYWGQGTSVTVSS | 165 |
| 105F7G12 | QVQLKQSGPGLVQPSQSLSITCTVSDFSLTKYGVHWFRQSPGKGLEWLGVIWTGGNTDYNPALIPRLSFRKDNSKSQVFFKMNSLQSSDTAVYYCARNGYYGNAMDYWGQGTSVTVSS | 164 |
| 84E9E12 | DVQLQESGPGLVKPSQSLSLSCSVTGYSITSGYFWTWFRQFPGNKLEWMGYISYDGSNNYNPSLKNRISITRDTSKNQFFLKLNSVTTEDTATYYCASFRFFAYWGQGTLVTVSA | 166 |
| 103F4D4 | QVQLQQSGAELARPGASVKMSCKASGYTFPTYSIHWLKQGPGQGLEWIGYINPSTIYTNYNQKFKYKATLTADKSSSTAYIQLSSLTSDDSAVYYCAREGYGRGNAMDYWGQGTSVTVSS | 149 |
| 110C12B6 | EVQLQQSGPELVKPGASVKMSCKSSGYTFTGFLMHWVKQKPGQGLEWIGYINPYNDGTKYSEKFKGKATLTSDKSSSTAYMELSSLTSDDSAVYYCGRLDYGNAMDYWGQGTSVTVSS | 165 |
| 85HI2E8 | QVQLKESGPGLVAPSQSLSITCTVSGFSLSNYGVSWVRQPPGKGLEWLGVIWAGGNTNYNSALMSRLRISKDNSKSQVFLKMNSLQTDDTARYYCARHGYGKGNAMDNWGQGTSVTVSS | 167 |
| 103H2B4 | QVQLQQPGAEPVKPGASVKLSCKASGYSFTNFLTHWVRQRPGQGLEWIGEINPTNGRTYYNEKFKRKATLTVDKSSTTVYMQLSNLTPEDSAVFYCARIYYGNSMDYWGQGTLVTVSA | 168 |
| 103F6D3 | QVQLQQSGAELARPGASVKMSCKASGYTFPTYSIHWLKQGPGQGLEWIGYINPNTIYTNYNQKFKYKTTLTADKSSSTAYIQLSSLTSDDSAVYYCAREGYGRGNAMDYWGQGTSVTVSS | 169 |
| 113E12F7 | QVQLKESGPGLVAPSQSLSITCTVTGFSLSSYGVHWVRQPPGKGLEWLGVIWAGGSTNYDSALMSRLSISKDRSKSQVFLKMTSLQTDDTAMYYCARSLYGNSFDHWGQGTTLTVSS | 170 |
| 120B7B2 | EVQLQQSGPELVKPGASVKMSCKASGYTFTGYIIQWMKQKPGLGLEWIGFINPYNDGTKYNEQFKGKATLTSDKSSNAAYMELSSLTSEDSAVYYCARAYFGNSFAYWGQGTLVTVSA | 171 |
| 111B12D 11 | QVQLKESGPGLVAPSQSLSITCTVSGFSLTSYGVHWVRQPPGKGLEWLGVIWAGGSTNYDSTLMSRLSISKDRSKSQVFLKMTSLQTDDTAMYYCARSLYGNSFDHWGQGTTLTVSS | 172 |
| 111E7E2 | QVQLKESGPGLVAPSQSLSITCTVSGFSLTSYGAHWVRQPPGKGLEWLGVIWAGGSTNYDSALMSRLSISKDRSKSQVFLKMTSLQTDDTAMYYCARSLYGNSFDHWGQGTTLTVSS | 173 |
| 100F4G12 | EVQLQQSGPELVKPGASVKMSCKASGYTFTGFLMHWVKQKPGQGLEWIGYINPYNDGTKYSERFKGKATLTSDKSSSTAYMELSSLTSDDSAVYYCARLDYGNAMDYWGQGTSVTVSS | 174 |

Example 3. Production and Purification of Monoclonal Antibodies Reactive to CLD18A2

To produce mg amounts of antibody for functional characterization, hybridoma cells were seeded in dialysis based bioreactors (CELLine CL1000, Integra, Chur, CH) at $2 \times 10^6$ cells/ml. Antibody-containing supernatant was harvested once weekly. Each mouse monoclonal antibody was purified using Melon Gel (Pierce, Rockford, USA) and concentrated by ammonium sulphate precipitation. Antibody concentration and purity was estimated by sodium dodecylsulphate gel electrophoresis and coomassie staining.

Example 4. Binding of Murine Monoclonal Antibodies Reactive to CLD18A2

Figure 3:
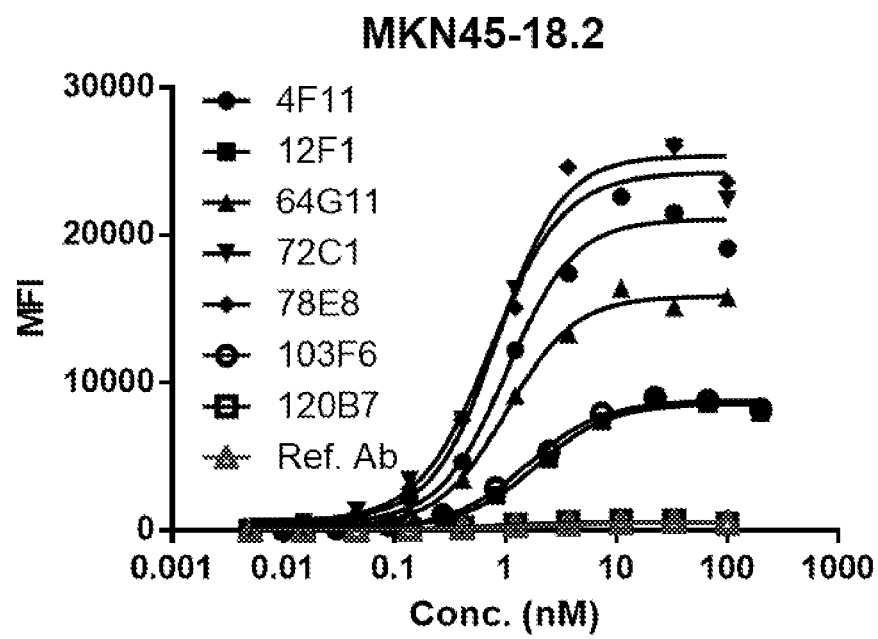
FIG. 3 shows that the purified murine antibodies can bind to MKN45 cells transfected with human CLD18A2 by flow cytometry with high EC50, compared with positive reference antibody.

MKN45 cells that over-expressed CLD18A2 were harvested from flasks. 100 μl of $1 \times 10^6$ cells/ml of cells were incubated with primary antibodies indicated as FIG. 3 in 3-fold serial dilutions starting from 100 nM to 0.003 nM for 30 minutes on ice. After being washed with 200 μl of FACS buffer twice, cells were incubated with secondary antibody for 30 minutes on ice. Cells were washed with 200 μl of FACS buffer twice and transferred to BD Falcon 5 ml tube and analyzed by FACS. The results of the study showed that the purified murine antibody could bind to MKN45 cells transfected with human CLD18A2 by flow cytometry with high EC50, compared with positive reference antibody.

Example 5. Binding of Murine Monoclonal Antibodies Reactive to CLD18A2 Mutant

SU620 cells that endogenously expressed CLD18A2 bearing the M149L mutation were harvested from flasks.

100 µl of 1×10⁶ cells/ml of cells were incubated with primary antibodies indicated as FIG. 4 in 3-fold serial dilutions starting from 100 nM to 0.003 nM for 30 minutes on ice. After being washed with 200 µl of FACS buffer twice, cells were incubated with secondary antibody for 30 minutes on ice. Cells were washed with 200 µl of FACS buffer twice and transferred to BD Falcon 5 ml tube and analyzed by FACS. The results of the study showed that the purified murine antibody could bind to SU620 cells endogenously expressing human CLD18A2 bearing M149L mutation by flow cytometry with high EC50, while the reference antibody did not (FIG. 4).

Example 6. Binding of Murine Monoclonal Antibodies Reactive to Mouse and Cyno CLD18A2

Figure 5:
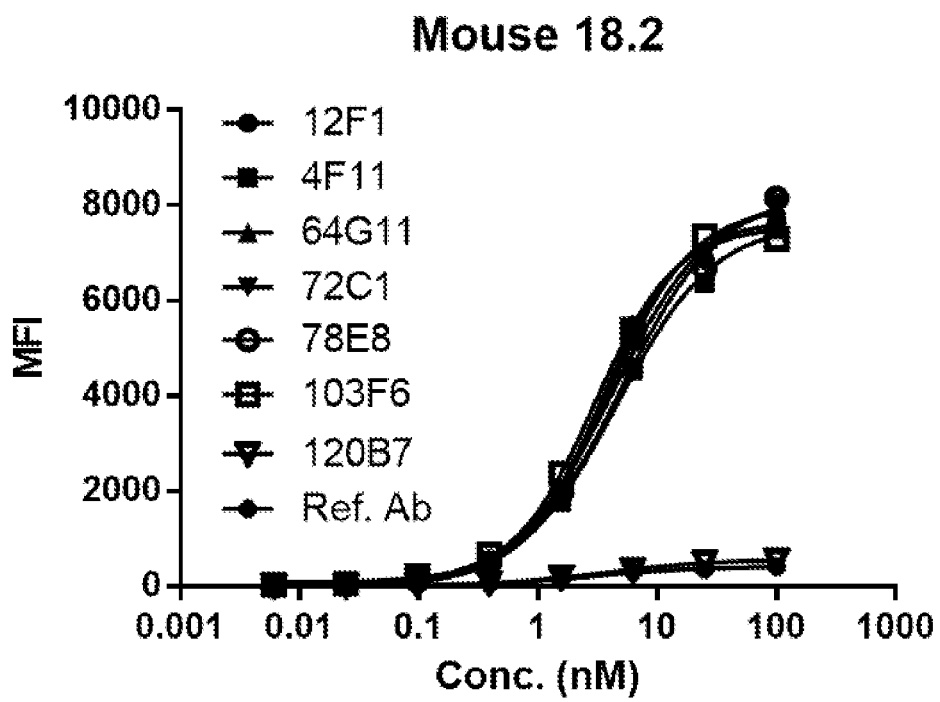
FIG. 5 shows that the purified murine antibodies can bind to HEK293 cells transfected with mouse CLD18A2 by flow cytometry with high EC50.
Figure 6:
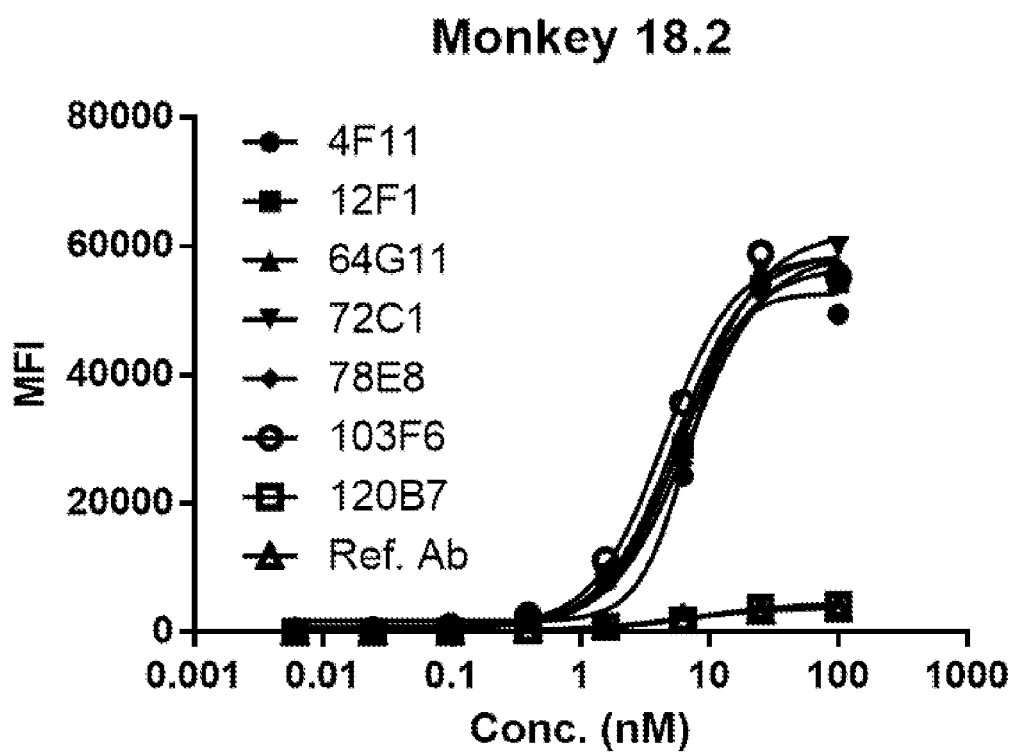
FIG. 6 shows that the purified murine antibodies can bind to HEK293 cells transfected with cyno CLD18A2 by flow cytometry with high EC50.
Figure 7:
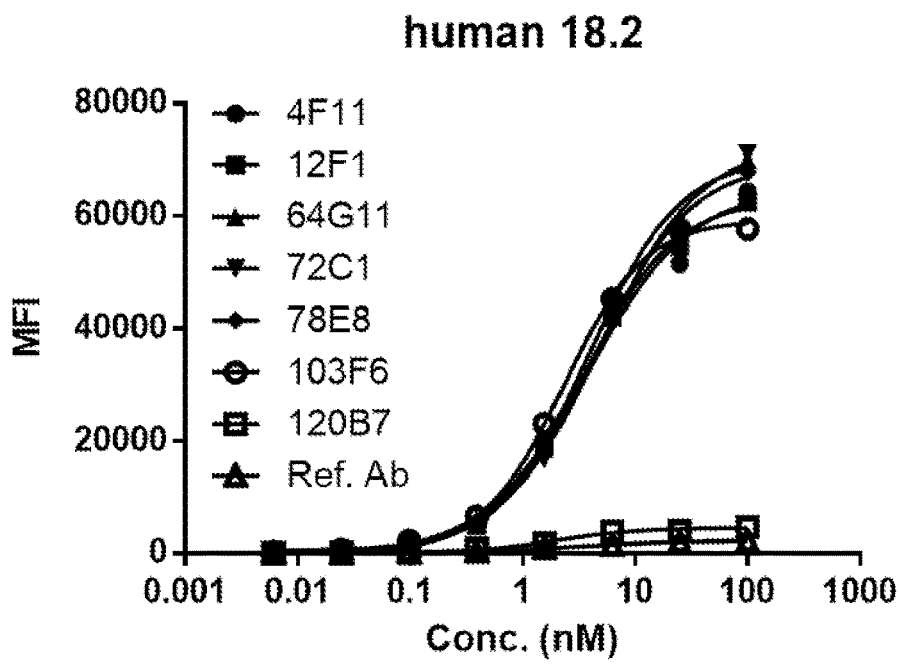
FIG. 7 shows that the purified murine antibodies can bind to HEK293 cells transfected with human CLD18A2 by flow cytometry with high EC50.

To evaluate these antibodies' cross-reactivities with mouse and cyno CLD18A2, HEK293 cells that over-expressed mouse, cyno or human CLD18A2 were harvested from flasks. 100 µl of 1×10⁶ cells/ml of cells were incubated with primary antibodies indicated as FIG. 3 in 3-fold serial dilutions starting from 100 nM to 0.003 nM for 30 minutes on ice. After being washed with 200 µl of FACS buffer twice, cells were incubated with secondary antibody for 30 minutes on ice. Cells were washed with 200 µl of FACS buffer twice and transferred to BD Falcon 5 ml tube and analyzed by FACS. The results of the study showed that the purified murine antibodies can bind to mouse and cyno CLD18A2 by flow cytometry with high EC50, at least similar to the reference antibodies (FIGS. 5, 6 and 7).

Example 7. Binding of Chimeric Antibodies Reactive to CLD18A2

The murine VH and VK genes were produced synthetically and then respectively cloned into vectors containing the human gamma 1 and human kappa constant domains. The purified chimeric antibodies were produced from transfected CHOs cells.

Figure 8:
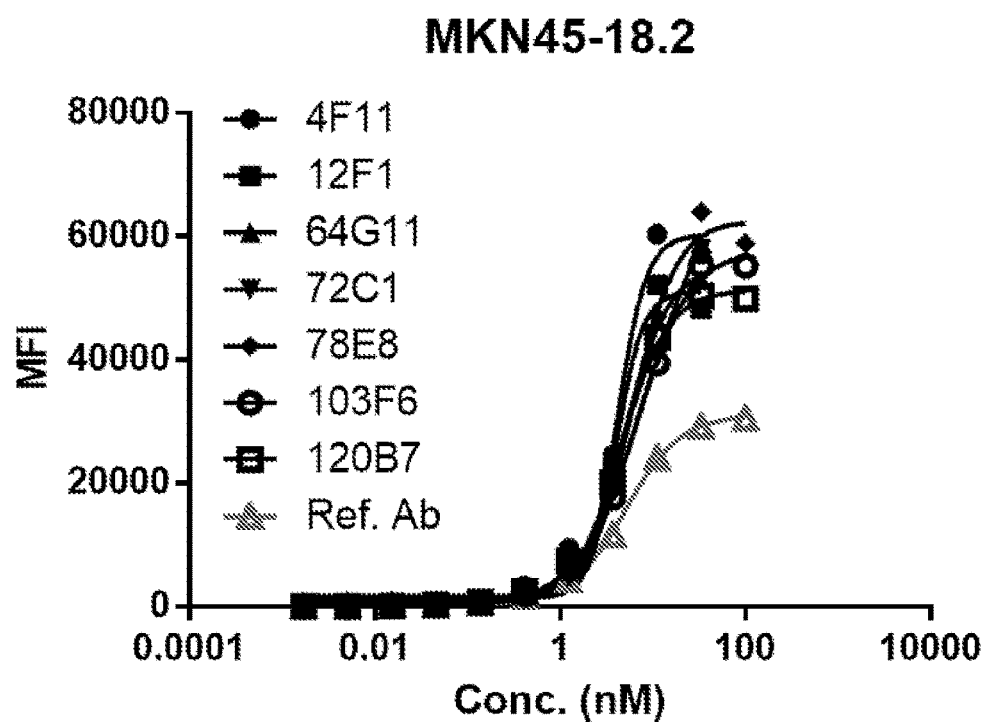
FIG. 8 shows that the chimeric antibodies can bind to MKN45 cells transfected with human CLD18A2 by flow cytometry with high EC50, compared with positive reference antibody.
Figure 9:
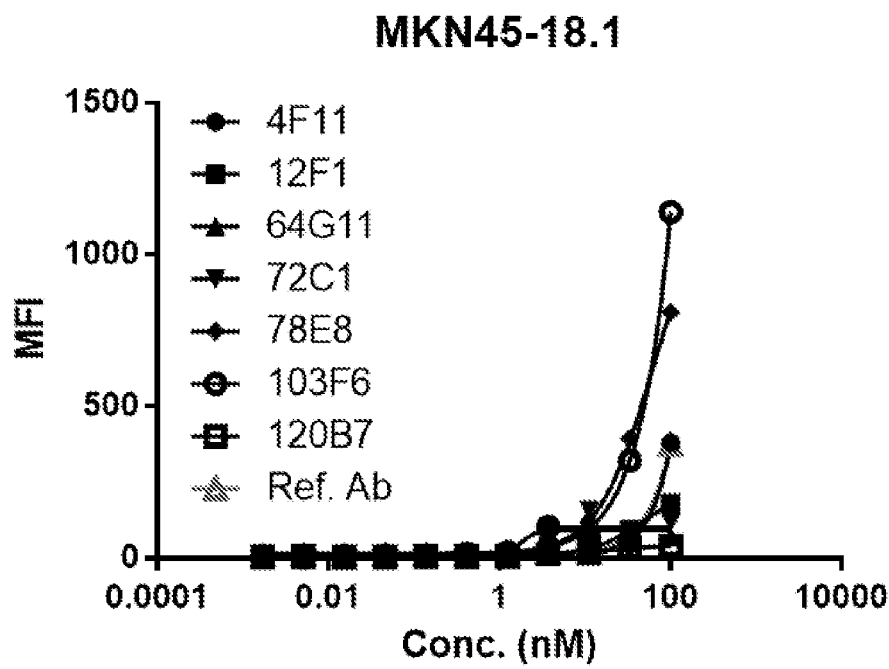
FIG. 9 shows that the chimeric antibodies can not bind to MKN45 cells transfected with human CLD18A1 by flow cytometry.

MKN45 cells that stably expressed human CLD18A2 or CLD18A1 were harvested from flasks. 100 µl of 1×10⁶ cells/ml of cells were incubated with primary chimeric antibodies indicated as FIG. 4 in 3-fold serial dilutions starting from 100 nM to 0.003 nM for 30 minutes on ice. After being washed with 200 µl of FACS buffer twice, cells were incubated with secondary antibody for 30 minutes on ice. Cells were washed with 200 µl of FACS buffer twice and transferred to BD Falcon 5 ml tube and analyzed by FACS. The results of the study showed that the chimeric antibodies can bind to human CLD18A2 with high EC50, but not CLD18A1 (FIGS. 8 and 9).

Example 8. Antibody-Dependent Cellular Cytotoxicity (ADCC) of Chimeric Antibodies The ADCC Reporter Bioassay uses an alternative readout at an earlier point in ADCC MOA pathway activation: the activation of gene transcription through the NFAT (nuclear factor of activated T-cells) pathway in the effector cell. In addition, the ADCC Reporter Bioassay uses engineered Jurkat cells stably expressing the FcγRIIIa receptor, V158 (high affinity) variant, and an NFAT response element driving expression of firefly luciferase as effector cells. Antibody biological activity in ADCC MOA is quantified through the luciferase produced as a result of NFAT pathway activation; luciferase activity in the effector cell was quantified with luminescence readout (FIG. 1). Signal was high, and assay background was low.

Serial dilutions of claudin 18.2 chimeric monoclonal antibody or Ref. Ab were incubated for 6 hours of induction at 37° C. with engineered Jurkat effector cells (ADCC Bioassay Effector Cells), with or without ADCC Bioassay Target Cells (expressing claudin 18.2). Luciferase activity was quantified using Bio-Glo™ Reagent (Table 2). The results show that these chimeric antibodies have very strong ADCC activities.

TABLE 2

EC50 of the tested antibodies

| Antibody | EC50 (pM) |
|---|---|
| 4F11E2 | 22.18 |
| 12F1F4 | 36.77 |
| 64G11B4 | 125.7 |
| 72C1B6A3 | 46.32 |
| 78E8G9G6 | 15.86 |
| 103F6D3 | 79.53 |
| 120B7B2 | 5.806 |
| Ref Ab | 458.5 |

Example 9. Humanization of the 4F11E2, 72C1B6A3 and 120B7B2 Mouse mAbs

The mAb 4F11E2, 72C1B6A3 and 120B7B2 variable region genes were employed to create humanized MAbs. In the first step of this process, the amino acid sequences of the VH and VL of MAb were compared against the available database of human Ig gene sequences to find the overall best-matching human germline Ig gene sequences.

The amino acid sequences of the humanized antibodies are listed in Table 3 below.

TABLE 3

Humanized sequences

| Name | Sequence | SEQ ID NO: |
|---|---|---|
| 4F11VH_1 (grafted VH) | EVQLVESGGGLVQPGGSLRLSCAAS GFTFSTFGMHWVRQAPGKGLEWVSY ITSGNSPIYFTDTVKGRFTISRDNA KNSLYLQMNSLRAEDTAVYYCARSS YYGNSMDYWGQGTLVTVSS | 175 |
| 4F11VH_2 | EVQLVESGGGLVQPGGSLRLSCAAS GFTFSTFGMHWVRQAPGKGLEWVAY ITSGNSPIYFTDTVKGRFTISRDNA KNSLYLQMNSLRAEDTAVYYCARSS YYGNSMDYWGQGTLVTVSS | 176 |
| 4F11VH_3 | EVQLVESGGGLVQPGGSLRLSCAAS GFTFSTFGMHWVRQAPGKGLEWVAY ITSGNSPIYFTDTVKGRFTISRDNA KNTLYLQMNSLRAEDTAVYYCARSS YYGNSMDYWGQGTLVTVSS | 177 |
| 4F11VL_1 (grafted VL) | DIVMTQSPDSLAVSLGERATINCRS SQSLLNSGNRKNYLTWYQQKPGQPP KLLIYWASTRESGVPDRFSGSGSGT DFTLTISSLQAEDVAVYYCQNAYSY PFTFGGGTKLEIK | 178 |

TABLE 3-continued

Humanized sequences

| Name | Sequence | SEQ ID NO: |
|---|---|---|
| 4F11VL_2 | DTVMTQSPDSLAVSLGERATINCRSSQSLLNSGNRKNYLTWYQQKPGQPPKLLIYWASTRESGVPDRFSGSGSGTDFTLTISSVQAEDVAVYYCQNAYSYPFTFGGGTKLEIK | 179 |
| 4F11VL_3 | DTVMTQSPDSLAVSLGERVTLNCRSSQSLLNSGNRKNYLTWYQQKPGQPPKLLIYWASTRESGVPDRFSGSGSGTDFTLTISSVQAEDVAVYYCQNAYSYPFTFGGGTKLEIK | 180 |
| 72C1VH_1 (grafted VH) | QVQLVQSGAEVKKPGASVKVSCKASGYTFTTYPIEWVRQAPGQRLEWMGNFHPYNDDTKYNEKFKGRVTITRDTSASTAYMELSSLRSEDTAVYYCARRAYGYPYAMDYWGQGTLVTVSS | 181 |
| 72C1VH_2 | QVQLVQSGAEWKPGASVKVSCKASGYTFTTYPIEWMRQAPGQRLEWMGNFHPYNDDTKYNEKFKGRVTITVDTSASTAYMELSSLRSEDTAVYYCARRAYGYPYAMDYWGQGTLVTVSS | 182 |
| 72C1VH_3 | QVQLVQSGAEWKPGASVKVSCKASGYTFTTYPIEWMKQAPGQRLEWMGNFHPYNDDTKYNEKFKGRVTITVDTSASTAYMEVSSLRSEDTAVYYCARRAYGYPYAMDYWGQGTLVTVSS | 183 |
| 72C1VH_4 | QVQLVQSGAEWKPGASVKMSCKASGYTFTTYPIEWMKQAPGQRLEWMGNFHPYNDDTKYNEKFKGRVTLTVDTSASTVYLEVSSLRSEDTAVYYCARRAYGYPYAMDYWGQGTLVTVSS | 184 |
| 72C1VL_1 (grafted VL) | DIVMTQSPDSLAVSLGERATINCKSSQSLLNSGNQKNYLTWYQQKPGQPPKLLIYRASSRESGVPDRFSGSGSGTDFTLTISSLQAEDVAVYYCQNDYIYPYTFGGGTKLEIK | 185 |
| 72C1VL_2 | DIVMTQSPDSLAVSLGERATISCKSSQSLLNSGNQKNYLTWYQQKPGQPPKLLIYRASSRESGVPDRFSGSGSGTDFTLTISSLQAEDVAVYYCQNDYIYPYTFGGGTKLEIK | 186 |
| 72C1VL_3 | DIVMTQSPDSLAVSLGERVTMSCKSSQSLLNSGNQKNYLTWYQQKPGQPPKLLIYRASSRESGVPDRFSGSGSGTDFTLTISSVQAEDVAVYYCQNDYIYPYTFGGGTKLEIK | 187 |
| 120B7VH_1 (grafted VH) | QVQLVQSGAEVKKPGASVKVSCKASGYTFTGYIIQWVRQAPGQRLEWMGFINPYNDGTKYNEQFKGRVTITRDTSASTAYMELSSLRSEDTAVYYCARAYFGNSFAYWGQGTLVTVSS | 188 |
| 120B7VH_2 | QVQLVQSGAEWKPGASVKVSCKASGYTFTGYIIQWMRQAPGQRLEWMGFINPYNDGTKYNEQFKGRVTITSDTSASAAYMELSSLRSEDTAVYYCARAYFGNSFAYWGQGTLVTVSS | 189 |
| 120B7VH_3 | QVQLVQSGAEWKPGASVKVSCKASGYTFTGYIIQWMKQAPGQRLEWIGFINPYNDGTKYNEQFKGRATITSDTSASAAYMELSSLRSEDTAVYYCARAYFGNSFAYWGQGTLVTVSS | 190 |
| 120B7VH_4 | EVQLVQSGAEWKPGASVKMSCKASGYTFTGYIIQWMKQAPGQRLEWIGFINPYNDGTKYNEQFKGRATLTSDTSASAAYMELSSLRSEDTAVYYCARAYFGNSFAYWGQGTLVTVSS | 191 |
| 120B7VL_1 (grafted VL) | DIVMTQSPDSLAVSLGERATINCKSSQSLLNSGNQKNYLTWYQQKPGQPPKLLIYWASTRESGVPDRFSGSGSGTDFTLTISSLQAEDVAVYYCQNGYYPFTFGGGTKLEIK | 192 |
| 120B7VL_2 | DIVMTQSPDSLAVSLGERATISCKSSQSLLNSGNQKNYLTWYQQKPGQPPKLLMYWASTRESGVPDRFSGSGSGTDFTLTISSLQAEDVAVYYCQNGYYPFTFGGGTKLEIK | 193 |
| 120B7VL_3 | DIVMTQSPDSLAVSLGERATISCKSSQSLLNSGNQKNYLTWYQQKPGQPPKLLMYWASTRESGVPDRFSGSGSGTDFTLTISSGQAEDVAVYFCQNGYYPFTFGGGTKLEIK | 194 |
| 120B7VL_4 | DIVMTQSPDSLAVSLGERVTMSCKSSQSLLNSGNQKNYLTWYQQKPGQPPKLLMYWASTRESGVPDRFSGSGSGTDFTLTISSGQAEDVAVYFCQNGYYPFTFGGGTKLEIK | 195 |

The humanized VH and VL genes were produced synthetically and then respectively cloned into vectors containing the human gamma 1 and human kappa constant domains. The pairing of the human VH and the human VL created the humanized antibodies (see Table 4).

TABLE 4

Humanized antibodies with their VH an VL regions

4F11E2

| VH VL | 4F11VH_1 | 4F11VH_2 | 4F11VH_3 |
|---|---|---|---|
| 4F11VL_1 | hu4F11.1 | hu4F11.4 | hu4F11.7 |
| 4F11VL_2 | hu4F11.2 | hu4F11.5 | hu4F11.8 |
| 4F11VL_3 | hu4F11.3 | hu4F11.6 | hu4F11.9 |

72C1B6A3

| VH VL | 72C1VH_1 | 72C1VH_2 | 72C1VH_3 | 72C1VH_4 |
|---|---|---|---|---|
| 72C1VL_1 | hu72C1.10 | hu72C1.13 | hu72C1.16 | hu72C1.19 |
| 72C1VL_2 | hu72C1.11 | hu72C1.14 | hu72C1.17 | hu72C1.20 |
| 72C1VL_3 | hu72C1.12 | hu72C1.15 | hu72C1.18 | hu72C1.21 |

120B7B2

| VH VL | 120B7VH_1 | 120B7VH_2 | 120B7VH_3 | 120B7VH_4 |
|---|---|---|---|---|
| 120B7VL_1 | hu120B7.22 | hu120B7.26 | hu120B7.30 | hu120B7.34 |
| 120B7VL_2 | hu120B7.23 | hu120B7.27 | hu120B7.31 | hu120B7.35 |
| 120B7VL_3 | hu120B7.24 | hu120B7.28 | hu120B7.32 | hu120B7.36 |
| 120B7VL_4 | hu120B7.25 | hu120B7.29 | hu120B7.33 | hu120B7.37 |

Example 10. Binding of Humanized Antibodies Reactive to CLD18A2

Figure 10:
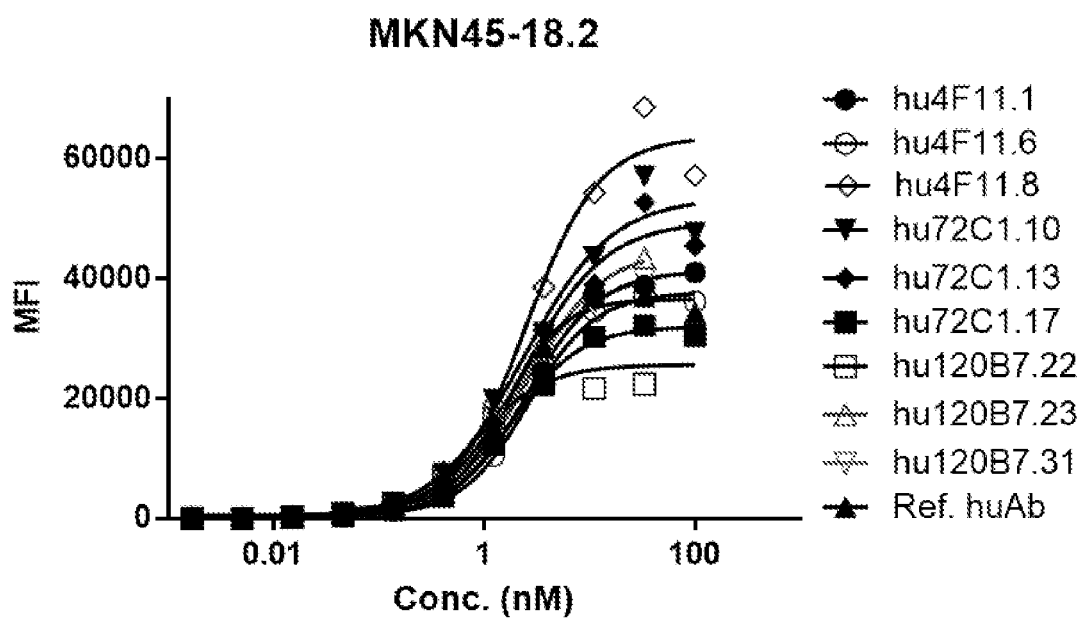
FIG. 10 shows that humanized antibodies can bind to MKN45 cells transfected with human CLD18A2 by flow cytometry with high EC50, compared with positive reference antibody.
Figure 11:
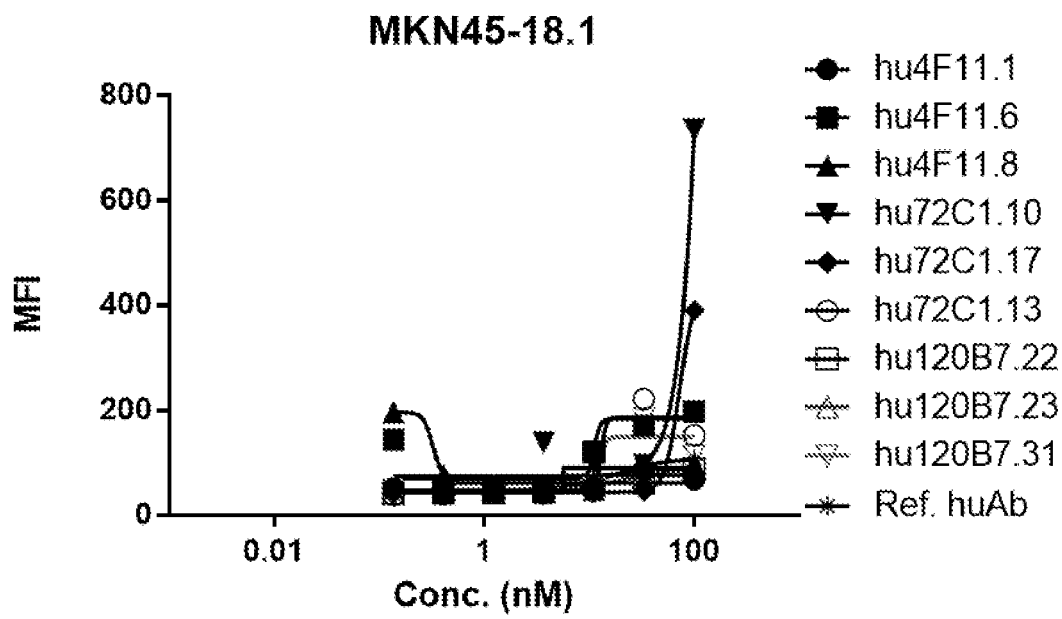
FIG. 11 shows that the humanized antibodies cannot bind to MKN45 cells transfected with human CLD18A1 by flow cytometry.

MKN45 cells that stably expressed human CLD18A2 or CLD18A1 were harvested from flasks. 100 μl of 1×10$^6$ cells/ml of cells were incubated with primary humanized antibodies indicated as FIG. 4 in 3-fold serial dilutions starting from 100 nM to 0.003 nM for 30 minutes on ice. After being washed with 200 μl of FACS buffer twice, cells were incubated with secondary antibody for 30 minutes on ice. Cells were washed with 200 μl of FACS buffer twice and transferred to BD Falcon 5 ml tube and analyzed by FACS. The results of the study showed that the indicated humanized antibodies can bind to human CLD18A2 with high EC50, but not CLD18A1 (FIGS. 10 and 11).

Example 11. Binding of PTM (Post-Translational Modification) De-Risk Humanized Antibodies Reactive to CLD18A2

Post-translational modifications (PTMs) can cause problems during the development of a therapeutic protein such as increased heterogeneity, reduced bioactivity, reduced stability, immunogenicity, fragmentation and aggregation. The potential impact of PTMs depends on their location and in some cases on solvent exposure. The CDRs of sequence were analyzed for the following potential PTMs: asparagine deamidation, aspartate isomerization, free cysteine thiol groups, N-glycosylation, oxidation, fragmentation by potential hydrolysis site etc.

To reduce the risk of developing PTM in 4F11E2, 72C1B6A3 and 120B7B2, some concerned amino acids in the VH and VL were mutated. And then nine antibodies were generated:

| Clones | HC:LC* | No. |
|---|---|---|
| 4F11E2 | HC N55Q-LC N31E | 1 |
| | HC N55Q-LC S32A | 2 |
| | HC N55E-LC S32A | 3 |
| | HC N55E&N104Q-LC S32A | 8 |
| | HC N55E&N104E-LC S32A | 9 |
| | HC N55E&S105A-LC S32A | 10 |
| 72C1B6A3 | HC WT-LC N31E | 4 |
| | HC WT-LC S32A | 5 |
| 120B7B2 | HC G57D&S104A-LC-N96E&N31E | 6 |
| | HC G57D&S104A-LC-S32A&G97A | 7 |

*The amino acid location (e.g., N55) is according to the amino acid residue number in the corresponding VH or VL amino acid sequence, not Kabat or Chothia.

| Antibody | Mutant | Sequence (mutation highlighted) | SEQ ID NO: |
|---|---|---|---|
| 4F11E2 | HC N55Q | EVQLVESGGGLVQPGGSLRLSCAAS GFTFSTFGMHWVRQAPGKGLEWVSY ITSGQSPIYFTDTVKGRFTISRDNA KNSLYLQMNSLRAEDTAVYYCARSS YYGNSMDYWGQGTLVTSS | 196 |
| | HC N55E | EVQLVESGGGLVQPGGSLRLSCAAS GFTFSTFGMHWVRQAPGKGLEWVSY ITSGESPIYFTDTVKGRFTISRDNA KNSLYLQMNSLRAEDTAVYYCARSS YYGNSMDYWGQGTLVTSS | 197 |
| | HC N55E & N104Q | EVQLVESGGGLVQPGGSLRLSCAAS GFTFSTFGMHWVRQAPGKGLEWVSY ITSGESPIYFTDTVKGRFTISRDNA KNSLYLQMNSLRAEDTAVYYCARSS YYGQSMDYWGQGTLVTSS | 198 |
| | HC N55E & N104E | EVQLVESGGGLVQPGGSLRLSCAAS GFTFSTFGMHWVRQAPGKGLEWVSY ITSGESPIYFTDTVKGRFTISRDNA KNSLYLQMNSLRAEDTAVYYCARSS YYGESMDYWGQGTLVTSS | 199 |
| | HC N55E & S105A | EVQLVESGGGLVQPGGSLRLSCAAS GFTFSTFGMHWVRQAPGKGLEWVSY ITSGESPIYFTDTVKGRFTISRDNA KNSLYLQMNSLRAEDTAVYYCARSS YYGNAMDYWGQGTLVTSS | 200 |
| | LC N31E | DIVMTQSPDSLAVSLGERATINCRS SQSLLESGNRKNYLTWYQQKPGQPP KLLIYWASTRESGVPDRFSGSGSGT DFTLTISSLQAEDVAVYYCQNAYSY PFTFGGGTKLEIK | 201 |
| | LC S32A | DIVMTQSPDSLAVSLGERATINCRS SQSLLNAGNRKNYLTWYQQKPGQPP KLLIYWASTRESGVPDRFSGSGSGT DFTLTISSLQAEDVAVYYCQNAYSY PFTFGGGTKLEIK | 202 |
| 72C1B6A3 | HC WT | QVQLVQSGAEVKKPGASVKVSCKAS GYTFTTYPIEWVRQAPGQRLEWMGN FHPYNDDTKYNEKFKGRVTITRDTS ASTAYMELSSLRSEDTAVYYCARRA YGYPYAMDYWGQGTLVTSS | 181 |
| | LC S32A | DIVMTQSPDSLAVSLGERATINCKS SQSLLNAGNQKNYLTWYQQKPGQPP KLLIYRASSRESGVPDRFSGSGSGT DFTLTISSLQAEDVAVYYCQNDYIY PYTFGGGTKLEIK | 203 |
| | LCN31E | DIVMTQSPDSLAVSLGERATINCKS SQSLLESGNQKNYLTWYQQKPGQPP KLLIYRASSRESGVPDRFSGSGSGT DFTLTISSLQAEDVAVYYCQNDYIY PYTFGGGTKLEIK | 204 |
| 120B7B2 | HC G57D &S104A | QVQLVQSGAEVKKPGASVKVSCKAS GYTFTGYIIQWVRQAPGQRLEWMGF INPYNDDTKYNEQFKGRVTITRDTS ASTAYMELSSLRSEDTAVYYCARAY FGNAFAYWGQGTLVTSS | 205 |
| | LC-S32A &G97A | DIVMTQSPDSLAVSLGERATINCKS SQSLLNAGNQKNYLTWYQQKPGQPP KLLIYWASTRESGVPDRFSGSGSGT DFTLTISSLQAEDVAVYYCQNAYYF PFTFGGGTKLEIK | 206 |
| | LC-N96E &N31E | DIVMTQSPDSLAVSLGERATINCKS SQSLLESGNQKNYLTWYQQKPGQPP KLLIYWASTRESGVPDRFSGSGSGT DFTLTTSSLQAEDVAVYYCQEGYYF PFTFGGGTKLEIK | 207 |

Figure 12:
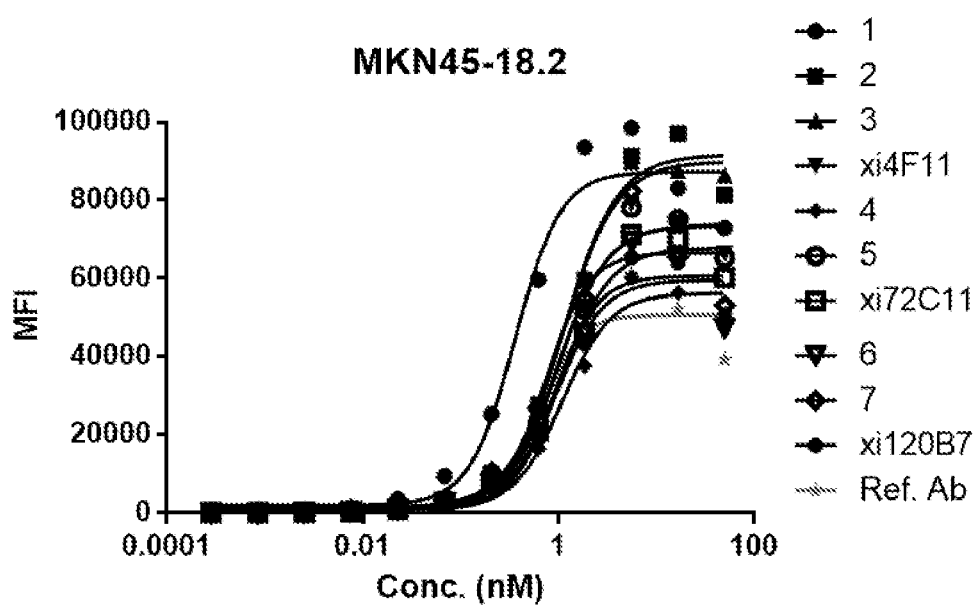
FIG. 12 shows that humanized antibodies with CDR mutation can bind to MKN45 cells transfected with human CLD18A2 by flow cytometry with high EC50, compared with positive reference antibody.
Figure 13:
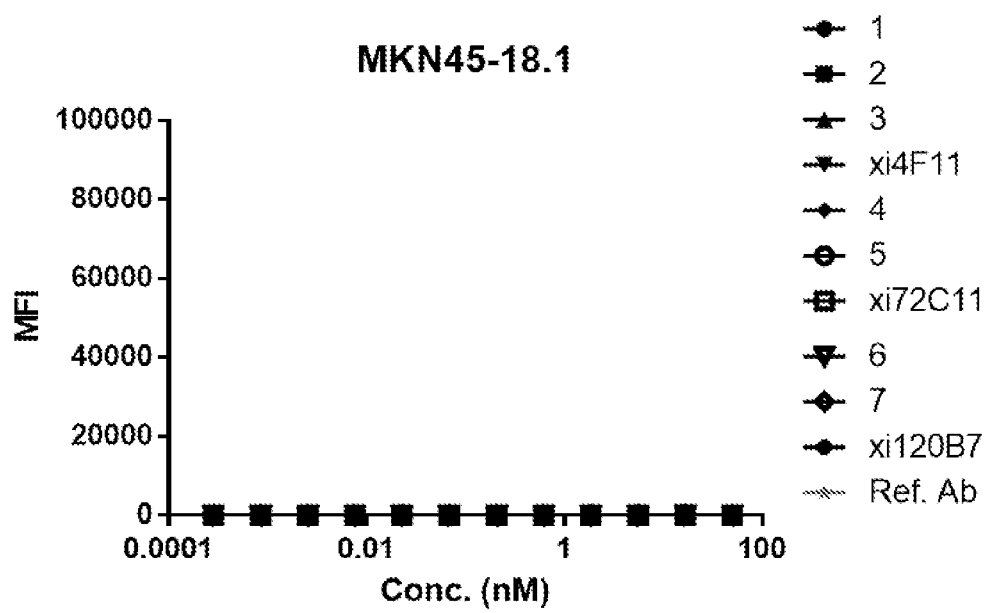
FIG. 13 shows that the humanized antibodies with CDR mutation cannot bind to MKN45 cells transfected with human CLD18A1 by flow cytometry.

MKN45 cells that stably expressed human CLD18A2 or CLD18A1 were harvested from flasks. 100 μl of 1×10$^6$ cells/ml of cells were incubated with primary mutated humanized antibodies indicated as FIG. 4 in 3-fold serial dilutions starting from 100 nM to 0.003 nM for 30 minutes on ice. After being washed with 200 μl of FACS buffer twice, cells were incubated with secondary antibody for 30 minutes on ice. Cells were washed with 200 µl of FACS buffer twice and transferred to BD Falcon 5 ml tube and analyzed by FACS. The results of the study showed that the indicated antibodies can bind to human CLD18A2 with high EC50, but not CLD18A1 (FIGS. 12 and 13).

Figure 14:
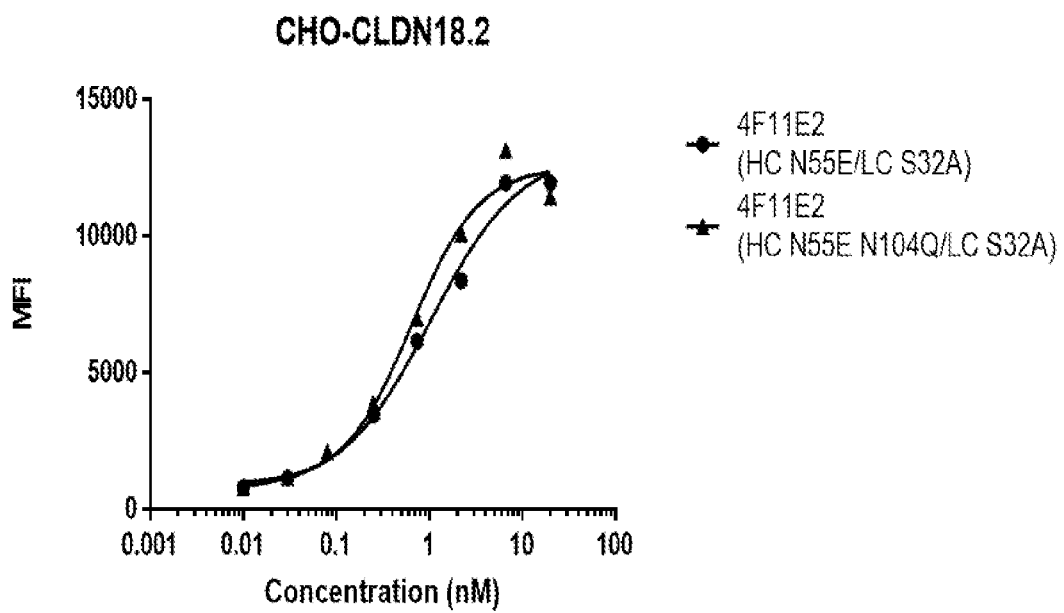
FIG. 14 shows that the de-risked variants had potent binding to cell surface CLD18A2.

To evaluate the de-risked variants of 4F11E2d (HC N55E/LC S32A) and 4F11E2d (H N55E N104Q/LC S32A) antigen binding potency, the variants were tested in a cell-based binding assay. Serially diluted anti-CLDN18.2 antibodies, starting from 100 nM, were incubated with $10^5$ cells for 30 minutes on ice. After being washed with FACS buffer, cells were then incubated with APC labeled secondary antibody for another 30 minutes on ice. Cells bound with antibodies were analyzed by FACS. The variants showed potent binding to cell surface claudin 18.2 (FIG. 14).

Example 12. Antibody-Dependent Cellular Cytotoxicity (ADCC) of PTM De-Risked Humanized Antibodies Serial dilutions of claudin 18.2 PTM de-risked humanized antibodies or Ref. Ab were incubated for 6 hours of induction at 37° C. with engineered Jurkat effector cells (ADCC Bioassay Effector Cells), with or without ADCC Bioassay Target Cells (expressing claudin 18.2). Luciferase activity was quantified using Bio-Glo™ Reagent (Table 5). The results show that these humanized antibodies have very strong ADCC activities.

TABLE 5

ADCC

| No. | Tested antibody | EC50 (pM) |
|---|---|---|
| 1 | 4F11E2 -HC N55Q-LC N31E | 238.1 |
| 2 | 4F11E2 -HC N55Q-LC S32A | 413.9 |
| 3 | 4F11E2 -HC N55E-LCS32A | 148.1 |
| 4 | 72C1B6A3-HC WT-LC N31E | 1651 |
| 5 | 72C1B6A3-HC WT- LCS32A | 190.5 |
| 6 | 120B7B2-HC G57D&104A- LC-N96E&N31E | 492.6 |
| 7 | 120B7B2-HC G57D&10 4A- LC-S32A&G97A | 113.9 |
| Ref. Ab | Ref. Ab | 158.3 |

Example 13. Epitope Mapping

All amino acids of extracellular domain of claudin 18.2 were individually mutated to A. Each mutated or wildtype claudin 18.2 was transfected into Hek293 cells. The expression of claudin 18.2 was evaluated by indicated antibodies. The results are shown in FIG. 15 (only amino acid residues at which the mutation reduced bindings are shown).

Figure 15:
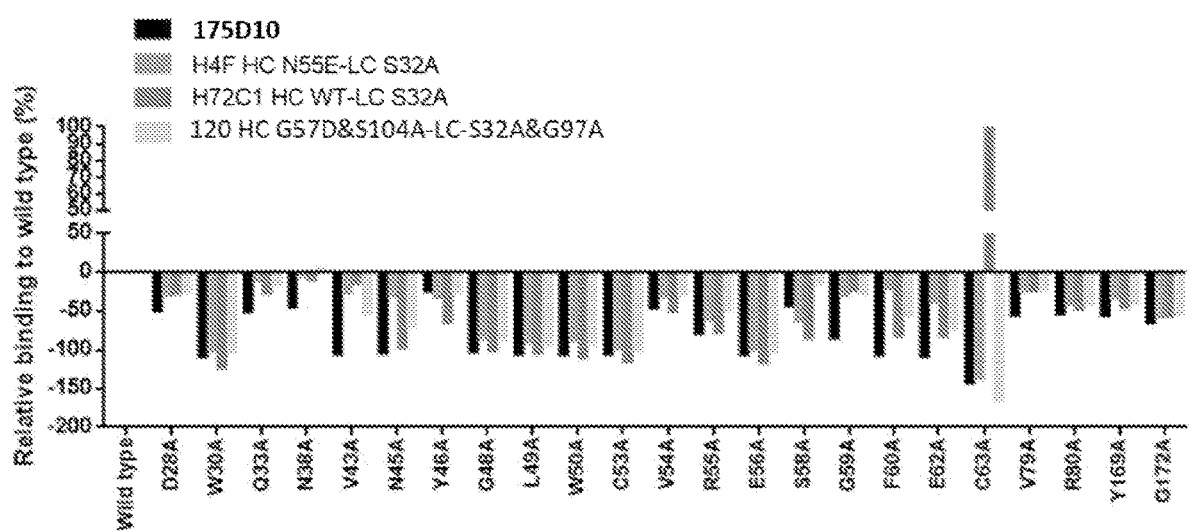
FIG. 15 shows that certain mutations of CLD18A2 have significant effect on the indicated antibodies binding to HEK293 cells transfected these mutants, suggesting that these amino acid residues constitute at least part of the epitope.
Figure 16:
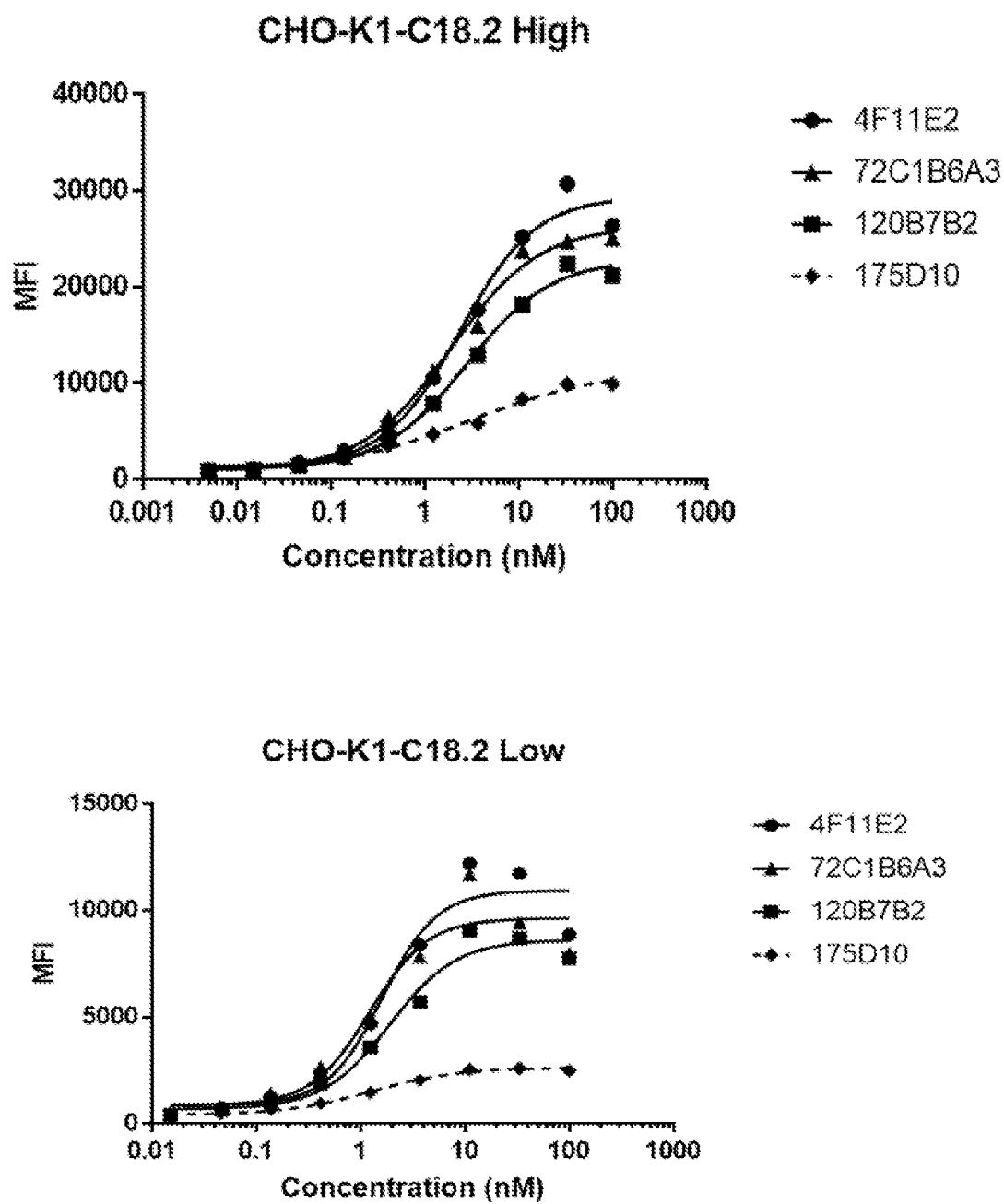
FIG. 16 shows that antibodies 4F11E2, 72C1B6A3 and 120B7B2 had superior binding in both claudin 18.2 high and low CHO-K1 cells, as compared to 175D10.
Figure 17:
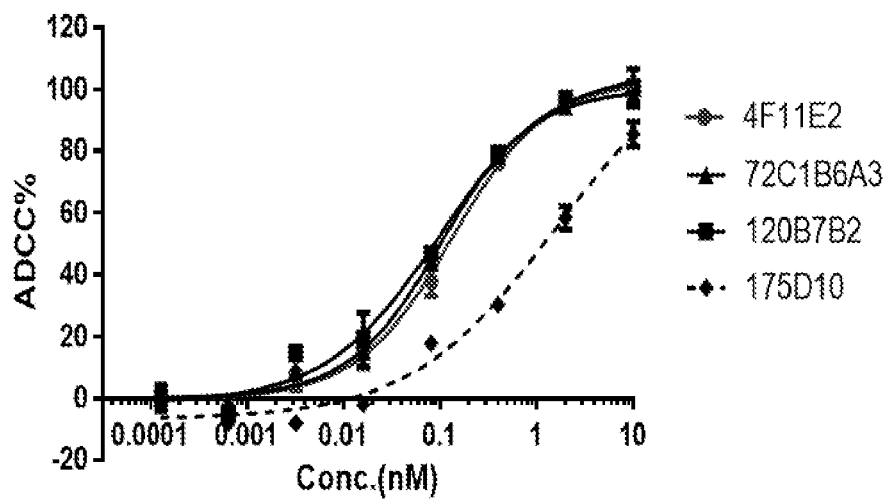
FIG. 17 shows the potent ADCC testing results of 4F11E2, 72C1B6A3 and 120B7B2 using 175D10 antibody as a reference.

As shown in FIG. 15, amino acids W30, N45, Y46, G48, L49, W50, C53, V54, R55, E56, S58, F60, E62, C63, R80, Y169, and G172 are involved in the binding of the three tested antibodies, 4F11E2 (H4F), 72C186A3 (H72C1) and 120B7B2 (120), or the reference antibody 175D10 (IMAB362). W30 appeared to form a cluster of residues at the first half of the first extracellular domain of the claudin 18.2 protein. N45, Y46, G48, L49, W50, C53, V54, R55, E56, S58, F60, E62 and C63 appeared to be a second cluster of residues within the same extracellular domain. Y169 and G172, on the other hand, are located at or close to the second extracellular domain.

Figure 20:
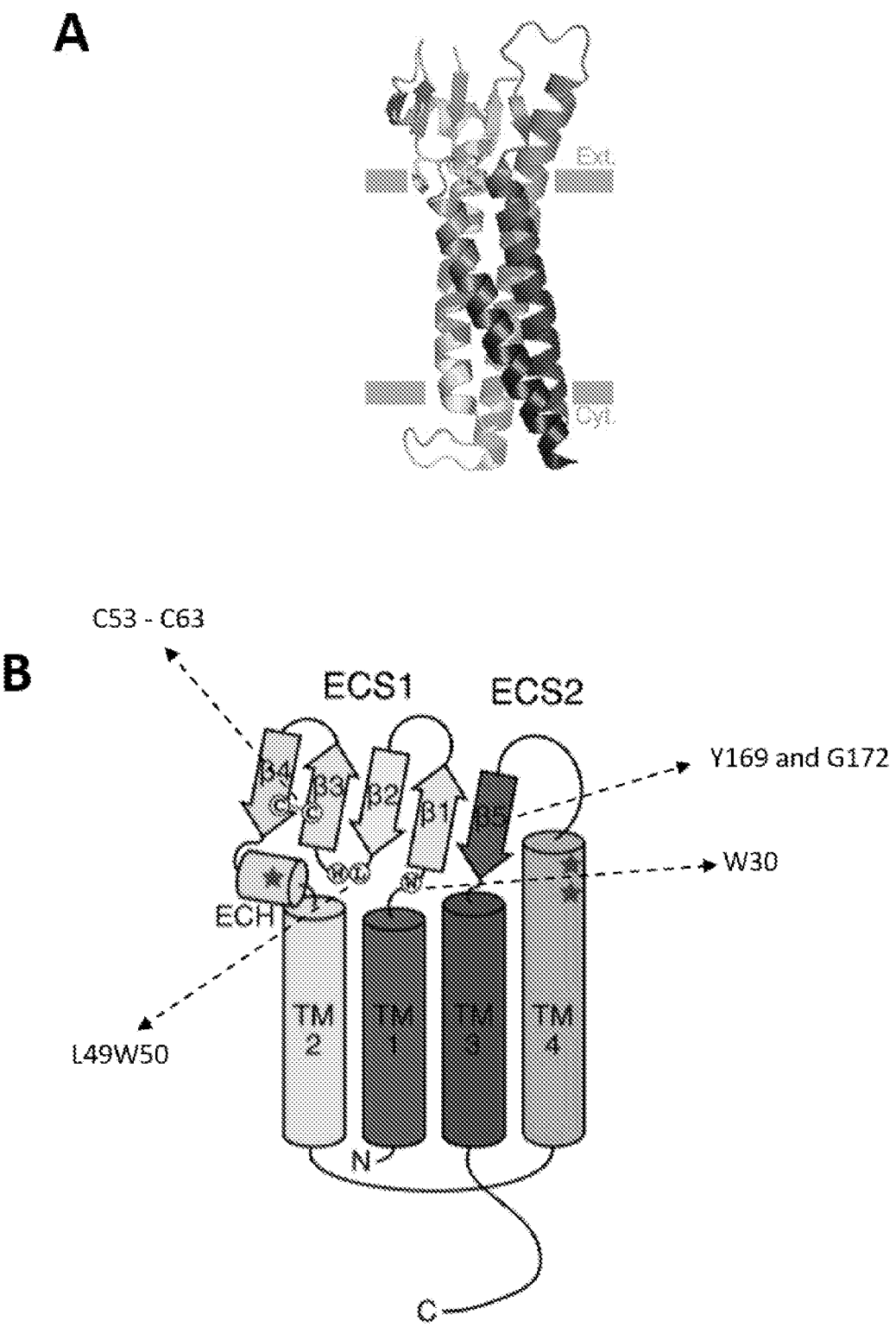
FIG. 20 illustrates the 3D and motif structures of claudin proteins.

The crystal structures of various claudin proteins have been resolved. As shown in FIG. 20 (adapted from Suzuki et al., *Ann. N.Y. Acad. Sci.*, 1397: 25-34), claudin proteins include four transmembrane segments, a short intracellular N-terminus, a large first extracellular loop (loop 1, or ECS1) that contains a consensus W-LW-C-C motif, a shorter second extracellular loop (loop 2, or ECS2), and an intracellular C-terminal tail. Loop 1 includes four β strands β1, β2, β3, and β4, and loops includes one β strand, β5.

The mutations of W30, L49 and W50 to alanine likely destabilized the conformation of loop 1. The mutation of C53 or C63 likely disrupted the disulfide bond between β3 and β4. R80 is likely important for maintaining the interaction between parallel claudin 18.2 molecules on the cell surface, or for stabilizing the conformation of loop 1. The remaining residues, including N45, Y46, G48, V54, R55, E56, S58, F60, and E62 (in the β3 to β4 loop), and Y169 and G172 (in β5), likely present the interface for binding to the antibodies tested here.

Example 14. Comparison of Humanized 4F11E2, 72C1B6A3 and 120B7B2 Antibodies with Benchmark 175D10 Claudin 18.2 Antibody Cell Based Binding To compare the humanized anti-claudin18.2 antibodies: 4F11E2 (HC N55E/LC S32A), 72C1B6A3(HC WT/LC S32A) and 120B7B2 (HC G57D S104A/LC S32A G97A) to benchmark antibody 175D10 (IMAB362), this example determined the cell-based binding in human claudin 18.2 expressed cells. CHO-K1 cells that stably expressed human CLD18A2 were sorted for high expressor and low expressor based on the level of human CLDN18.2 expression. Serially diluted anti-CLDN18.2 antibodies, starting from 100 nM, were incubated with $10^5$ cells for 30 minutes on ice. After being washed with FACS buffer, cells were then incubated with APC labeled secondary antibody for another 30 minutes on ice. Cells bound with antibodies were analyzed by FACS.

As shown in the FIG. 16, 4F11E2, 72C1B6A3 and 120B7B2 showed superior binding to 175D10 in both claudin 18.2 high and low CHO-K1 cells.

ADCC Assay

To further compare the ADCC effect of humanized anti-claudin18.2 antibodies: 4F11E2 (HC N55E/LC S32A), 72C1B6A3(HC WT/LC S32A) and 120B7B2 (HC G57D S104A/LC S32A G97A) to benchmark antibody 175D10 (IMAB362), this example performed a cell based ADCC assay. Briefly, NK92 cells were cocultured with claudin18.2 overexpressed 293 cells in the presence of different dose anti-claudin 18.2 antibodies. As shown in FIG. 17, 4F11E2, 72C1B6A3 and 120B7B2 showed superior ADCC potency to the 175D10 antibody.

Figure 18:
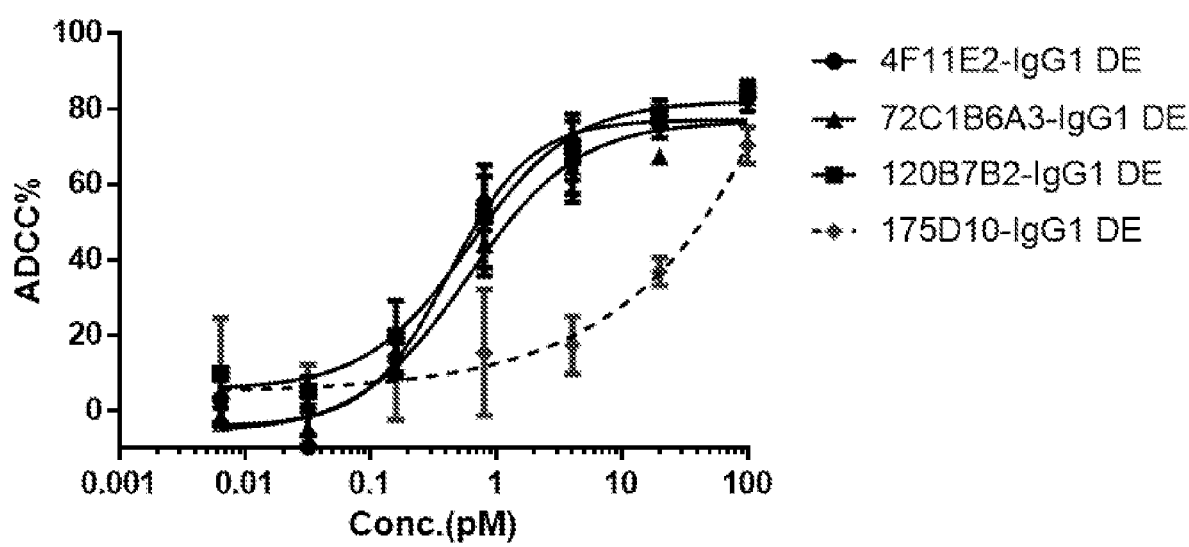
FIG. 18 shows that the S239D/I332E versions of the 4F11E2, 72C1B6A3 and 120B7B2 outperformed the 175D10 counterpart in the ADCC assays.

For certain therapeutic antibodies, enhanced ADCC may increase the therapeutic window to antibody-based target therapy. Enhanced ADCC may be achieved through engineering the Fc region such as with the S239D/I332E mutations. In a NK92 cell based ADCC assay, the 4H11E2, 72C1B6A3 and 120B7B2 antibodies with S239D/I332E mutations in the Fc region mediated stronger NK92-mediated cell killing of claudin 18.2 overexpressed 293 cells as compared to the control antibody 175D10 with the same S239D/I332E mutations (FIG. 18).

Antibody-Dependent Cellular Phagocytosis (ADCP)

The effect of anti-CLDN 18.2 mAbs on the tumor cell phagocytosis by macrophages was evaluated in an in vitro assay in which CLDN18.2 positive NUG-C4 cells were cocultured with human differentiated macrophages in the presence of different concentration of anti-CLDN18.2 mAbs. In short, CD14+ monocytes were purified from human peripheral blood mononuclear cells (PBMCs) and in vitro differentiated into mature macrophages for 6 days. The monocyte derived macrophages (MDMs) were collected and re-plated in 24-well dishes overnight as effector cells. NUG-C4 expressing CLDN 18.2-eGFP as target cells were added to MDMs at a ratio of 5 tumor cells per phagocyte in the presence of different concentrations of anti-CLDN18.2 mAbs. After 3 hours' incubation, non-phagocytosed target cells were washed away with PBS and the remaining phagocytes were collected and stained with macrophage marker CD14 followed by flow cytometry analysis. Phagocytosis index was calculated by quantitating the percent of GFP+ cells in CD14+ cells, normalized to that of IgG control.

Figure 19:
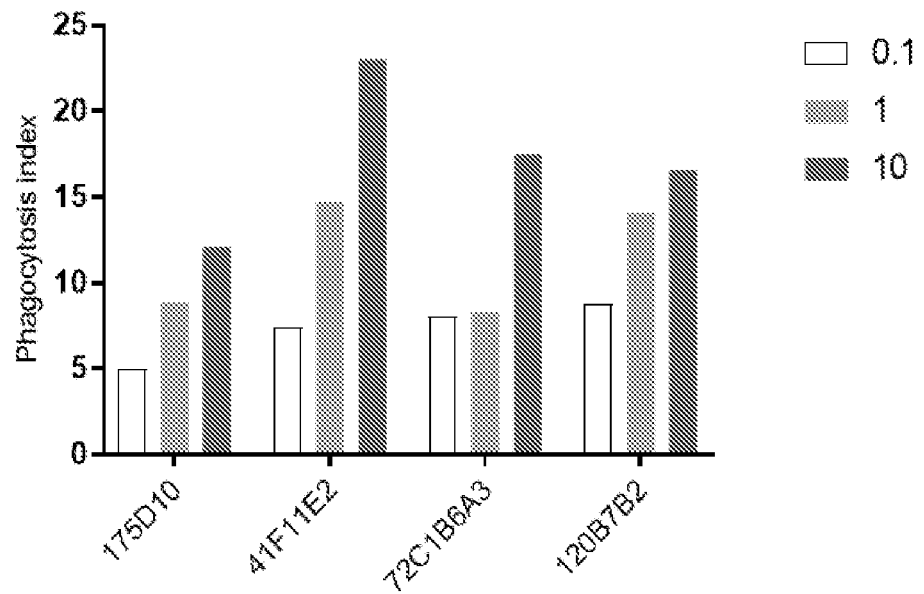
FIG. 19 shows that 4F11E2, 72C1B6A3 and 120B7B2 also had better ADCP effects than 175D10.
Figure 19:
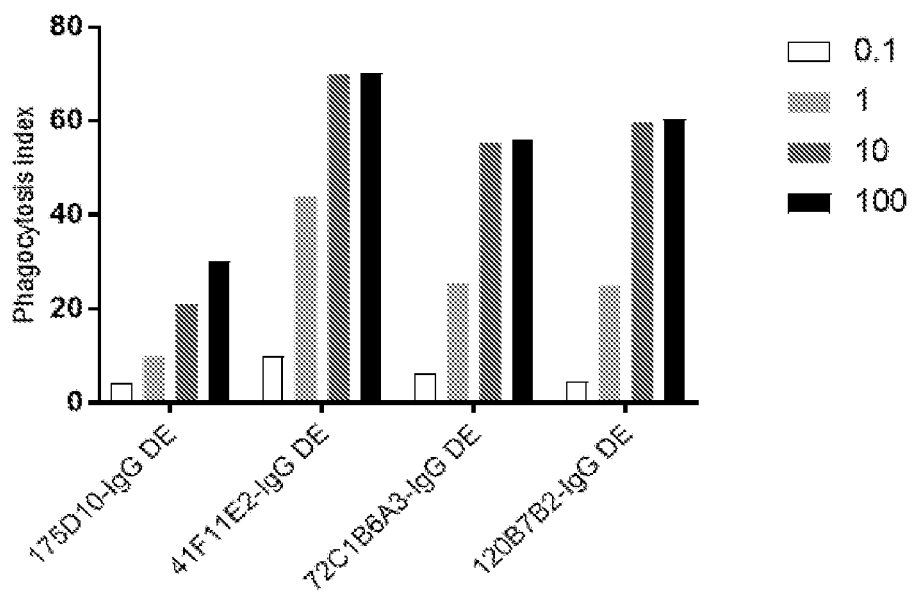

As shown in FIG. 19, all C18.2 mAbs significantly enhanced the phagocytosis of NUG-C4 cells in a concentration-dependent manner. In both wildtype IgG1 and S239D/I332E mutated IgG1 formats, 4H11E2, 72C1B6A3 and 120B7B2 antibodies showed stronger ADCP effect than the reference antibody 175D10.

Taken together, this example demonstrates that the newly developed 4F11E2, 72C1B6A3 and 120B7B2 antibodies had stronger cell-based binding and ADCC/ADCP potency than the reference antibody 175D10. It is contemplated that the improved properties of these new antibodies can be attributed to the higher binding specificity of these antibodies as compared to that of the reference antibody 175D10. For instance, 175D10's interaction with claudin 18.2 is strong across the spectrum in FIG. 15, which includes strong binding to D28, Q33, N38 and V43, and then G59 and V79. The new antibodies, 4F11E2, 72C1B6A3 and 120B7B2, by contrast, have higher specificity to W30 within the first half of the first extracellular domain, and higher specificity to G48 through E56 within the second half of the first extracellular domain. The new antibodies also have slightly stronger binding to Y46 which is also in the second half. Their binding to D28, Q33, N38, V43, G59 and V79 is considerably weaker, which likely contributed to the improved ADCC and ADCP of the new antibodies.

Example 15: pHAb Conjugation to Claudin 18.2 Antibodies

Internalization of CLDN18.2 bound anti-Claudin 18.2 antibodies was determined using pHAbReactive Dyes based internalization assay. pHAb Dyes are pH sensor dyes that have very low fluorescence at pH>7 and a dramatic increase in fluorescence as the pH of the solution becomes acidic. pHAb Dyes have excitation maxima (Ex) at 532 nm and emission maxima (Em) at 560 nm. pHAb Dye-conjugated antibodies can be used for monitoring receptor-mediated antibody internalization. When an antibody-pHAb Dye conjugate binds to its receptor on the cell membrane, it exhibits minimal fluorescence. However, upon receptor-mediated internalization, antibody-pHAb Dye conjugates traffic to the endosome and lysosomal vesicles where pH is acidic, causing the pHAb Dye to fluoresce. This fluorescence can be detected using various techniques, including cell imaging, flow cytometry and fluorescent plate-based readers with appropriate filters.

Experimental Protocol:
A. Antibodies Production
27 chimeric antibodies, 3 humanized antibodies and a control IgG1 were produced by transiently transfecting ExpiCHO cells and purified by Protein A affinity chromatography.

B. On-Bead Antibody Conjugation Using pHAb Thiol Reactive Dye
1. Gently shake or use an end-over-end mixer to uniformly resuspend the AmMag® Protein A Beads (LC00695). Keep the suspension uniform when making aliquots of beads.
2. Add 50 µl of bead slurry to a 1.5 ml microcentrifuge tube. Place the tube on the magnetic stand for 10 seconds.
3. Remove and discard the storage buffer.
4. Add 250 µl of PBS (pH7.4). Mix and place tube on the magnetic stand for 10 seconds. Remove and discard the buffer.
5. Add 1.0 ml of sample containing 100 µg of antibody to the beads.
6. Mix the sample for 60 minutes at room temperature. Keep the beads in suspension by mixing continuously.
7. Place the tube in the magnetic stand for 10 seconds. Remove the supernatant.
8. Add 250 µl of thiol conjugation buffer (10 mM phosphate buffer containing 1 mM EDTA, pH 7.0) and mix. Place the tube in the magnetic stand for 10 seconds. Remove and discard the buffer. Repeat this step for a total of two washes.
9. Add 100 µl of thiol conjugation buffer.
10. Add DTT to a final concentration of 2.5 mM.
11. Mix sample for 60 minutes at room temperature. Keep the beads in suspension by mixing continuously.
12. Place the tube in the magnetic stand for 10 seconds and discard the buffer.
13. Add 250 µl of thiol conjugation buffer and mix. Place the tube in the magnetic stand for 10 seconds. Remove and discard the buffer. Repeat this step for a total of two washes.
14. Add 100 µl of thiol conjugation buffer.
15. Quickly centrifuge the pHAb Thiol Reactive Dye (G9835) (i.e., 14,000×g in a tabletop centrifuge for 5-10 seconds) and dissolve at 10 mg/ml by adding 25 µl of 1:1 DMSO-water mix to 0.25 mg of dye. Mix by vortexing. It may take 1-3 minutes for the dye to dissolve completely. Make this solution just before use.
16. Add 1.2 µl of pHAb Thiol Reactive Dye for 100 µg of antibody to make a 20 molar excess of dye.
17. Mix for 60 minutes. Keep the beads in suspension by mixing continuously.
18. Place the tube in the magnetic stand for 10 seconds. Remove and discard the supernatant. 19. Add 250 µl of thiol conjugation buffer and mix. Place in the magnetic stand for 10 seconds. Remove and discard the bind/wash buffer (PBS.pH7.4).
20. Repeat Step 19 for a total of two washes.
21. Add 100 µl of elution buffer (0.1M Glycine, pH3.0) to the beads.
22. Mix for 5 minutes at room temperature.
23. Place the tube in the magnetic stand for 10 seconds. Remove eluted sample and transfer to a new microcentrifuge tube containing 5 µl of neutralization buffer (1M Tris-HCl, pH9.0).

The antibody concentration and dye-to-antibody ratio (DAR) for the tested antibodies are shown in Table 6.

TABLE 6

| Dye-to-antibody ratio (DAR) | |
| --- | --- |
| Clone | DAR |
| 64G11B4 | 2.5 |
| 65G8B8 | 4.2 |
| 56E8F10F4 | 3.2 |
| 44F6B11 | 3.0 |
| 15C2B7 | 3.0 |
| 20F1E10 | 2.7 |

TABLE 6-continued

Dye-to-antibody ratio (DAR)

| Clone | DAR |
|---|---|
| 58G2C2 | 3.1 |
| 101C4F12 | 2.4 |
| 103A10B2 | 3.5 |
| 78E8G9G6 | 2.3 |
| 10G7G11 | 3.1 |
| 12F1F4 | 2.4 |
| 78C10B6G4 | 2.9 |
| 119G11D9 | 3.2 |
| 113G12E5E6 | 2.9 |
| 116A8B7 | 2.6 |
| 105F7G12 | 2.8 |
| 84E9E12 | 2.8 |
| 103F4D4 | 2.1 |
| 110C12B6 | 2.8 |
| 85H12E8 | 3.8 |
| 103H2B4 | 2.7 |
| 103F6D3 | 3.1 |
| 113E12F7 | 3.9 |
| 111B12D11 | 2.7 |
| 111E7E2 | 3.5 |
| 100F4G12 | 3.0 |
| 4F11E2 HC N55E-LC S32A (BG2001-C) | 3.0 |
| 72C1B6A3 HC WT-LC S32A(BG2001-D) | 2.6 |
| 120B7B2 HC G57D&S104A-LC S32A&G97A (BG2001-E) | 3.0 |
| IMAB362 (Ref. Ab) | 3.3 |
| IgG (Control) | 2.9 |

Example 16: Screen for Claudin 18.2 Antibodies' Internalization

Stably transfected human CLDN18.2 MKN45 cells were harvested with 0.05% Trypsin/EDTA (Gibco, 25300-054) and plated in a 96-well black plate (Thermo Scientific #165305) at the density of 20 K per 90 µl per well. Plates were incubated for 20-24 h before treatment with pHAb labeled antibodies.

For internalization, pHAb conjugated claudin 18.2 antibodies were added to the cells at two concentrations (20 nM and 100 nM) and mixed gently for 1-2 min on a plate mixer and then incubated overnight to allow internalization (internalization can be detected in a few hours). Plates were read on a fluorescent plate reader at Ex/Em: 532 nm/560 nm on a Tecan Infinity M1000 Pro. To achieve higher sensitivity, media was replaced by PBS before reading the plate.

The results normalized by DAR are shown in Table 7. The internalization efficiencies of the tested antibodies were greater than the reference antibody IMAB362.

TABLE 7

Internalization Results

| | Fluorescence | |
|---|---|---|
| Clone | 20 nM | 100 nM |
| 64G11B4 | 24030 | 33742 |
| 65G8B8 | 15101 | 20466 |
| 56E8F10F4 | 19865 | 28672 |
| 44F6B11 | 18438 | 26089 |
| 15C2B7 | 19400 | 33174 |
| 20F1E10 | 21146 | 45093 |
| 58G2C2 | 18645 | 33059 |
| 101C4F12 | 15179 | 44394 |
| 103A10B2 | 11998 | 31328 |
| 78E8G9G6 | 26815 | 41148 |
| 10G7G11 | 9603 | 35549 |
| 12F1F4 | 29457 | 43854 |
| 78C10B6G4 | 16190 | 29146 |
| 119G11D9 | 21438 | 34049 |
| 113G12E5E6 | 11003 | 28896 |
| 116A8B7 | 21356 | 41720 |
| 105F7G12 | 14848 | 43122 |
| 84E9E12 | 18710 | 35080 |
| 103F4D4 | 31176 | 49098 |
| 110C12B6 | 19335 | 40139 |
| 85H12E8 | 19710 | 29070 |
| 103H2B4 | 23459 | 35834 |
| 103F6D3 | 23023 | 41266 |
| 113E12F7 | 13181 | 29861 |
| 111B12D11 | 15926 | 37384 |
| 111E7E2 | 12335 | 28040 |
| 100F4G12 | 17093 | 33537 |
| 4F11E2 HC N55E-LC S32A (BG2001-C) | 19008 | 28208 |
| 72C1B6A3 HC WT-LC S32A (BG2001-D) | 26203 | 36535 |
| 120B7B2 HC G57D&S104A-LC S32A&G97A (BG2001-E) | 19204 | 31321 |
| IMAB362 (Ref. Ab) | 7951 | 18907 |
| IgG (Control) | 854 | 2705 |

Example 17: EC50 of Internalization of Chimeric Claudin 18.2 Antibodies on CHO-Claudin 18.2 Cells Stably transfected human CLDN18.2 CHO cells were harvested with 0.05% Trypsin/EDTA (Gibco, 25300-054) and plated in a 96-well black plate (Thermo Scientific #165305) at the density of 10 K per 90 µl per well. Plates were incubated for 20-24 h before treatment with pHAb labeled antibodies.

For internalization, pHAb conjugated chimeric claudin 18.2 antibodies were added to the cells at different concentrations (100 nM, 30 nM, 10 nM, 3 nM, 1 nM, 0.3 nM, 0.1 nM, 0.03 nM and 0.01 nM) and mixed gently for 1-2 min on a plate mixer and then incubated overnight to allow internalization (internalization can be detected in a few hours). Plates were read on a fluorescent plate reader at Ex/Em: 532 nm/560 nm on a Tecan Infinity M1000 Pro. To achieve higher sensitivity, media was replaced by PBS before reading the plate.

Figure 21:
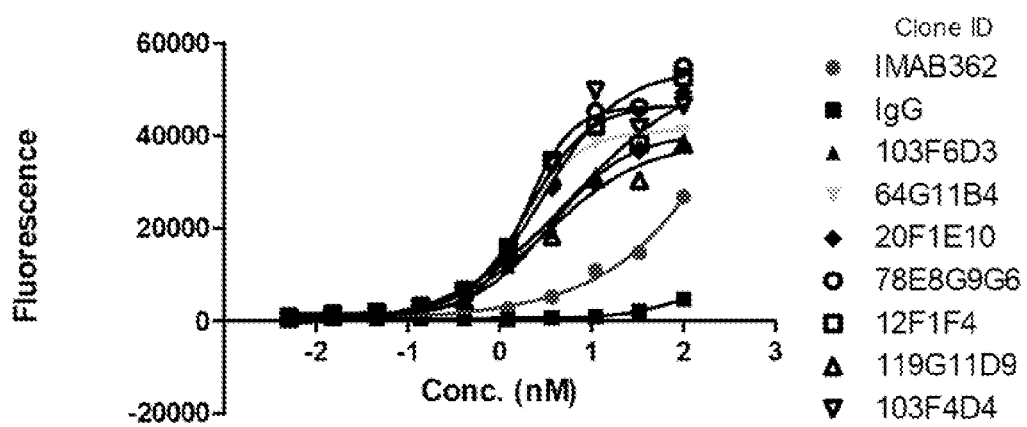
FIG. 21 shows the internalization results of tested chimeric antibodies as compared to reference antibody IMAB362 on CHO cells expressing claudin 18.2.

The results normalized with DAR are shown in the FIG. 21. Again, the internalization efficiencies of the tested antibodies were greater than the reference antibody IMAB362.

Example 18: EC50 of Internalization of Humanized Claudin 18.2 Antibodies on CHO-Claudin 18.2 Cells Stably transfected human CLDN18.2 CHO cells were harvested with 0.05% Trypsin/EDTA (Gibco, 25300-054) and plated in a 96-well black plate (Thermo Scientific #165305) at the density of 10 K per 90 µl per well. Plates were incubated for 20-24 h before treatment with pHAb labeled antibodies.

For internalization, pHAb conjugated humanized claudin 18.2 antibodies were added to the cells at different concentrations (100 nM, 30 nM, 10 nM, 3 nM, 1 nM, 0.3 nM, 0.1 nM, 0.03 nM and 0.01 nM) and mixed gently for 1-2 min on a plate mixer and then incubated overnight to allow internalization (internalization can be detected in a few hours). Plates were read on a fluorescent plate reader at Ex/Em: 532 nm/560 nm on a Tecan Infinity M1000 Pro. To achieve higher sensitivity, media was replaced by PBS before reading the plate.

Figure 22:
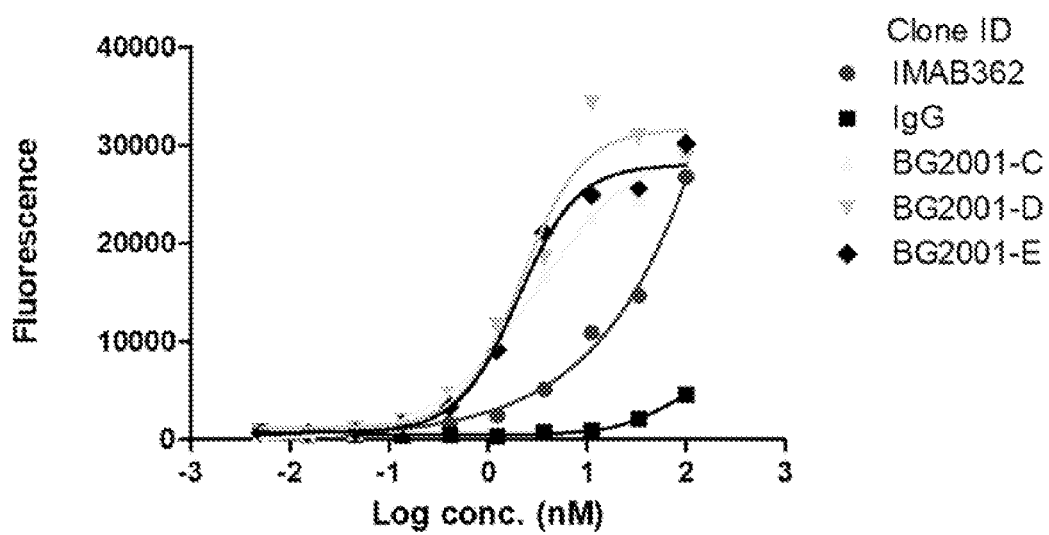
FIG. 22 shows the internalization results of tested humanized antibodies as compared to reference antibody IMAB362 on CHO cells expressing claudin 18.2.

The results normalized with DAR are shown in the FIG. 22, which shows that the internalization efficiencies of the tested antibodies were greater than the reference antibody IMAB362.

Example 19: EC50 of Internalization of Humanized Claudin 18.2 Antibodies on MKN45-Claudin 18.2 Cells Stably transfected human CLDN18.2 MKN45 cells were harvested with 0.05% Trypsin/EDTA (Gibco, 25300-054) and plated in a 96-well black plate (Thermo Scientific #165305) at the density of 10 K per 90 µl per well. Plates were incubated for 20-24 h before treatment with pHAb labeled antibodies.

For internalization, pHAb conjugated humanized claudin 18.2 antibodies were added to the cells at different concentrations (100 nM, 30 nM, 10 nM, 3 nM, 1 nM, 0.3 nM, 0.1 nM, 0.03 nM and 0.01 nM) and mixed gently for 1-2 min on a plate mixer and then incubated overnight to allow internalization (internalization can be detected in a few hours). Plates were read on a fluorescent plate reader at Ex/Em: 532 nm/560 nm on a Tecan Infinity M1000 Pro. To achieve higher sensitivity, media was replaced by PBS before reading the plate.

Figure 23:
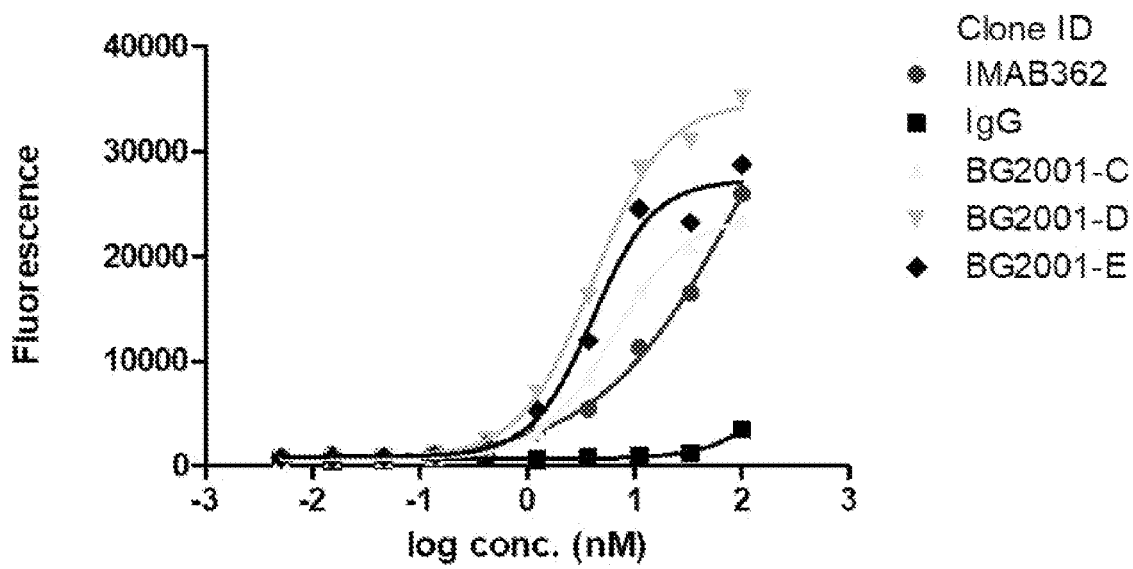
FIG. 23 shows the internalization results of tested humanized antibodies as compared to reference antibody IMAB362 on MKN45 cells expressing claudin 18.2.

The results normalized with DAR are shown in the FIG. 23, which shows that the internalization efficiencies of the tested antibodies were greater than the reference antibody IMAB362.

Example 20: Antibody Drug Conjugates

Each antibody was mixed with approximately three-fold TCEP and was stirred for 2 h at 37° C. The reaction system was quickly dropped over eight-fold for VC-MMAE and was incubated for 1 h on ice, and 20-fold excess of cysteine was added over the drug linker to extinguish the reaction. Finally, the ADC product was purified by elution through Sephadex G-25 equilibrated in PBS and concentrated by centrifugal ultrafiltration. The conjugate was filtered through a 0.2 µm filter under sterile conditions and stored at −80° C. for analysis and testing. Drug antibody ratio was analyzed by UV spectrometry, the monomer content by SEC-HPLC and free drug content by RP-HPLC. The (DAR) of vcMMAE conjugated antibodies are shown in Table 8.

TABLE 8

| DAR of vcMMAE conjugated antibodies | |
|---|---|
| Antibodies | DAR |
| 4F11E2 HC N55E-LC S32A | 3.76 |
| 72C1B6A3 HC WT-LC S32A | 3.93 |
| IMAB362 (Ref. Ab) | 4.00 |
| IgG1 (Control) | 3.81 |

Example 21: Relative Binding Affinities and Specificities of Anti-CLDN18.2 Naked Antibodies and Antibody Drug Conjugates This example determined the relative binding affinities and specificities of anti-CLDN18.2 naked antibodies and antibody drug conjugates by flow cytometry using CLDN18.2 positive and negative cell lines.

Cells from an exponentially growing culture were harvested with 0.05% Trypsin/EDTA (Gibco, 25300-054), and counted using a Neubauer counting chamber. Cells were centrifuged 5 min at 1,500 rpm (468×g), the supernatant was discarded and cells were resuspended in FACS buffer (PBS containing 2% FCS (Gibco, 10270-106) for analysis with toxin-conjugated antibodies, PBS containing 2% FCS and 2 mM EDTA for screening of CLDN18.2 reactive naked antibodies) at $2 \times 10^6$ cells/ml. 100 µl of the cell suspension per well (correspond to $2 \times 10^5$ cells/well) were transferred to a round bottom 96-well microtiter plate. After centrifugation for 1 min at 1500 rpm, supernatant was discarded and cells were resuspended in FACS buffer containing toxin-conjugated or naked antibodies at appropriate concentrations (up to 20 µg/ml for relative affinity measurement or 50 µg/ml for expression control) and incubated for 30-45 min at 4° C. (Table 8). The cells were centrifuged for 1 min at 1500 rpm and the supernatant was discarded. After the cells were washed three times with FACS buffer, they were resuspended in FACS buffer containing APC-conjugated anti-human IgG (Jackson Immuno Research, 109-136-170) or APC-conjugated goat-anti-mouse IgG (Jackson Immuno Research, 115-136-146) or Protein L-FITC (1 µg/ml, analysis of chim mAB294) and incubated for 30 min at 4° C. (Table 3). After incubation, 100 µl FACS buffer were added to each sample, the cells were centrifuged for 1 min at 1500 rpm and the supernatant was discarded. The washing step with FACS buffer was repeated twice. Finally, the cells were resuspended in 100 µl FACS buffer and binding was determined using a BD FACS Array Bioanalyzer.

Figure 24:
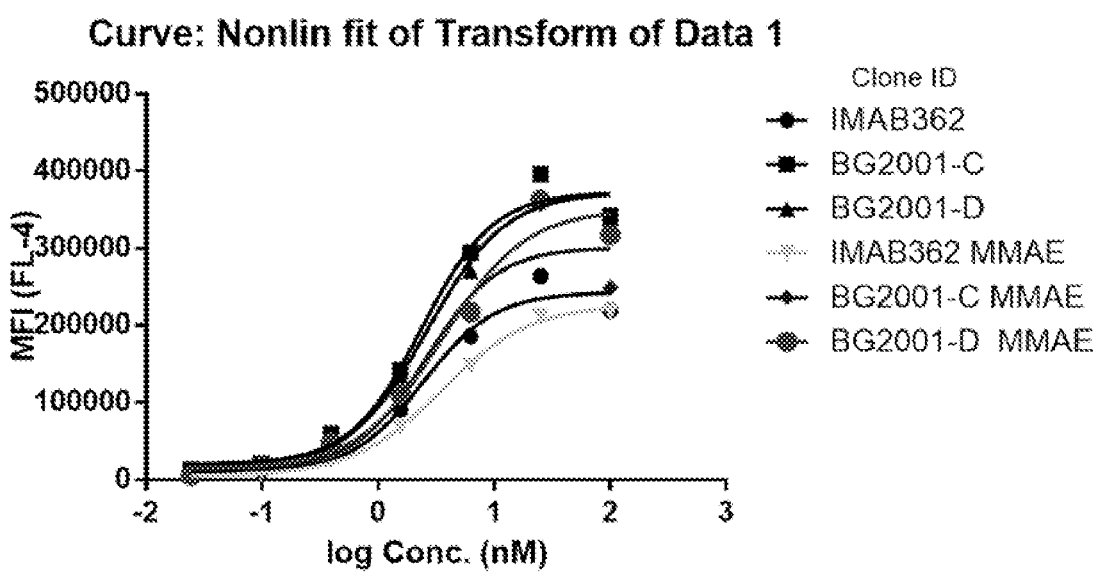
FIG. 24 shows the binding affinities of the antibodies and their drug conjugates.

It should be noted that toxin-conjugated and naked antibodies were applied at equal concentrations. The results are shown in FIG. 24.

Example 22: Cell Toxicity of Claudin 18.2 Humanized Antibodies with MMAE is More Potent than IMAB362 with MMAE in DAN-G, NUGC or SCG-7901 Transfectants Cells overexpressing human claudin 18.2 (DAN-G, NUGC or SCG-7901 transfectants) were harvested with 0.05% Trypsin/EDTA (Gibco, 25300-054), resuspended in cell culture medium and 50 µl of the cell suspension with the corresponding amount of cells were seeded per well in 96-well cell culture plates. After 24 h, toxin conjugated IMAB362 or control antibodies diluted in 50 µl medium at appropriate concentrations were added and cells were cultured for another 72 h. The effect of Claudin 18.2 humanized antibodies with MMAE on cell viability was determined using a CellTiter-Glo® Luminescent Cell Viability Assay (G7572).

CellTiter-Glo® Luminescent Cell Viability Assay (G7572) protocol used was as follows:

1. Prepare opaque-walled multiwell plates with mammalian cells in culture medium, 100 µl per well for 96-well plates or 25 µl per well for 384-well plates. Multiwell plates must be compatible with the luminometer used.

2. Prepare control wells containing medium without cells to obtain a value for background luminescence.

3. Add the test compound to experimental wells, and incubate according to culture protocol. 4. Equilibrate the plate and its contents at room temperature for approximately 30 minutes 5. Add a volume of CellTiter-Glo® Reagent equal to the volume of cell culture medium present in each well (e.g., add 100 µl of reagent to 100 µl of medium containing cells for a 96-well plate, or add 25 µl of reagent to 25 µl of medium containing cells for a 384-well plate).

6. Mix contents for 2 minutes on an orbital shaker to induce cell lysis.

7. Allow the plate to incubate at room temperature for 10 minutes to stabilize luminescent signal. Note: Uneven luminescent signal within standard plates can be caused by temperature gradients, uneven seeding of cells or edge effects in multiwell plates.

8. Record luminescence.

Figure 25A:
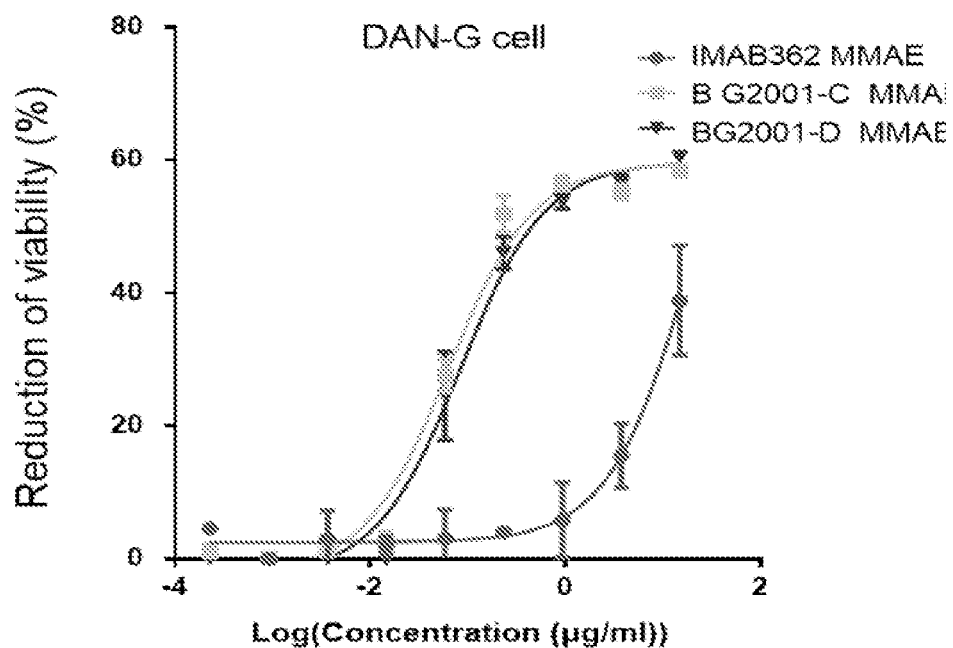
FIG. 25A-C show the cell toxicity of the tested antibody-MMAE conjugates upon internalization in DAN-G, NUGC or SCG-7901 transfectants.
Figure 25B:
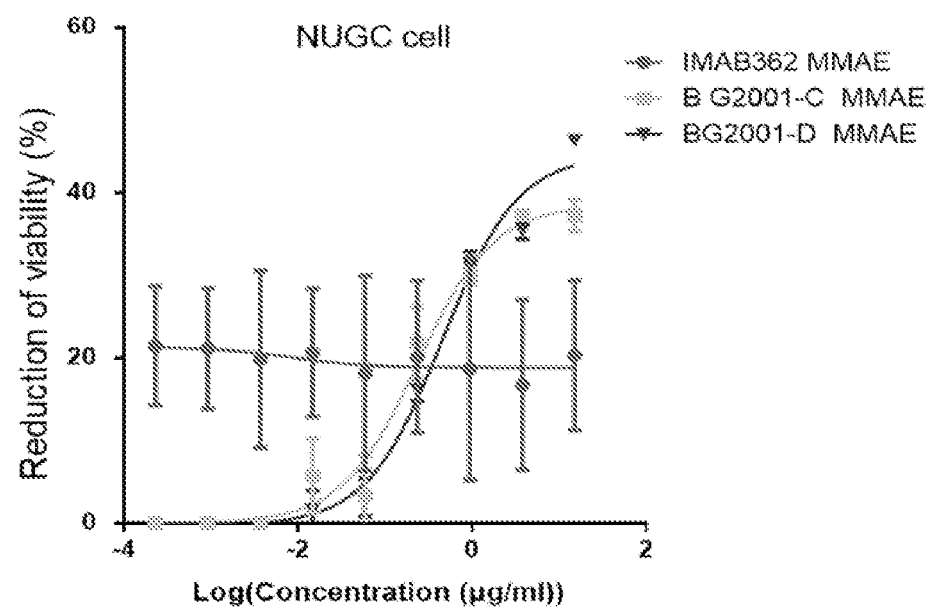
Figure 25C:
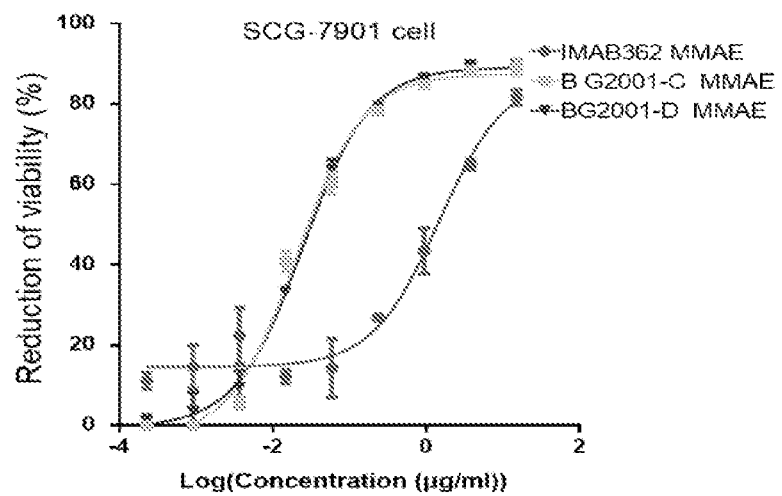

The testing results are shown in FIG. 25A-C. BG2001-C and BG2001-D both, when conjugated with MMAE, had greatly increased cytotoxicity as compared to the reference IMAB362-NMAE conjugate, in all tested cells. These results therefore demonstrate the improved ability of the presently disclosed antibodies in internalizing conjugated drugs.

Example 23: Cell Toxicity of Claudin 18.2 Humanized Antibodies with MMAE is More Potent than IMAB362 with MMAE in SNU620 Endogenously Expressing Human Claudin 18.2

Figure 26:
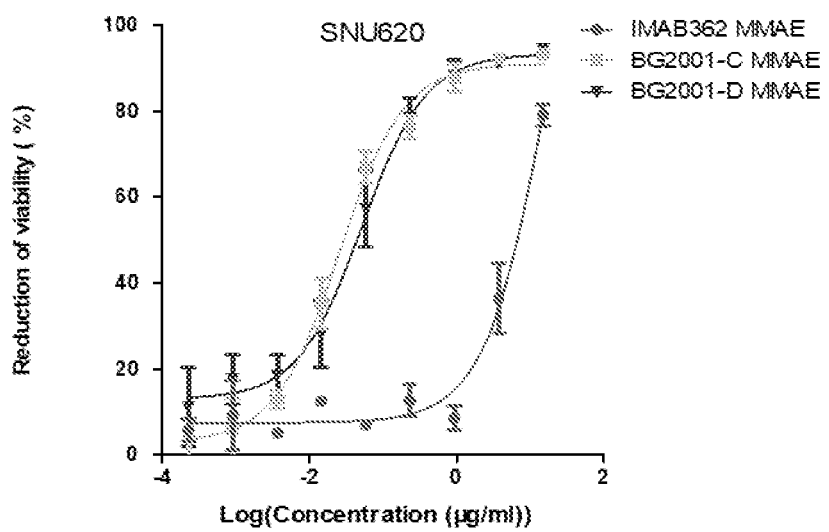
FIG. 26 shows the cell toxicity of the tested antibody-MMAE conjugates upon internalization in SNU620 endogenously expressing human claudin 18.2.

SNU620 cells were resuspended in cell culture medium and 50 µl of the cell suspension with the corresponding amount of cells were seeded per well in 96-well cell culture plates. After 24 h, toxin conjugated antibodies, including reference antibody IMAB362, diluted in 50 µl medium at appropriate concentrations were added and cells were cultured for another 72 h. The effect of Claudin 18.2 humanized antibodies with MMAE on cell viability was determined using a CellTiter-Glo® Luminescent Cell Viability Assay (G7572). As shown in FIG. 26, BG2001-C and BG2001-D both were greatly more effective in delivering the conjugated MMAE into the SNU620 cells as compared to the reference antibody IMAB362, a lead anti-claudin 18.2 antibody under clinical development.

Example 24: In Vivo Efficacy of the Antibody Drug Conjugates

This example tested the efficacy of one of the antibody-drug conjugates (ADC), as compared to the antibody alone (mAb), in reducing tumor growth in nude mice transplanted with human tumor cells.

0.1 mL ($5 \times 10^5$ cells) of human patient derived cells (mixed with Matrigel 1:1) were subcutaneously inoculated on the right back of each mouse. When the average tumor volume reached 60~80 mm$^3$, 30 mice were selected for treatment experiments.

Eighteen days following inoculation, 5 mice having a tumor size in the range of 330-520 mm$^3$ were selected for each treatment (1 mg/kg, 3 mg/mk, 10 mg/kg or 20 mg/kg ADC, QW) for three weeks. For comparison, antibody (mAb) only treatment was at 10 mg/kg (BIW).

Figure 27:
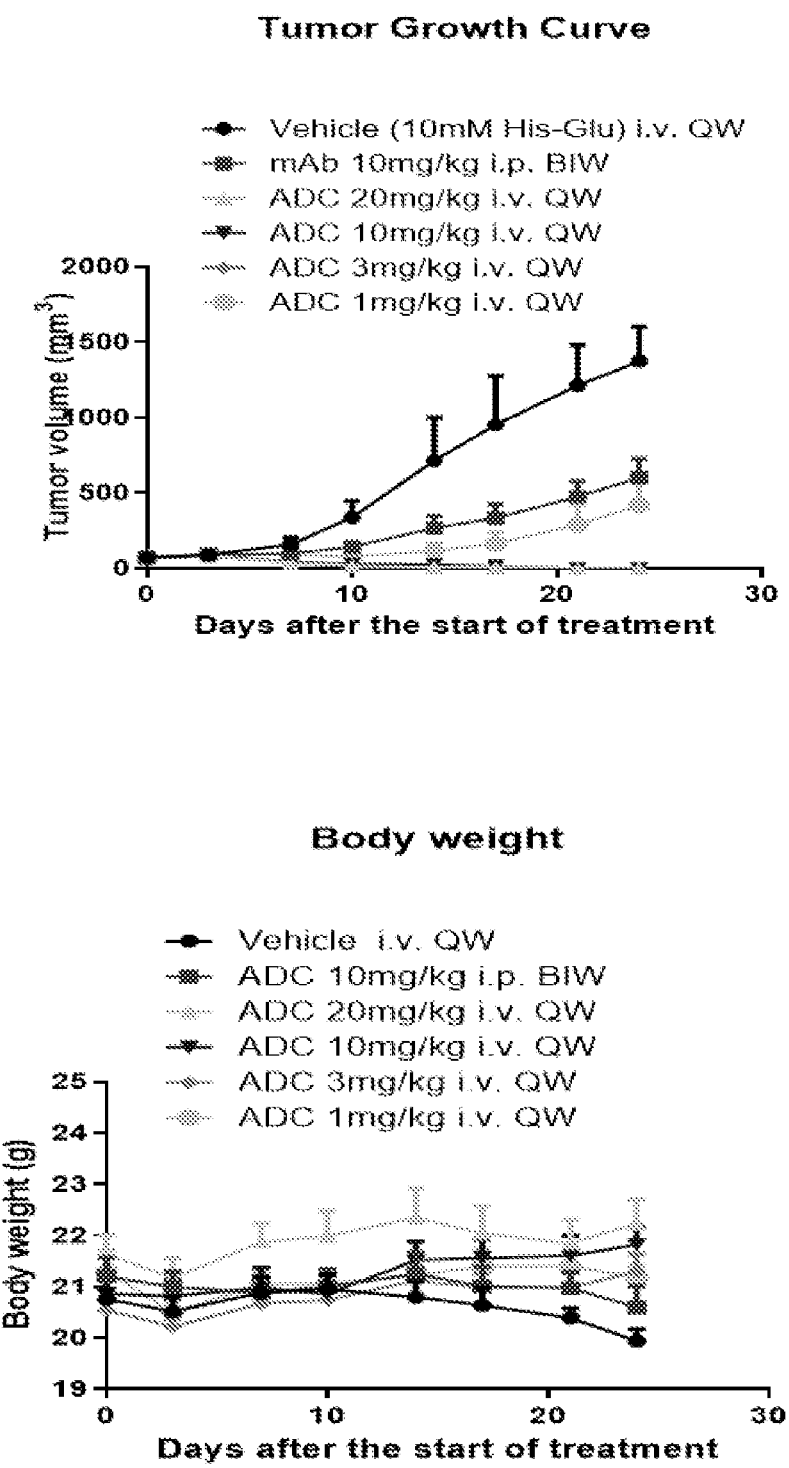
FIG. 27 compares antibody-drug conjugate with antibody alone in reducing tumor growth in test animals.
Figure 28:
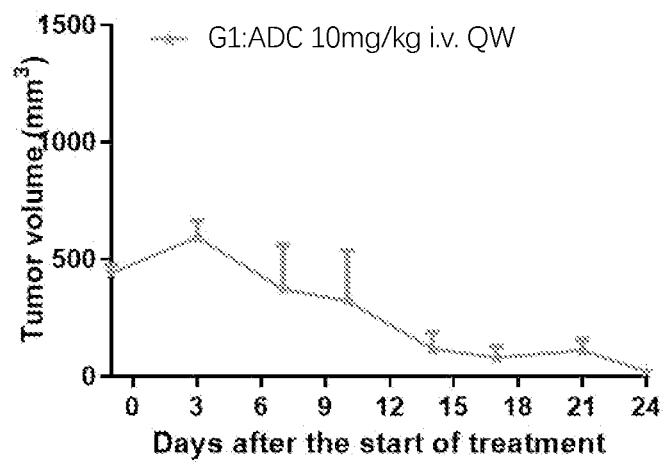
FIG. 28 shows the average or individual tumor reduction effects of the antibody-drug conjugate.
Figure 28:
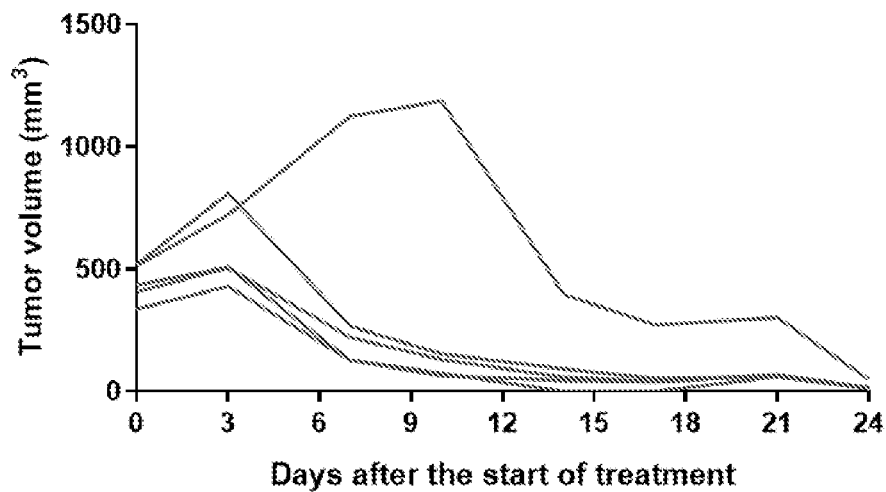

The results are presented in FIG. 27. ADC at both 10 mg/kg and 20 mg/kg completely inhibited tumor growth, without reducing the animals' body weights. FIG. 28 shows the average and individual tumor reduction effect in each animal. The tumor reduction effect of the ADC, therefore, is considerably greater than antibody alone.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

---

What is claimed is:

1. An antibody-drug conjugate, comprising a drug moiety covalently attached to an antibody or fragment thereof having binding specificity to a wild-type human claudin 18.2 protein, wherein the antibody or the fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, wherein (a) the CDRL1 comprises the amino acid sequence of SEQ ID NO:304, the CDRL2 comprises the amino acid sequence of SEQ ID NO:227, the CDRL3 comprises the amino acid sequence of SEQ ID NO:19, the CDRH1 comprises the amino acid sequence of SEQ ID NO:253,
the CDRH2 comprises the amino acid sequence of SEQ ID NO:306, and
the CDRH3 comprises the amino acid sequence of SEQ ID NO:307, or
(b) the CDRL1 comprises the amino acid sequence of SEQ ID NO:309,
the CDRL2 comprises the amino acid sequence of SEQ ID NO:227,
the CDRL3 comprises the amino acid sequence of SEQ ID NO:13,
the CDRH1 comprises the amino acid sequence of SEQ ID NO:246,
the CDRH2 comprises the amino acid sequence of SEQ ID NO:311, and
the CDRH3 comprises the amino acid sequence of SEQ ID NO:294, and
the drug moiety comprises monomethyl auristatin E (MMAE).

2. The antibody-drug conjugate of claim 1, wherein:
the CDRL1 comprises the amino acid sequence of SEQ ID NO:304,
the CDRL2 comprises the amino acid sequence of SEQ ID NO:227,
the CDRL3 comprises the amino acid sequence of SEQ ID NO:19,
the CDRH1 comprises the amino acid sequence of SEQ ID NO:253,
the CDRH2 comprises the amino acid sequence of SEQ ID NO:306, and
the CDRH3 comprises the amino acid sequence of SEQ ID NO:307.

3. The antibody-drug conjugate of claim 2, wherein the antibody or the fragment thereof comprises a light chain variable region comprising an amino acid sequence of SEQ ID NO:206 and a heavy chain variable region comprising an amino acid sequence of SEQ ID NO:205.

4. The antibody-drug conjugate of claim 1, wherein:
the CDRL1 comprises the amino acid sequence of SEQ ID NO:309,
the CDRL2 comprises the amino acid sequence of SEQ ID NO:227,
the CDRL3 comprises the amino acid sequence of SEQ ID NO:13,
the CDRH1 comprises the amino acid sequence of SEQ ID NO:246,
the CDRH2 comprises the amino acid sequence of SEQ ID NO:311, and
the CDRH3 comprises the amino acid sequence of SEQ ID NO:294.

5. The antibody-drug conjugate of claim 4, wherein the antibody or the fragment thereof comprises a light chain variable region comprising an amino acid sequence of SEQ ID NO:202 and a heavy chain variable region comprising an amino acid sequence of SEQ ID NO:197.

6. The antibody-drug conjugate of claim 1, wherein the drug moiety is attached to the antibody or fragment thereof through a linker.

7. The antibody-drug conjugate of claim 6, wherein the linker is hydrolyzable under acidic conditions.

8. The antibody-drug conjugate of claim 1, wherein the antibody or fragment thereof is humanized.

9. The antibody-drug conjugate of claim 1, wherein the antibody or fragment thereof comprises a heavy chain constant region.

10. The antibody-drug conjugate of claim 9, wherein the heavy chain constant region has domains derived from an IgG$_1$ molecule.

11. The antibody-drug conjugate of claim 10, wherein the heavy chain constant region comprises S239D/I332E mutations according to EU numbering.

12. The antibody-drug conjugate of claim 1, wherein the antibody or fragment thereof comprises a light chain constant region.

13. The antibody-drug conjugate of claim 12, wherein the light chain constant region comprises a constant kappa domain or a constant lambda domain.

14. The antibody-drug conjugate of claim 6, wherein the linker comprises valine-citrulline (Val-Cit), phenylalanine-lysine (Phe-Lys), maleimidocapronic-valine-citrulline-p-aminobenzyloxycarbonyl (mc-Val-Cit-PABA), sulfosuccinimidyl-4-[N-maleimidomethyl]cyclohexane-1-carboxylate (smcc), or maleimidocaproyl (mc).

15. The antibody-drug conjugate of claim 1, wherein a ratio of the drug moiety to the antibody or fragment thereof is from 1:1 to 20:1.

16. The antibody-drug conjugate of claim 1, wherein a ratio of the drug moiety to the antibody or fragment thereof is from 2:1 to 6:1.

17. The antibody-drug conjugate of claim 1, wherein a ratio of the drug moiety to the antibody or fragment thereof is about 2:1, 2.5:1, 3:1, 3.5:1, 4:1, 4.5:1, or 5:1.

18. An antibody-drug conjugate, comprising a drug moiety covalently attached to a humanized antibody having binding specificity to a wild-type human claudin 18.2 protein, wherein the antibody comprises:
(1) a light chain variable region comprising an amino acid sequence of SEQ ID NO:206 and a heavy chain variable region comprising an amino acid sequence of SEQ ID NO:205,
(2) a heavy chain constant region has domains derived from an IgG$_1$ molecule and S239D/I332E mutations according to EU numbering,
(3) a light chain constant region that comprises a constant kappa domain or a constant lambda domain;
the drug moiety comprises monomethyl auristatin E (MMAE);
wherein the drug moiety is attached to the antibody through a linker comprising maleimidocapronic-valine-citrulline-p-aminobenzyloxycarbonyl (mc-Val-Cit-PABA); and
wherein a ratio of the drug moiety to the antibody or fragment thereof is about 2:1, 2.5:1, 3:1, 3.5:1, 4:1, 4.5:1, or 5:1.

19. An antibody-drug conjugate, comprising a drug moiety covalently attached to a humanized antibody having binding specificity to a wild-type human claudin 18.2 protein, wherein the antibody comprises:
(1) a light chain variable region comprising an amino acid sequence of SEQ ID NO:202 and a heavy chain variable region comprising an amino acid sequence of SEQ ID NO:197,
(2) a heavy chain constant region has domains derived from an IgG$_1$ molecule and S239D/I332E mutations according to EU numbering,
(3) a light chain constant region that comprises a constant kappa domain or a constant lambda domain;
the drug moiety comprises monomethyl auristatin E (MMAE);

wherein the drug moiety is attached to the antibody through a linker comprising maleimidocapronic-valine-citrulline-p-aminobenzyloxycarbonyl (mc-Val-Cit-PABA); and wherein a ratio of the drug moiety to the antibody or fragment thereof is about 2:1, 2.5:1, 3:1, 3.5:1, 4:1, 4.5:1, or 5:1.

20. A pharmaceutical composition comprising:
(i) an antibody-drug conjugate that comprises a drug moiety covalently attached to an antibody or fragment thereof having binding specificity to a wild-type human claudin 18.2 protein, wherein the antibody or the fragment thereof comprises a light chain variable region comprising light chain complementarity determining regions CDRL1, CDRL2, and CDRL3 and a heavy chain variable region comprising heavy chain complementarity determining regions CDRH1, CDRH2, and CDRH3, wherein
   (a) the CDRL1 comprises the amino acid sequence of SEQ ID NO:304,
      the CDRL2 comprises the amino acid sequence of SEQ ID NO:227,
      the CDRL3 comprises the amino acid sequence of SEQ ID NO:19,
      the CDRH1 comprises the amino acid sequence of SEQ ID NO:253,
      the CDRH2 comprises the amino acid sequence of SEQ ID NO:306, and
      the CDRH3 comprises the amino acid sequence of SEQ ID NO:307; or
   (b) the CDRL1 comprises the amino acid sequence of SEQ ID NO:309,
      the CDRL2 comprises the amino acid sequence of SEQ ID NO:227,
      the CDRL3 comprises the amino acid sequence of SEQ ID NO:13,
      the CDRH1 comprises the amino acid sequence of SEQ ID NO:246,
      the CDRH2 comprises the amino acid sequence of SEQ ID NO:311, and
      the CDRH3 comprises the amino acid sequence of SEQ ID NO:294; and
   the drug moiety comprises monomethyl auristatin E (MMAE); and
(ii) a pharmaceutically acceptable carrier.

21. The pharmaceutical composition of claim 20, wherein the antibody-drug conjugate comprises a drug moiety covalently attached to a humanized antibody having binding specificity to a wild-type human claudin 18.2 protein, wherein the antibody comprises:
   (1) a light chain variable region comprising an amino acid sequence of SEQ ID NO:206 and a heavy chain variable region comprising an amino acid sequence of SEQ ID NO:205,
   (2) a heavy chain constant region has domains derived from an $IgG_1$ molecule and S239D/I332E mutations according to EU numbering,
   (3) a light chain constant region that comprises a constant kappa domain or a constant lambda domain;
   the drug moiety comprises monomethyl auristatin E (MMAE);
   wherein the drug moiety is attached to the antibody through a linker comprising maleimidocapronic-valine-citrulline-p-aminobenzyloxycarbonyl (mc-Val-Cit-PABA); and
   wherein a ratio of the drug moiety to the antibody or fragment thereof is about 2:1, 2.5:1, 3:1, 3.5:1, 4:1, 4.5:1, or 5:1.

22. The pharmaceutical composition of claim 20, wherein the antibody-drug conjugate comprises a drug moiety covalently attached to a humanized antibody having binding specificity to a wild-type human claudin 18.2 protein, wherein the antibody comprises:
   (1) a light chain variable region comprising an amino acid sequence of SEQ ID NO:202 and a heavy chain variable region comprising an amino acid sequence of SEQ ID NO:197,
   (2) a heavy chain constant region has domains derived from an $IgG_1$ molecule and S239D/I332E mutations according to EU numbering,
   (3) a light chain constant region that comprises a constant kappa domain or a constant lambda domain;
   the drug moiety comprises monomethyl auristatin E (MMAE);
   wherein the drug moiety is attached to the antibody through a linker comprising maleimidocapronic-valine-citrulline-p-aminobenzyloxycarbonyl (mc-Val-Cit-PABA); and
   wherein a ratio of the drug moiety to the antibody or fragment thereof is about 2:1, 2.5:1, 3:1, 3.5:1, 4:1, 4.5:1, or 5:1.

* * * * *

SEQUENCE LISTING

```
<160> NUMBER OF SEQ ID NOS: 314

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Gln Ser Leu Leu Asn Ser Gly Asn Gln Lys Asn Tyr
1               5                   10

<210> SEQ ID NO 2
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (4)..(4)
<223> OTHER INFORMATION: Empty

<400> SEQUENCE: 2
```

Trp Ala Ser Xaa
1

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gln Asn Gly Tyr Tyr Phe Pro Phe Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Tyr Thr Phe Thr Gly Tyr Ile
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Ile Asn Pro Tyr Asn Asp Gly Thr
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Ala Arg Ala Tyr Phe Gly Asn Ser Phe Ala Tyr
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (4)..(4)
<223> OTHER INFORMATION: Empty

<400> SEQUENCE: 7

Arg Ala Ser Xaa
1

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gln Asn Asp Tyr Ile Tyr Pro Tyr Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gly Tyr Thr Phe Thr Thr Tyr Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Phe His Pro Tyr Asn Asp Asp Thr
1               5

<210> SEQ ID NO 11
<211> LENGTH: 13
<212> TYPE: PRT
<213> ORGANISM: Artificial Sequence
<220> FEATURE:
<223> OTHER INFORMATION: Synthetic

<400> SEQUENCE: 11

Ala Arg Arg Ala Tyr Gly Tyr Pro Tyr Ala Met Asp Tyr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Ser Leu Leu Asn Ser Gly Asn Arg Lys Asn Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Gln Asn Ala Tyr Ser Tyr Pro Phe Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic

```
<400> SEQUENCE: 14

Gly Phe Thr Phe Ser Thr Phe Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Ile Thr Ser Gly Asn Ser Pro Ile
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic

<400> SEQUENCE: 16

Ala Arg Ser Ser Tyr Tyr Gly Asn Ser Met Asp Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic

<400> SEQUENCE: 17

Gln Ser Leu Leu Asn Ala Gly Asn Gln Lys Asn Tyr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Gln Ser Leu Leu Glu Ser Gly Asn Gln Lys Asn Tyr
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Gln Asn Ala Tyr Tyr Phe Pro Phe Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20
```

```
Gln Glu Gly Tyr Tyr Phe Pro Phe Thr
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Ile Asn Pro Tyr Asn Asp Asp Thr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Ala Arg Ala Tyr Phe Gly Asn Ala Phe Ala Tyr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Gln Ser Leu Leu Glu Ser Gly Asn Arg Lys Asn Tyr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Gln Ser Leu Leu Asn Ala Gly Asn Arg Lys Asn Tyr
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Ile Thr Ser Gly Gln Ser Pro Ile
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26
```

Ile Thr Ser Gly Glu Ser Pro Ile
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Ala Arg Ser Ser Tyr Tyr Gly Gln Ser Met Asp Tyr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Ala Arg Ser Ser Tyr Tyr Gly Glu Ser Met Asp Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Ala Arg Ser Ser Tyr Tyr Gly Asn Ala Met Asp Tyr
1               5                   10

<210> SEQ ID NO 30
<211> LENGTH: 261
<212> TYPE: PRT
<213> ORGANISM: Artificial Sequence
<220> FEATURE:
<223> OTHER INFORMATION: Synthetic

<400> SEQUENCE: 30

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

```
Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
            165                 170                 175

Val Gly Trp Val Ala Gly Gly Leu Thr Leu Ile Gly Val Met Met
            180                 185                 190

Cys Ile Ala Cys Arg Gly Leu Ala Pro Glu Glu Thr Asn Tyr Lys Ala
            195                 200                 205

Val Ser Tyr His Ala Ser His Ser Val Ala Tyr Lys Pro Gly Gly
        210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
            245                 250                 255

Lys His Asp Tyr Val
            260

<210> SEQ ID NO 31
<211> LENGTH: 12
<212> TYPE: PRT
<213> ORGANISM: Artificial Sequence
<220> FEATURE:
<223> OTHER INFORMATION: Synthetic

<400> SEQUENCE: 31

Gln Ser Leu Leu Asn Ser Gly Asn Gln Arg Asn Tyr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Gln Ser Leu Leu Asn Ser Gly Asn Leu Lys Asn Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Gln Ser Leu Leu Asn Gly Gly Asn Gln Lys Asn Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Gln Ser Leu Leu Asn Ser Gly Asn Gln Lys Lys Tyr
1               5                   10

<210> SEQ ID NO 35
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 35

Gln Ser Leu Phe Asn Ser Gly Asn Gln Arg Asn Tyr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic

<400> SEQUENCE: 36

Met Ser Leu Phe Asn Ser Gly Asn Gln Lys Ser Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Gln Ser Leu Phe Asn Ser Gly Asn Gln Lys Asn Tyr
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic

<400> SEQUENCE: 38

Gln Ser Val Phe Asn Ser Gly Asn Gln Lys Asn Tyr
1               5                   10

<210> SEQ ID NO 39
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (4)..(4)
<223> OTHER INFORMATION: Empty

<400> SEQUENCE: 39

Gly Ala Ser Xaa
1

<210> SEQ ID NO 40
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (4)..(4)
<223> OTHER INFORMATION: Empty

<400> SEQUENCE: 40
```

Trp Ala Phe Xaa
1

<210> SEQ ID NO 41
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (4)..(4)
<223> OTHER INFORMATION: Empty

<400> SEQUENCE: 41

Trp Ser Ser Xaa
1

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Gln Asn Asp Tyr Phe Tyr Pro Phe Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic

<400> SEQUENCE: 43

Gln Asn Val Tyr Ile Tyr Pro Phe Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Gln Asn Asp Tyr Tyr Phe Pro Phe Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Gln Asn Asp Leu Tyr Tyr Pro Trp Thr
1               5

<210> SEQ ID NO 46
<211> LENGTH: 9
<212> TYPE: PRT
<213> ORGANISM: Artificial Sequence
<220> FEATURE:

```
<223> OTHER INFORMATION: Synthetic

<400> SEQUENCE: 46

Gln Asn Gly Tyr Ser Tyr Pro Phe Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Gln Asn Asn Tyr Tyr Phe Pro Leu Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Asn Val Tyr Ser Tyr Pro Leu Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Gln Asn Ser Tyr Ser Tyr Pro Phe Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Gln Asn Asn Phe Ile Tyr Pro Leu Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

His Asn Asp Tyr Ile Tyr Pro Leu Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic
```

<400> SEQUENCE: 52

Gln Asn Asn Tyr Tyr Tyr Pro Phe Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic

<400> SEQUENCE: 53

Gln Asn Ala Tyr Tyr Tyr Pro Leu Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Gln Asn Ala Tyr Phe Tyr Pro Cys Thr
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Gln Asn Asp Tyr Tyr Phe Pro Leu Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Gln Asn Ala Tyr Phe Tyr Pro Phe Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic

<400> SEQUENCE: 57

Gln Asn Asn Tyr Phe Tyr Pro Leu Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic

```
<400> SEQUENCE: 58

Gln Asn Asn Tyr Ile Tyr Pro Leu Ala
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic

<400> SEQUENCE: 59

Gly Tyr Ala Phe Thr Asn Tyr Leu
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Gly Phe Ser Leu Thr Ser Tyr Gly
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic

<400> SEQUENCE: 61

Gly Phe Thr Phe Asn Ser Phe Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic

<400> SEQUENCE: 62

Gly Phe Thr Phe Asn Thr Asn Ala
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic

<400> SEQUENCE: 63

Gly Tyr Thr Phe Pro Thr Tyr Ser
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic

<400> SEQUENCE: 64
```

```
Gly Phe Thr Phe Ser Asn Tyr Gly
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic

<400> SEQUENCE: 65

Gly Tyr Thr Phe Thr Asn Tyr Gly
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic

<400> SEQUENCE: 66

Gly Tyr Thr Phe Thr Lys Tyr Gly
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic

<400> SEQUENCE: 67

Gly Phe Ser Leu Ser Ser Tyr Gly
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Leu Ser Leu Thr Ser Phe Gly
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic

<400> SEQUENCE: 69

Gly Phe Ser Leu Ile Ser Tyr Gly
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70
```

```
Gly Phe Ser Leu Asn Thr Tyr Gly
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Gly Phe Ser Leu Ile Asn Tyr Gly
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Gly Tyr Thr Phe Thr Gly Phe Leu
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic

<400> SEQUENCE: 73

Asp Phe Ser Leu Thr Lys Tyr Gly
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Gly Tyr Ser Ile Thr Ser Gly Tyr Phe
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

Gly Phe Ser Leu Ser Asn Tyr Gly
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Tyr Ser Phe Thr Asn Phe Leu
```

```
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic

<400> SEQUENCE: 77

Ile Asn Pro Gly Asn Gly Gly Ser
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic

<400> SEQUENCE: 78

Ile Trp Gly Asp Gly Asn Thr
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic

<400> SEQUENCE: 79

Ile Ser Gly Gly Ser Asn Thr Ile
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Ile Arg Ser Lys Ser Asn Asn Tyr Ala Thr
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Ile Asn Pro Gly Asn Gly Gly Ser Asn
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

Ile Asn Pro Ser Thr Ile Tyr Thr
1               5
```

```
<210> SEQ ID NO 83
<211> LENGTH: 8
<212> TYPE: PRT
<213> ORGANISM: Artificial Sequence
<220> FEATURE:
<223> OTHER INFORMATION: Synthetic

<400> SEQUENCE: 83

Phe Ser Tyr Gly Asp Ser His Asn
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Ile Asn Ala Asn Thr Gly Glu Pro
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic

<400> SEQUENCE: 85

Ile Ser Thr Asn Thr Gly Glu Pro
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Asn Pro Gly Arg Ser Gly Thr
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic

<400> SEQUENCE: 87

Ile Trp Ala Gly Gly Ser Thr
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic

<400> SEQUENCE: 88

Ile Trp Ala Gly Gly Arg Thr
1               5
```

<210> SEQ ID NO 89
<211> LENGTH: 7
<212> TYPE: PRT
<213> ORGANISM: Artificial Sequence
<220> FEATURE:
<223> OTHER INFORMATION: Synthetic

<400> SEQUENCE: 89

Met Leu Ser Asp Gly Asn Thr
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic

<400> SEQUENCE: 90

Ile Arg Gly Asp Gly Asn Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic

<400> SEQUENCE: 91

Ile Trp Thr Gly Gly Asn Thr
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Ile Ser Tyr Asp Gly Ser Asn
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic

<400> SEQUENCE: 93

Ile Trp Ala Gly Gly Asn Thr
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Ile Asn Pro Thr Asn Gly Arg Thr
1               5

```
<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Ile Asn Pro Asn Thr Ile Tyr Thr
1               5

<210> SEQ ID NO 96
<211> LENGTH: 11
<212> TYPE: PRT
<213> ORGANISM: Artificial Sequence
<220> FEATURE:
<223> OTHER INFORMATION: Synthetic

<400> SEQUENCE: 96

Ala Arg Ile Tyr Tyr Gly Asn Ser Phe Ala Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Ala Lys Gln Gly Leu Tyr Gly His Ala Met Asp Tyr
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic

<400> SEQUENCE: 98

Thr Arg Leu Ala Leu Gly Asn Ala Met Asp Tyr
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Synthetic

<400> SEQUENCE: 99

Val Ser Gly Ala Tyr Tyr Gly Asn Ser Lys Ala Phe Asp Tyr
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic

<400> SEQUENCE: 100

Ala Arg Glu Gly Tyr Gly Arg Gly Asn Ala Met Asp Tyr
1               5                   10

<210> SEQ ID NO 101
```

<211> LENGTH: 11
<212> TYPE: PRT
<213> ORGANISM: Artificial Sequence
<220> FEATURE:
<223> OTHER INFORMATION: Synthetic

<400> SEQUENCE: 101

Ala Arg Phe Gly Arg Gly Asn Thr Met Asp Tyr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic

<400> SEQUENCE: 102

Ala Arg Leu Thr Arg Gly Asn Ser Phe Asp Tyr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic

<400> SEQUENCE: 103

Ala Arg Leu Val Arg Gly Asn Ser Phe Asp Phe
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

Ala Arg Thr Arg Tyr Gly Gly Asn Ala Met Asp Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic

<400> SEQUENCE: 105

Ala Arg Ser Leu Tyr Gly Asn Ser Leu Asp Ser
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic

<400> SEQUENCE: 106

Ala Arg Ser Leu Tyr Gly Asn Ser Phe Asp Tyr
1               5                   10

<210> SEQ ID NO 107
<211> LENGTH: 12

```
<212> TYPE: PRT
<213> ORGANISM: Artificial Sequence
<220> FEATURE:
<223> OTHER INFORMATION: Synthetic

<400> SEQUENCE: 107

Ala Arg Asp Arg Tyr Gly Gly Asn Ser Leu Asp Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic

<400> SEQUENCE: 108

Ala Arg His Lys Ala Tyr Gly Asn Ala Met Asp Tyr
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic

<400> SEQUENCE: 109

Ala Lys Val Gly Arg Gly Asn Ala Met Asp His
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic

<400> SEQUENCE: 110

Ala Arg Leu Asp Tyr Gly Asn Ala Met Asp Tyr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic

<400> SEQUENCE: 111

Ala Arg Asn Gly Tyr Tyr Gly Asn Ala Met Asp Tyr
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Synthetic

<400> SEQUENCE: 112

Gly Arg Leu Asp Tyr Gly Asn Ala Met Asp Tyr
1               5                   10

<210> SEQ ID NO 113
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 113

Ala Ser Phe Arg Phe Phe Ala Tyr
1               5

<210> SEQ ID NO 114
<211> LENGTH: 13
<212> TYPE: PRT
<213> ORGANISM: Artificial Sequence
<220> FEATURE:
<223> OTHER INFORMATION: Synthetic

<400> SEQUENCE: 114

Ala Arg His Gly Tyr Gly Lys Gly Asn Ala Met Asp Asn
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic

<400> SEQUENCE: 115

Ala Arg Ile Tyr Tyr Gly Asn Ser Met Asp Tyr
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic

<400> SEQUENCE: 116

Ala Arg Ser Leu Tyr Gly Asn Ser Phe Asp His
1               5                   10

<210> SEQ ID NO 117
<211> LENGTH: 113
<212> TYPE: PRT
<213> ORGANISM: Artificial Sequence
<220> FEATURE:
<223> OTHER INFORMATION: Synthetic

<400> SEQUENCE: 117

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Asp Asp Leu Ala Val Tyr Tyr Cys Gln Asn
                85                  90                  95

Asp Tyr Phe Tyr Pro Phe Thr Phe Gly Ala Gly Thr Asn Leu Glu Leu
            100                 105                 110
```

Lys

<210> SEQ ID NO 118
<211> LENGTH: 113
<212> TYPE: PRT
<213> ORGANISM: Artificial Sequence
<220> FEATURE:
<223> OTHER INFORMATION: Synthetic

<400> SEQUENCE: 118

```
Asp Ile Met Met Thr Gln Ser Pro Ser Ser Leu Thr Val Thr Thr Gly
1               5                   10                  15
Glu Lys Val Thr Leu Thr Cys Lys Ser Ser Gln Ser Leu Leu Asn Ser
            20                  25                  30
Gly Asn Leu Lys Asn Tyr Leu Thr Trp Tyr Gln Gln Lys Pro Gly His
        35                  40                  45
Pro Pro Lys Leu Leu Ile Tyr Trp Ala Ser Thr Arg Glu Ser Gly Val
    50                  55                  60
Pro Val Arg Phe Thr Gly Ser Gly Ser Gly Thr Asp Phe Thr Leu Thr
65                  70                  75                  80
Ile Ser Ser Val Gln Ala Glu Asp Leu Thr Val Tyr Tyr Cys Gln Asn
                85                  90                  95
Val Tyr Ile Tyr Pro Phe Thr Phe Gly Ser Gly Thr Lys Leu Glu Met
                100                 105                 110
Arg
```

<210> SEQ ID NO 119
<211> LENGTH: 113
<212> TYPE: PRT
<213> ORGANISM: Artificial Sequence
<220> FEATURE:
<223> OTHER INFORMATION: Synthetic

<400> SEQUENCE: 119

```
Asp Ile Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Tyr Phe Thr Leu Thr
65                  70                  75                  80
Ile Ser Ser Val Gln Ala Ala Asp Leu Ala Val Tyr Tyr Cys Gln Asn
                85                  90                  95
Asp Tyr Tyr Phe Pro Phe Thr Phe Gly Ser Gly Thr Lys Leu Glu Ile
                100                 105                 110
Lys
```

<210> SEQ ID NO 120
<211> LENGTH: 113
<212> TYPE: PRT
<213> ORGANISM: Artificial Sequence
<220> FEATURE:
<223> OTHER INFORMATION: Synthetic

<400> SEQUENCE: 120

```
Asp Thr Val Met Thr Gln Phe Pro Ser Ser Leu Ser Val Ser Ala Gly
```

```
                1               5                  10                  15
              Glu Lys Val Thr Met Ser Cys Lys Ser Ser Gln Ser Leu Leu Asn Gly
                              20                  25                  30

Gly Asn Gln Lys Asn Tyr Leu Ala Trp Tyr Gln Gln Lys Pro Gly Gln
                              35                  40                  45

Pro Pro Lys Leu Leu Ile Tyr Gly Ala Ser Thr Arg Glu Ser Gly Val
                      50                  55                  60

Pro Asp Arg Phe Thr Gly Ser Gly Ser Gly Thr Asp Phe Thr Leu Thr
              65                  70                  75                  80

Ile Ser Ser Val Gln Ala Glu Asp Leu Ala Val Tyr Tyr Cys Gln Asn
                              85                  90                  95

Asp Leu Tyr Tyr Pro Trp Thr Phe Gly Gly Gly Thr Lys Leu Glu Phe
                              100                 105                 110

Lys

<210> SEQ ID NO 121
<211> LENGTH: 113
<212> TYPE: PRT
<213> ORGANISM: Artificial Sequence
<220> FEATURE:
<223> OTHER INFORMATION: Synthetic

<400> SEQUENCE: 121

Asp Ile Val Met Thr Gln Ser Pro Ser Ser Leu Thr Val Thr Ala Gly
              1               5                  10                  15

Glu Lys Val Ile Met Ser Cys Lys Ser Asn Gln Ser Leu Leu Asn Ser
                              20                  25                  30

Gly Asn Gln Lys Lys Tyr Leu Thr Trp Tyr Gln Gln Lys Pro Gly Gln
                              35                  40                  45

Ser Pro Lys Leu Leu Ile Tyr Trp Ala Ser Thr Arg Glu Ser Gly Val
                      50                  55                  60

Pro Asp Arg Phe Thr Gly Ser Glu Ser Gly Thr Asp Phe Thr Leu Thr
              65                  70                  75                  80

Ile Ser Ser Val Arg Ala Glu Asp Leu Ala Val Tyr Tyr Cys Gln Asn
                              85                  90                  95

Gly Tyr Ser Tyr Pro Phe Thr Phe Gly Ser Gly Thr Lys Leu Glu Met
                              100                 105                 110

Lys

<210> SEQ ID NO 122
<211> LENGTH: 113
<212> TYPE: PRT
<213> ORGANISM: Artificial Sequence
<220> FEATURE:
<223> OTHER INFORMATION: Synthetic

<400> SEQUENCE: 122

Asp Ile Val Met Thr Gln Ser Pro Ser Ser Leu Thr Val Thr Ala Gly
              1               5                  10                  15

Gly Lys Val Thr Val Ser Cys Lys Ser Ser Gln Ser Leu Leu Asn Ser
                              20                  25                  30

Gly Asn Gln Lys Asn Tyr Leu Trp Tyr Gln Gln Lys Pro Gly Gln
                              35                  40                  45

Pro Pro Lys Leu Leu Ile Tyr Trp Ala Ser Thr Arg Glu Ser Gly Val
                      50                  55                  60

Pro Asp Arg Phe Thr Gly Ser Gly Ser Gly Thr Asp Phe Thr Leu Thr
              65                  70                  75                  80
```

```
Ile Ser Ser Val Gln Thr Glu Asp Leu Ala Val Tyr Tyr Cys Gln Asn
                85                  90                  95

Asn Tyr Tyr Phe Pro Leu Thr Phe Gly Ala Gly Thr Lys Leu Glu Leu
            100                 105                 110

Lys

<210> SEQ ID NO 123
<211> LENGTH: 113
<212> TYPE: PRT
<213> ORGANISM: Artificial Sequence
<220> FEATURE:
<223> OTHER INFORMATION: Synthetic

<400> SEQUENCE: 123

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ile Leu Thr
65                  70                  75                  80

Ile Thr Lys Val Gln Ala Glu Asp Leu Ala Val Tyr Tyr Cys Gln Asn
                85                  90                  95

Val Tyr Ser Tyr Pro Leu Thr Phe Gly Ala Gly Thr Lys Leu Glu Leu
            100                 105                 110

Lys

<210> SEQ ID NO 124
<211> LENGTH: 113
<212> TYPE: PRT
<213> ORGANISM: Artificial Sequence
<220> FEATURE:
<223> OTHER INFORMATION: Synthetic

<400> SEQUENCE: 124

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Arg Pro Gly Gln
        35                  40                  45

Pro Pro Lys Leu Leu Ile Tyr Arg Ala Ser Ser Arg Glu Ser Gly Val
    50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ile Tyr Pro Tyr Thr Phe Gly Gly Gly Thr Lys Leu Glu Met
            100                 105                 110

Asn

<210> SEQ ID NO 125
<211> LENGTH: 113
<212> TYPE: PRT
```

```
<213> ORGANISM: Artificial Sequence
<220> FEATURE:
<223> OTHER INFORMATION: Synthetic

<400> SEQUENCE: 125

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Thr Leu Leu Ile Phe Trp Ala Phe Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Asn
                85                  90                  95

Ser Tyr Ser Tyr Pro Phe Thr Phe Gly Ser Gly Thr Lys Leu Glu Ile
            100                 105                 110

Lys

<210> SEQ ID NO 126
<211> LENGTH: 113
<212> TYPE: PRT
<213> ORGANISM: Artificial Sequence
<220> FEATURE:
<223> OTHER INFORMATION: Synthetic

<400> SEQUENCE: 126

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Arg Asn Tyr Leu Thr Trp Tyr Gln Gln Lys Pro Gly Gln
        35                  40                  45

Pro Pro Arg Leu Leu Ile Tyr Trp Ser Ser Thr Arg Asp Ser Gly Val
    50                  55                  60

Pro Asp Arg Phe Thr Gly Ser Gly Ser Arg Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Phe Ile Tyr Pro Leu Thr Phe Gly Ala Gly Thr Lys Leu Glu Leu
            100                 105                 110

Lys

<210> SEQ ID NO 127
<211> LENGTH: 113
<212> TYPE: PRT
<213> ORGANISM: Artificial Sequence
<220> FEATURE:
<223> OTHER INFORMATION: Synthetic

<400> SEQUENCE: 127

Asp Ile Val Met Thr Gln Ser Pro Ser Ser Leu Thr Val Thr Pro Gly
1               5                   10                  15

Glu Lys Val Thr Met Ser Cys Arg Ser Ser Met Ser Leu Phe Asn Ser
            20                  25                  30

Gly Asn Gln Lys Ser Tyr Leu Ser Trp Tyr His Gln Lys Pro Gly Gln
```

```
                35                  40                  45
Pro Pro Lys Leu Leu Ile Tyr Trp Ala Ser Thr Arg Asp Ser Gly Val
 50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Asn
                85                  90                  95

Asp Tyr Ile Tyr Pro Leu Thr Phe Gly Ala Gly Thr Lys Leu Glu Leu
                100                 105                 110

Lys
```

<210> SEQ ID NO 128
<211> LENGTH: 113
<212> TYPE: PRT
<213> ORGANISM: Artificial Sequence
<220> FEATURE:
<223> OTHER INFORMATION: Synthetic

<400> SEQUENCE: 128

```
Asp Ile Val Met Thr Gln Ser Pro Ser Ser Leu Thr Val Thr Ala Gly
1               5                   10                  15

Glu Lys Val Thr Met Asn Cys Arg Ser Ile Gln Ser Leu Leu Asn Ser
                20                  25                  30

Gly Asn Gln Lys Asn Tyr Leu Ser Trp Tyr Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                  70                  75                  80

Ile Arg Ser Val Leu Asp Glu Asp Leu Ala Val Tyr Tyr Cys Gln Asn
                85                  90                  95

Ser Tyr Ser Tyr Pro Phe Thr Phe Gly Ser Gly Thr Lys Leu Glu Met
                100                 105                 110

Lys
```

<210> SEQ ID NO 129
<211> LENGTH: 113
<212> TYPE: PRT
<213> ORGANISM: Artificial Sequence
<220> FEATURE:
<223> OTHER INFORMATION: Synthetic

<400> SEQUENCE: 129

```
Asp Ile Val Met Thr Gln Ser Pro Ser Ser Leu Thr Val Thr Ala Gly
1               5                   10                  15

Glu Lys Val Thr Leu Thr Cys Arg Ser Ser Gln Ser Leu Leu Asn Ser
                20                  25                  30

Gly Asn Arg Lys Asn Tyr Leu Thr Trp Tyr Gln Gln Ile Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Tyr Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Ser Tyr Pro Phe Thr Phe Gly Ser Gly Thr Lys Leu Glu Lys
                100                 105                 110
```

Lys

<210> SEQ ID NO 130
<211> LENGTH: 113
<212> TYPE: PRT
<213> ORGANISM: Artificial Sequence
<220> FEATURE:
<223> OTHER INFORMATION: Synthetic

<400> SEQUENCE: 130

```
Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Phe Asn Ser
            20                  25                  30

Gly Asn Gln Arg Asn Tyr Leu Thr Trp Tyr Gln Arg Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Tyr Phe Thr Leu Thr
65                  70                  75                  80

Val Ser Ser Val Gln Ala Glu Asp Leu Ala Val Tyr Tyr Cys Gln Asn
                85                  90                  95

Ala Tyr Tyr Phe Pro Phe Thr Phe Gly Ser Gly Thr Lys Leu Glu Lys
            100                 105                 110

Lys
```

<210> SEQ ID NO 131
<211> LENGTH: 113
<212> TYPE: PRT
<213> ORGANISM: Artificial Sequence
<220> FEATURE:
<223> OTHER INFORMATION: Synthetic

<400> SEQUENCE: 131

```
Asp Ile Val Met Thr Gln Ser Pro Ser Ser Leu Thr Val Thr Ala Arg
1               5                   10                  15

Glu Arg Val Ser Met Thr Cys Lys Ser Ser Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ser Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Phe Cys Gln Asn
                85                  90                  95

Asn Tyr Tyr Tyr Pro Phe Thr Phe Gly Ser Gly Thr Lys Leu Glu Ile
            100                 105                 110

Lys
```

<210> SEQ ID NO 132
<211> LENGTH: 113
<212> TYPE: PRT
<213> ORGANISM: Artificial Sequence
<220> FEATURE:
<223> OTHER INFORMATION: Synthetic

<400> SEQUENCE: 132

```
Asp Ile Val Met Thr Gln Ser Pro Ser Ser Leu Thr Val Thr Ala Gly
1               5                   10                  15

Glu Arg Val Thr Met Arg Cys Arg Ser Thr Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Gly Ser Gly Thr Asp Phe Thr Leu Thr
65                  70                  75                  80

Ile Ser Ser Val Gln Ala Glu Asp Leu Ala Val Tyr Tyr Cys Gln Asn
                    85                  90                  95

Ala Tyr Tyr Tyr Pro Leu Thr Phe Gly Ala Gly Thr Lys Leu Glu Arg
                100                 105                 110

Lys
```

<210> SEQ ID NO 133
<211> LENGTH: 113
<212> TYPE: PRT
<213> ORGANISM: Artificial Sequence
<220> FEATURE:
<223> OTHER INFORMATION: Synthetic

<400> SEQUENCE: 133

```
Asp Ile Val Met Thr Gln Ser Pro Ser Ser Leu Thr Val Thr Ala Gly
1               5                   10                  15

Glu Arg Val Thr Met Ser Cys Lys Pro Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Lys Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                    85                  90                  95

Ala Tyr Phe Tyr Pro Cys Thr Phe Gly Gly Gly Thr Lys Leu Glu Met
                100                 105                 110

Lys
```

<210> SEQ ID NO 134
<211> LENGTH: 113
<212> TYPE: PRT
<213> ORGANISM: Artificial Sequence
<220> FEATURE:
<223> OTHER INFORMATION: Synthetic

<400> SEQUENCE: 134

```
Asp Ile Val Met Thr Gln Ser Pro Ser Ser Leu Thr Val Thr Ala Gly
1               5                   10                  15

Glu Lys Val Thr Met Arg Cys Arg Ser Thr Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
```

```
65                  70                  75                  80
Ile Ser Ser Val Gln Ala Glu Asp Leu Ala Val Tyr Tyr Cys Gln Asn
                85                  90                  95

Ala Tyr Tyr Tyr Pro Leu Thr Phe Gly Val Gly Thr Lys Leu Glu Arg
            100                 105                 110

Lys

<210> SEQ ID NO 135
<211> LENGTH: 113
<212> TYPE: PRT
<213> ORGANISM: Artificial Sequence
<220> FEATURE:
<223> OTHER INFORMATION: Synthetic

<400> SEQUENCE: 135

Asp Ile Val Met Thr Gln Ser Pro Ser Ser Leu Thr Val Thr Ala Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ser Gly Val
    50                  55                  60

Pro Asp Arg Phe Lys Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Phe Tyr Pro Cys Thr Phe Gly Gly Thr Lys Leu Glu Met
            100                 105                 110

Lys

<210> SEQ ID NO 136
<211> LENGTH: 113
<212> TYPE: PRT
<213> ORGANISM: Artificial Sequence
<220> FEATURE:
<223> OTHER INFORMATION: Synthetic

<400> SEQUENCE: 136

Asp Ile Val Met Thr Gln Ser Pro Ser Ser Leu Thr Val Thr Thr Gly
1               5                   10                  15

Glu Lys Val Thr Met Ser Cys Lys Ser Ser Gln Ser Val Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Val Tyr Trp Ala Ser Thr Arg Glu Ser Gly Val
    50                  55                  60

Pro Ala Arg Phe Thr Gly Ser Gly Ser Gly Thr Val Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Tyr Phe Pro Leu Thr Phe Gly Ala Gly Thr Arg Leu Glu Leu
            100                 105                 110

Lys

<210> SEQ ID NO 137
<211> LENGTH: 113
```

-continued

```
<212> TYPE: PRT
<213> ORGANISM: Artificial Sequence
<220> FEATURE:
<223> OTHER INFORMATION: Synthetic

<400> SEQUENCE: 137

Asp Ile Val Met Thr Gln Ser Pro Ser Ser Gln Thr Val Thr Ala Gly
1               5                   10                  15

Glu Lys Val Thr Leu Ser Cys Arg Ser Ser Gln Ser Leu Leu Asn Gly
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Tyr Phe Thr Phe Thr
65                  70                  75                  80

Ile Ser Ser Val Gln Ala Glu Asp Leu Ala Val Tyr Tyr Cys Gln Asn
                85                  90                  95

Ala Tyr Phe Tyr Pro Phe Thr Phe Gly Ala Gly Thr Lys Leu Glu Leu
            100                 105                 110

Lys

<210> SEQ ID NO 138
<211> LENGTH: 113
<212> TYPE: PRT
<213> ORGANISM: Artificial Sequence
<220> FEATURE:
<223> OTHER INFORMATION: Synthetic

<400> SEQUENCE: 138

Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Asn Ser
            20                  25                  30

Gly Asn Gln Arg Asn Tyr Leu Ser Trp Tyr Gln Gln Glu Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Ile Gln Ala Glu Asp Leu Ala Leu Tyr Phe Cys Gln Asn
                85                  90                  95

Ala Tyr Phe Tyr Pro Phe Thr Phe Gly Ser Gly Thr Lys Leu Glu Ile
            100                 105                 110

Lys

<210> SEQ ID NO 139
<211> LENGTH: 113
<212> TYPE: PRT
<213> ORGANISM: Artificial Sequence
<220> FEATURE:
<223> OTHER INFORMATION: Synthetic

<400> SEQUENCE: 139

Asp Ile Leu Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30
```

Gly Asn Gln Lys Asn Tyr Leu Thr Trp Tyr Gln Gln Lys Pro Gly Gln
                35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asn Tyr Phe Tyr Pro Leu Thr Phe Gly Val Gly Thr Lys Leu Glu Leu
                100                 105                 110

Lys

<210> SEQ ID NO 140
<211> LENGTH: 113
<212> TYPE: PRT
<213> ORGANISM: Artificial Sequence
<220> FEATURE:
<223> OTHER INFORMATION: Synthetic

<400> SEQUENCE: 140

Asp Ile Val Met Thr Gln Ser Pro Ser Ser Leu Thr Val Thr Thr Gly
 1               5                  10                  15

Glu Lys Val Thr Met Ser Cys Lys Ser Ser Gln Ser Leu Phe Asn Ser
                 20                  25                  30

Gly Asn Gln Lys Asn Tyr Leu Thr Trp Tyr Gln Gln Lys Pro Gly Gln
                 35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Tyr Phe Thr Leu Thr
 65                  70                  75                  80

Ile Ser Ser Val Gln Ala Glu Asp Leu Ala Val Tyr Tyr Cys Gln Asn
                 85                  90                  95

Asn Tyr Ile Tyr Pro Leu Ala Phe Gly Thr Gly Thr Lys Leu Glu Leu
                100                 105                 110

Lys

<210> SEQ ID NO 141
<211> LENGTH: 113
<212> TYPE: PRT
<213> ORGANISM: Artificial Sequence
<220> FEATURE:
<223> OTHER INFORMATION: Synthetic

<400> SEQUENCE: 141

Asp Ile Val Met Thr Gln Ser Pro Ser Ser Leu Thr Val Thr Ala Gly
 1               5                  10                  15

Glu Lys Val Thr Met Ser Cys Lys Ser Ser Gln Ser Leu Leu Asn Ser
                 20                  25                  30

Gly Asn Gln Lys Asn Tyr Leu Thr Trp Tyr Gln Gln Arg Pro Gly Gln
                 35                  40                  45

Pro Pro Lys Leu Leu Met Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Gly Gln Ala Glu Asp Leu Ala Ile Tyr Phe Cys Gln Asn
                 85                  90                  95

Gly Tyr Tyr Phe Pro Phe Thr Phe Gly Ser Gly Thr Lys Leu Glu Thr

<210> SEQ ID NO 142
<211> LENGTH: 113
<212> TYPE: PRT
<213> ORGANISM: Artificial Sequence
<220> FEATURE:
<223> OTHER INFORMATION: Synthetic

<400> SEQUENCE: 142

Asp Ile Val Met Thr Gln Ser Pro Ser Ser Leu Thr Val Thr Ala Gly
1               5                   10                  15

Glu Lys Val Thr Met Arg Cys Arg Ser Ser Gln Ser Leu Phe Asn Ser
            20                  25                  30

Gly Asn Gln Arg Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Ile Tyr Pro Leu Ala Phe Gly Ala Gly Thr Lys Leu Glu Leu
            100                 105                 110

Lys

<210> SEQ ID NO 143
<211> LENGTH: 113
<212> TYPE: PRT
<213> ORGANISM: Artificial Sequence
<220> FEATURE:
<223> OTHER INFORMATION: Synthetic

<400> SEQUENCE: 143

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Phe Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asn Tyr Ile Tyr Pro Leu Ala Phe Gly Ala Gly Thr Lys Leu Glu Leu
            100                 105                 110

Lys

<210> SEQ ID NO 144
<211> LENGTH: 113
<212> TYPE: PRT
<213> ORGANISM: Artificial Sequence
<220> FEATURE:
<223> OTHER INFORMATION: Synthetic

<400> SEQUENCE: 144

```
Asp Ile Val Met Thr Gln Ser Pro Ser Ser Leu Thr Val Thr Ala Gly
1               5                   10                  15

Glu Lys Val Thr Met Arg Cys Lys Ser Thr Gln Ser Leu Leu Asn Ser
            20                  25                  30

Gly Asn Gln Arg Asn Tyr Leu Thr Trp Tyr Gln Lys Pro Gly Gln
        35                  40                  45

Ser Pro Lys Leu Leu Ile Tyr Trp Ala Ser Thr Arg Glu Ser Gly Val
50                  55                  60

Pro Glu Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Tyr Tyr Pro Leu Thr Phe Gly Pro Gly Thr Lys Leu Glu Arg
            100                 105                 110

Lys
```

<210> SEQ ID NO 145
<211> LENGTH: 118
<212> TYPE: PRT
<213> ORGANISM: Artificial Sequence
<220> FEATURE:
<223> OTHER INFORMATION: Synthetic

<400> SEQUENCE: 145

```
Gln Val Gln Leu His Gln Ser Gly Thr Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Leu Glu Trp Val Lys Gln Arg Pro Gly Gln Gly Leu Glu Trp Ile
        35                  40                  45

Gly Glu Ile Asn Pro Gly Asn Gly Gly Ser Tyr Asn Glu Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ile Tyr Tyr Gly Asn Ser Phe Ala Tyr Trp Gly Gln Gly Thr
            100                 105                 110

Leu Val Thr Val Ser Ala
        115
```

<210> SEQ ID NO 146
<211> LENGTH: 118
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Val Arg Gln Pro Pro Gly Lys Gly Leu Glu Trp Leu
        35                  40                  45

Gly Val Ile Trp Gly Asp Gly Asn Thr Ile Tyr His Ser Ala Leu Lys
50                  55                  60
```

```
Ser Arg Leu Ser Ile Ser Arg Asp Asn Ser Lys Arg Gln Val Phe Leu
 65                  70                  75                  80

Lys Val Asn Ser Leu Gln Ile Asp Asp Thr Ala Thr Tyr Tyr Cys Ala
                 85                  90                  95

Lys Gln Gly Leu Tyr Gly His Ala Met Asp Tyr Trp Gly Gln Gly Thr
            100                 105                 110

Ser Val Ile Val Ser Ser
            115

<210> SEQ ID NO 147
<211> LENGTH: 118
<212> TYPE: PRT
<213> ORGANISM: Artificial Sequence
<220> FEATURE:
<223> OTHER INFORMATION: Synthetic

<400> SEQUENCE: 147

Asp Val Gln Leu Val Glu Ser Gly Gly Leu Val Gln Pro Gly Gly
  1               5                  10                  15

Ser Arg Lys Leu Ser Cys Thr Ala Ser Gly Phe Thr Phe Asn Ser Phe
                 20                  25                  30

Gly Met Asn Trp Val Arg Gln Ala Pro Glu Lys Gly Leu Glu Trp Val
             35                  40                  45

Ala Phe Ile Ser Gly Gly Ser Asn Thr Ile His Tyr Leu Asp Thr Val
 50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Thr Arg Leu Ala Leu Gly Asn Ala Met Asp Tyr Trp Gly Gln Gly Thr
            100                 105                 110

Ser Val Ile Val Ser Ser
            115

<210> SEQ ID NO 148
<211> LENGTH: 123
<212> TYPE: PRT
<213> ORGANISM: Artificial Sequence
<220> FEATURE:
<223> OTHER INFORMATION: Synthetic

<400> SEQUENCE: 148

Glu Val Gln His Val Glu Thr Gly Gly Gly Leu Val Gln Pro Lys Gly
  1               5                  10                  15

Ser Leu Lys Leu Ser Cys Ala Ala Ser Gly Phe Thr Phe Asn Thr Asn
                 20                  25                  30

Ala Met Asn Trp Val Arg Gln Ala Pro Gly Lys Gly Leu Glu Trp Val
             35                  40                  45

Ala Arg Ile Arg Ser Lys Ser Asn Asn Tyr Ala Thr Tyr Tyr Ala Asp
 50                  55                  60

Ser Val Lys Asp Arg Phe Thr Ile Ser Arg Asp Asp Ser Gln Ser Met
 65                  70                  75                  80

Leu Tyr Val Gln Met Asn Asn Leu Lys Thr Glu Asp Thr Ala Met Tyr
                 85                  90                  95

Tyr Cys Val Ser Gly Ala Tyr Tyr Gly Asn Ser Lys Ala Phe Asp Tyr
            100                 105                 110

Trp Gly Gln Gly Thr Leu Val Thr Val Ser Ala
```

<210> SEQ ID NO 149
<211> LENGTH: 120
<212> TYPE: PRT
<213> ORGANISM: Artificial Sequence
<220> FEATURE:
<223> OTHER INFORMATION: Synthetic

<400> SEQUENCE: 149

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Pro Thr Tyr
            20                  25                  30

Ser Ile His Trp Leu Lys Gln Gly Pro Gly Gln Gly Leu Glu Trp Ile
        35                  40                  45

Gly Tyr Ile Asn Pro Ser Thr Ile Tyr Thr Asn Tyr Asn Gln Lys Phe
    50                  55                  60

Lys Tyr Lys Ala Thr Leu Thr Ala Asp Lys Ser Ser Thr Ala Tyr
65                  70                  75                  80

Ile Gln Leu Ser Ser Leu Thr Ser Asp Asp Ser Ala Val Tyr Tyr Cys
                85                  90                  95

Ala Arg Glu Gly Tyr Gly Arg Gly Asn Ala Met Asp Tyr Trp Gly Gln
            100                 105                 110

Gly Thr Ser Val Thr Val Ser Ser
        115                 120
```

<210> SEQ ID NO 150
<211> LENGTH: 118
<212> TYPE: PRT
<213> ORGANISM: Artificial Sequence
<220> FEATURE:
<223> OTHER INFORMATION: Synthetic

<400> SEQUENCE: 150

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Phe Ser Tyr Gly Asp Ser His Asn Tyr Tyr Ser Asp Ser Val
    50                  55                  60

Lys Gly Arg Phe Thr Ile Ser Arg Asp Ile Lys Asp Ala Leu Tyr
65                  70                  75                  80

Leu Gln Met Ser Ser Leu Arg Ser Glu Asp Thr Ala Ile Tyr Tyr Cys
                85                  90                  95

Ala Arg Phe Gly Arg Gly Asn Thr Met Asp Tyr Trp Gly Gln Gly Thr
            100                 105                 110

Ser Val Thr Val Ser Leu
        115
```

<210> SEQ ID NO 151
<211> LENGTH: 118
<212> TYPE: PRT
<213> ORGANISM: Artificial Sequence
<220> FEATURE:
<223> OTHER INFORMATION: Synthetic

<400> SEQUENCE: 151

```
Gln Ile Gln Leu Val Gln Ser Gly Pro Glu Leu Arg Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Ala Trp Ile Asn Ala Asn Thr Gly Glu Pro Thr Tyr Ala Glu Glu Phe
        50                  55                  60

Lys Gly Arg Phe Ala Phe Ser Leu Glu Thr Ser Ala Arg Ser Ala Tyr
65                  70                  75                  80

Leu Gln Ile Asn Ser Leu Lys Asn Glu Asp Thr Ala Thr Tyr Phe Cys
                85                  90                  95

Ala Arg Leu Thr Arg Gly Asn Ser Phe Asp Tyr Trp Gly Gln Gly Thr
            100                 105                 110

Thr Leu Thr Val Ser Ser
            115

<210> SEQ ID NO 152
<211> LENGTH: 118
<212> TYPE: PRT
<213> ORGANISM: Artificial Sequence
<220> FEATURE:
<223> OTHER INFORMATION: Synthetic

<400> SEQUENCE: 152

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
                20                  25                  30

Gly Met Asn Trp Val Arg Gln Ala Pro Gly Lys Gly Leu Lys Trp Met
            35                  40                  45

Gly Trp Ile Ser Thr Asn Thr Gly Glu Pro Thr Tyr Ala Glu Glu Phe
        50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Ala Arg Leu Val Arg Gly Asn Ser Phe Asp Phe Trp Gly Gln Gly Ile
            100                 105                 110

Thr Leu Thr Val Ser Ser
            115

<210> SEQ ID NO 153
<211> LENGTH: 120
<212> TYPE: PRT
<213> ORGANISM: Artificial Sequence
<220> FEATURE:
<223> OTHER INFORMATION: Synthetic

<400> SEQUENCE: 153

Gln Val Gln Leu Gln Gln Ser Gly Gly Glu Leu Val Lys Pro Gly Ala
1               5                   10                  15

Ser Val Lys Met Ser Cys Lys Ala Phe Gly Tyr Thr Phe Thr Thr Tyr
                20                  25                  30

Pro Ile Glu Trp Met Lys Gln Asn His Gly Lys Ser Leu Glu Trp Ile
            35                  40                  45

Gly Asn Phe His Pro Tyr Asn Asp Asp Thr Lys Tyr Asn Glu Lys Phe
```

```
                    50                  55                  60
Lys Gly Lys Ala Lys Leu Thr Val Glu Lys Ser Ser Thr Val Tyr
 65                  70                  75                  80

Leu Glu Val Ser Arg Leu Thr Ser Asp Asp Ser Ala Val Tyr Tyr Cys
                 85                  90                  95

Ala Arg Arg Ala Tyr Gly Tyr Pro Tyr Ala Met Asp Tyr Trp Gly Gln
            100                 105                 110

Gly Thr Ser Val Thr Val Ser Ser
            115                 120

<210> SEQ ID NO 154
<211> LENGTH: 119
<212> TYPE: PRT
<213> ORGANISM: Artificial Sequence
<220> FEATURE:
<223> OTHER INFORMATION: Synthetic

<400> SEQUENCE: 154

Gln Val His Leu Gln Gln Ser Gly Ala Glu Val Val Arg Pro Gly Thr
  1               5                  10                  15

Ser Val Lys Val Ser Cys Lys Ala Ser Gly Tyr Ala Phe Thr Asn Tyr
                 20                  25                  30

Leu Ile Glu Trp Ile Lys Lys Arg Pro Gly Gln Gly Leu Glu Trp Val
             35                  40                  45

Gly Val Ile Asn Pro Gly Arg Ser Gly Thr Asn Tyr Asn Glu Lys Phe
         50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Asp Asp Ser Ala Val Tyr Phe Cys
                 85                  90                  95

Ala Arg Thr Arg Tyr Gly Gly Asn Ala Met Asp Tyr Trp Gly Gln Gly
            100                 105                 110

Thr Ser Val Thr Val Ser Ser
            115

<210> SEQ ID NO 155
<211> LENGTH: 117
<212> TYPE: PRT
<213> ORGANISM: Artificial Sequence
<220> FEATURE:
<223> OTHER INFORMATION: Synthetic

<400> SEQUENCE: 155

Gln Val Gln Leu Lys Glu Ser Gly Pro Gly Gln Val Ala Pro Ser Gln
  1               5                  10                  15

Ser Leu Ser Ile Ala Cys Thr Val Ser Gly Phe Ser Leu Ser Ser Tyr
                 20                  25                  30

Gly Val His Trp Val Arg Gln Pro Pro Gly Lys Gly Leu Glu Trp Leu
             35                  40                  45

Gly Val Ile Trp Ala Gly Gly Ser Thr Asn Tyr Asp Ser Ala Leu Met
         50                  55                  60

Ser Arg Leu Thr Ile Ser Lys Asp Asn Ser Arg Thr Arg Val Phe Leu
 65                  70                  75                  80

Lys Met Asn Ser Leu Gln Thr Asp Asp Thr Ala Ile Tyr Tyr Cys Ala
                 85                  90                  95

Arg Ser Leu Tyr Gly Asn Ser Leu Asp Ser Trp Gly Pro Gly Thr Thr
            100                 105                 110
```

Leu Thr Val Ser Ser
        115

<210> SEQ ID NO 156
<211> LENGTH: 117
<212> TYPE: PRT
<213> ORGANISM: Artificial Sequence
<220> FEATURE:
<223> OTHER INFORMATION: Synthetic

<400> SEQUENCE: 156

Gln Val Gln Leu Lys Glu Ser Gly Pro Gly Leu Val Ala Pro Ser Gln
1               5                   10                  15

Ser Leu Ser Ile Thr Cys Thr Val Ser Gly Leu Ser Leu Thr Ser Phe
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Tyr Leu
65                  70                  75                  80

Lys Met His Ser Leu Gln Thr Asp Asp Thr Ala Met Tyr Tyr Cys Ala
                85                  90                  95

Arg Ser Leu Tyr Gly Asn Ser Phe Asp Tyr Trp Gly Gln Gly Thr Ala
            100                 105                 110

Leu Thr Val Ser Ser
        115

<210> SEQ ID NO 157
<211> LENGTH: 117
<212> TYPE: PRT
<213> ORGANISM: Artificial Sequence
<220> FEATURE:
<223> OTHER INFORMATION: Synthetic

<400> SEQUENCE: 157

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Asn Trp Val Arg Gln Pro Pro Gly Lys Gly Leu Glu Trp Leu
        35                  40                  45

Ala Ala Ile Arg Ser Asp Gly Ile Ile Thr Tyr Asn Ser Val Leu Lys
    50                  55                  60

Ser Arg Leu Arg Ile Ser Lys Asp Asn Ser Lys Ser Gln Val Phe Leu
65                  70                  75                  80

Lys Met Asn Ser Leu Gln Thr Asp Asp Thr Ala Met Phe Tyr Cys Ala
                85                  90                  95

Arg Trp Phe Arg Gly Asn Val Leu Asp Tyr Trp Gly Gln Gly Thr Ser
            100                 105                 110

Val Thr Val Ser Ser
        115

<210> SEQ ID NO 158
<211> LENGTH: 118
<212> TYPE: PRT
<213> ORGANISM: Artificial Sequence
<220> FEATURE:
<223> OTHER INFORMATION: Synthetic

<400> SEQUENCE: 158

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Arg Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Tyr Asp Thr Ala Met Tyr Tyr Cys Ala
                85                  90                  95

Arg Asp Arg Tyr Gly Gly Asn Ser Leu Asp Tyr Trp Gly Gln Gly Thr
            100                 105                 110

Ser Val Thr Val Ser Ser
        115

<210> SEQ ID NO 159
<211> LENGTH: 119
<212> TYPE: PRT
<213> ORGANISM: Artificial Sequence
<220> FEATURE:
<223> OTHER INFORMATION: Synthetic

<400> SEQUENCE: 159

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Thr Phe
            20                  25                  30

Gly Met His Trp Val Arg Gln Ala Pro Glu Lys Gly Leu Glu Trp Val
        35                  40                  45

Ala Tyr Ile Thr Ser Gly Asn Ser Pro Ile Tyr Phe Thr Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Gly Ser Glu Asp Thr Ala Val Tyr Tyr Cys
                85                  90                  95

Ala Arg Ser Ser Tyr Tyr Gly Asn Ser Met Asp Tyr Trp Gly Gln Gly
            100                 105                 110

Thr Ser Val Thr Val Ser Ser
        115

<210> SEQ ID NO 160
<211> LENGTH: 118
<212> TYPE: PRT
<213> ORGANISM: Artificial Sequence
<220> FEATURE:
<223> OTHER INFORMATION: Synthetic

<400> SEQUENCE: 160

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Asn Thr Tyr
            20                  25                  30

Gly Val His Trp Val Arg Gln Pro Pro Gly Lys Gly Leu Glu Trp Leu
        35                  40                  45

Val Val Met Leu Ser Asp Gly Asn Thr Val Tyr Asn Ser Ser Leu Lys
    50                  55                  60

Ser Arg Leu Ser Leu Thr Lys Asp Asn Ser Lys Ser Gln Leu Leu Leu
 65                  70                  75                  80

Lys Met Asn Ser Leu Gln Thr Asp Asp Thr Ala Ile Tyr Tyr Cys Ala
                 85                  90                  95

Arg His Lys Ala Tyr Gly Asn Ala Met Asp Tyr Trp Gly Gln Gly Thr
                100                 105                 110

Ser Val Thr Val Ser Ser
            115

<210> SEQ ID NO 161
<211> LENGTH: 117
<212> TYPE: PRT
<213> ORGANISM: Artificial Sequence
<220> FEATURE:
<223> OTHER INFORMATION: Synthetic

<400> SEQUENCE: 161

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ile Asn Tyr
                 20                  25                  30

Gly Val Ser Trp Val Arg Gln Pro Pro Gly Lys Gly Leu Glu Trp Leu
             35                  40                  45

Gly Val Ile Trp Gly Asp Gly Asn Thr Asn Tyr Gln Ser Ala Leu Arg
         50                  55                  60

Ser Arg Leu Ser Ile Arg Lys Asp Thr Ser Lys Ser Gln Val Phe Leu
 65                  70                  75                  80

Lys Leu Asn Ser Val His Thr Asp Gly Thr Ala Thr Tyr Tyr Cys Ala
                 85                  90                  95

Lys Val Gly Arg Gly Asn Ala Met Asp His Trp Gly Gln Gly Ile Ser
                100                 105                 110

Val Ile Val Ser Ser
            115

<210> SEQ ID NO 162
<211> LENGTH: 117
<212> TYPE: PRT
<213> ORGANISM: Artificial Sequence
<220> FEATURE:
<223> OTHER INFORMATION: Synthetic

<400> SEQUENCE: 162

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ile Asn Tyr
                 20                  25                  30

Gly Val Ser Trp Val Arg Gln Pro Pro Gly Lys Gly Leu Glu Trp Leu
             35                  40                  45

Gly Val Ile Arg Gly Asp Gly Asn Thr Asn Tyr Gln Ser Ala Leu Arg
         50                  55                  60

Ser Arg Leu Ser Ile Arg Lys Asp Thr Ser Lys Ser Gln Val Phe Leu
 65                  70                  75                  80

Lys Leu Asn Ser Val His Thr Asp Gly Thr Ala Thr Tyr Tyr Cys Ala
                 85                  90                  95

Lys Val Gly Arg Gly Asn Ala Met Asp His Trp Gly Gln Gly Ile Ser
                100                 105                 110

Val Ile Val Ser Ser
        115

<210> SEQ ID NO 163
<211> LENGTH: 118
<212> TYPE: PRT
<213> ORGANISM: Artificial Sequence
<220> FEATURE:
<223> OTHER INFORMATION: Synthetic

<400> SEQUENCE: 163

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Gly Phe
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Ser Glu Lys Phe
    50                  55                  60

Lys Gly Lys Ala Thr Leu Thr Ser Asp Lys Ser Ser Ser Thr Ala Phe
65                  70                  75                  80

Met Glu Leu Ser Ser Leu Thr Ser Asp Asp Ser Ala Val Tyr Tyr Cys
                85                  90                  95

Ala Arg Leu Asp Tyr Gly Asn Ala Met Asp Tyr Trp Gly Gln Gly Thr
            100                 105                 110

Ser Val Thr Val Ser Ser
        115

<210> SEQ ID NO 164
<211> LENGTH: 118
<212> TYPE: PRT
<213> ORGANISM: Artificial Sequence
<220> FEATURE:
<223> OTHER INFORMATION: Synthetic

<400> SEQUENCE: 164

Gln Val Gln Leu Lys Gln Ser Gly Pro Gly Leu Val Gln Pro Ser Gln
1               5                   10                  15

Ser Leu Ser Ile Thr Cys Thr Val Ser Asp Phe Ser Leu Thr Lys Tyr
            20                  25                  30

Gly Val His Trp Phe Arg Gln Ser Pro Gly Lys Gly Leu Glu Trp Leu
        35                  40                  45

Gly Val Ile Trp Thr Gly Gly Asn Thr Asp Tyr Asn Pro Ala Leu Ile
    50                  55                  60

Pro Arg Leu Ser Phe Arg Lys Asp Asn Ser Lys Ser Gln Val Phe Phe
65                  70                  75                  80

Lys Met Asn Ser Leu Gln Ser Ser Asp Thr Ala Val Tyr Tyr Cys Ala
                85                  90                  95

Arg Asn Gly Tyr Tyr Gly Asn Ala Met Asp Tyr Trp Gly Gln Gly Thr
            100                 105                 110

Ser Val Thr Val Ser Ser
        115

<210> SEQ ID NO 165
<211> LENGTH: 118
<212> TYPE: PRT
<213> ORGANISM: Artificial Sequence
<220> FEATURE:
<223> OTHER INFORMATION: Synthetic -continued

<400> SEQUENCE: 165

Glu Val Gln Leu Gln Gln Ser Gly Pro Glu Leu Val Lys Pro Gly Ala
1               5                   10                  15

Ser Val Lys Met Ser Cys Lys Ser Ser Gly Tyr Thr Phe Thr Gly Phe
            20                  25                  30

Leu Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Ser Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Asp Asp Ser Ala Val Tyr Tyr Cys
                85                  90                  95

Gly Arg Leu Asp Tyr Gly Asn Ala Met Asp Tyr Trp Gly Gln Gly Thr
            100                 105                 110

Ser Val Thr Val Ser Ser
        115

<210> SEQ ID NO 166
<211> LENGTH: 115
<212> TYPE: PRT
<213> ORGANISM: Artificial Sequence
<220> FEATURE:
<223> OTHER INFORMATION: Synthetic

<400> SEQUENCE: 166

Asp Val Gln Leu Gln Glu Ser Gly Pro Gly Leu Val Lys Pro Ser Gln
1               5                   10                  15

Ser Leu Ser Leu Ser Cys Ser Val Thr Gly Tyr Ser Ile Thr Ser Gly
            20                  25                  30

Tyr Phe Trp Thr Trp Phe Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Ser Phe Arg Phe Phe Ala Tyr Trp Gly Gln Gly Thr Leu Val Thr
            100                 105                 110

Val Ser Ala
        115

<210> SEQ ID NO 167
<211> LENGTH: 119
<212> TYPE: PRT
<213> ORGANISM: Artificial Sequence
<220> FEATURE:
<223> OTHER INFORMATION: Synthetic

<400> SEQUENCE: 167

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Asn Tyr
            20                  25                  30

Gly Val Ser Trp Val Arg Gln Pro Pro Gly Lys Gly Leu Glu Trp Leu
        35                  40                  45

Gly Val Ile Trp Ala Gly Gly Asn Thr Asn Tyr Asn Ser Ala Leu Met
            50                  55                  60

Ser Arg Leu Arg Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Arg His Gly Tyr Gly Lys Gly Asn Ala Met Asp Asn Trp Gly Gln Gly
                100                 105                 110

Thr Ser Val Thr Val Ser Ser
            115

<210> SEQ ID NO 168
<211> LENGTH: 118
<212> TYPE: PRT
<213> ORGANISM: Artificial Sequence
<220> FEATURE:
<223> OTHER INFORMATION: Synthetic

<400> SEQUENCE: 168

Gln Val Gln Leu Gln Gln Pro Gly Ala Glu Pro Val Lys Pro Gly Ala
 1               5                  10                  15

Ser Val Lys Leu Ser Cys Lys Ala Ser Gly Tyr Ser Phe Thr Asn Phe
                20                  25                  30

Leu Thr His Trp Val Arg Gln Arg Pro Gly Gln Gly Leu Glu Trp Ile
            35                  40                  45

Gly Glu Ile Asn Pro Thr Asn Gly Arg Thr Tyr Tyr Asn Glu Lys Phe
        50                  55                  60

Lys Arg Lys Ala Thr Leu Thr Val Asp Lys Ser Ser Thr Thr Val Tyr
 65                  70                  75                  80

Met Gln Leu Ser Asn Leu Thr Pro Glu Asp Ser Ala Val Phe Tyr Cys
                 85                  90                  95

Ala Arg Ile Tyr Tyr Gly Asn Ser Met Asp Tyr Trp Gly Gln Gly Thr
                100                 105                 110

Leu Val Thr Val Ser Ala
            115

<210> SEQ ID NO 169
<211> LENGTH: 120
<212> TYPE: PRT
<213> ORGANISM: Artificial Sequence
<220> FEATURE:
<223> OTHER INFORMATION: Synthetic

<400> SEQUENCE: 169

Gln Val Gln Leu Gln Gln Ser Gly Ala Glu Leu Ala Arg Pro Gly Ala
 1               5                  10                  15

Ser Val Lys Met Ser Cys Lys Ala Ser Gly Tyr Thr Phe Pro Thr Tyr
                20                  25                  30

Ser Ile His Trp Leu Lys Gln Gly Pro Gly Gln Gly Leu Glu Trp Ile
            35                  40                  45

Gly Tyr Ile Asn Pro Asn Thr Ile Tyr Thr Asn Tyr Asn Gln Lys Phe
        50                  55                  60

Lys Tyr Lys Thr Thr Leu Thr Ala Asp Lys Ser Ser Thr Ala Tyr
 65                  70                  75                  80

Ile Gln Leu Ser Ser Leu Thr Ser Asp Asp Ser Ala Val Tyr Tyr Cys
                 85                  90                  95

Ala Arg Glu Gly Tyr Gly Arg Gly Asn Ala Met Asp Tyr Trp Gly Gln

-continued

```
                100                 105                 110

Gly Thr Ser Val Thr Val Ser Ser
        115                 120

<210> SEQ ID NO 170
<211> LENGTH: 117
<212> TYPE: PRT
<213> ORGANISM: Artificial Sequence
<220> FEATURE:
<223> OTHER INFORMATION: Synthetic

<400> SEQUENCE: 170

Gln Val Gln Leu Lys Glu Ser Gly Pro Gly Leu Val Ala Pro Ser Gln
1               5                   10                  15

Ser Leu Ser Ile Thr Cys Thr Val Thr Gly Phe Ser Leu Ser Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asp Ser Ala Leu Met
    50                  55                  60

Ser Arg Leu Ser Ile Ser Lys Asp Arg Ser Lys Ser Gln Val Phe Leu
65                  70                  75                  80

Lys Met Thr Ser Leu Gln Thr Asp Asp Thr Ala Met Tyr Tyr Cys Ala
                85                  90                  95

Arg Ser Leu Tyr Gly Asn Ser Phe Asp His Trp Gly Gln Gly Thr Thr
            100                 105                 110

Leu Thr Val Ser Ser
        115

<210> SEQ ID NO 171
<211> LENGTH: 118
<212> TYPE: PRT
<213> ORGANISM: Artificial Sequence
<220> FEATURE:
<223> OTHER INFORMATION: Synthetic

<400> SEQUENCE: 171

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Gly Tyr
            20                  25                  30

Ile Ile Gln Trp Met Lys Gln Lys Pro Gly Leu Gly Leu Glu Trp Ile
        35                  40                  45

Gly Phe Ile Asn Pro Tyr Asn Asp Gly Thr Lys Tyr Asn Glu Gln Phe
    50                  55                  60

Lys Gly Lys Ala Thr Leu Thr Ser Asp Lys Ser Ser Asn Ala Ala Tyr
65                  70                  75                  80

Met Glu Leu Ser Ser Leu Thr Ser Glu Asp Ser Ala Val Tyr Tyr Cys
                85                  90                  95

Ala Arg Ala Tyr Phe Gly Asn Ser Phe Ala Tyr Trp Gly Gln Gly Thr
            100                 105                 110

Leu Val Thr Val Ser Ala
        115

<210> SEQ ID NO 172
<211> LENGTH: 117
<212> TYPE: PRT
<213> ORGANISM: Artificial Sequence
<220> FEATURE:
```

<223> OTHER INFORMATION: Synthetic

<400> SEQUENCE: 172

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ser Thr Asn Tyr Asp Ser Thr Leu Met
    50                  55                  60

Ser Arg Leu Ser Ile Ser Lys Asp Arg Ser Lys Ser Gln Val Phe Leu
65                  70                  75                  80

Lys Met Thr Ser Leu Gln Thr Asp Asp Thr Ala Met Tyr Tyr Cys Ala
                85                  90                  95

Arg Ser Leu Tyr Gly Asn Ser Phe Asp His Trp Gly Gln Gly Thr Thr
            100                 105                 110

Leu Thr Val Ser Ser
        115
```

<210> SEQ ID NO 173
<211> LENGTH: 117
<212> TYPE: PRT
<213> ORGANISM: Artificial Sequence
<220> FEATURE:
<223> OTHER INFORMATION: Synthetic

<400> SEQUENCE: 173

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asp Ser Ala Leu Met
    50                  55                  60

Ser Arg Leu Ser Ile Ser Lys Asp Arg Ser Lys Ser Gln Val Phe Leu
65                  70                  75                  80

Lys Met Thr Ser Leu Gln Thr Asp Asp Thr Ala Met Tyr Tyr Cys Ala
                85                  90                  95

Arg Ser Leu Tyr Gly Asn Ser Phe Asp His Trp Gly Gln Gly Thr Thr
            100                 105                 110

Leu Thr Val Ser Ser
        115
```

<210> SEQ ID NO 174
<211> LENGTH: 118
<212> TYPE: PRT
<213> ORGANISM: Artificial Sequence
<220> FEATURE:
<223> OTHER INFORMATION: Synthetic

<400> SEQUENCE: 174

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Gly Phe
            20                  25                  30

Leu Met His Trp Val Lys Gln Lys Pro Gly Gln Gly Leu Glu Trp Ile
```

```
                   35                  40                  45

Gly Tyr Ile Asn Pro Tyr Asn Asp Gly Thr Lys Tyr Ser Glu Arg Phe
             50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Asp Asp Ser Ala Val Tyr Tyr Cys
                 85                  90                  95

Ala Arg Leu Asp Tyr Gly Asn Ala Met Asp Tyr Trp Gly Gln Gly Thr
                100                 105                 110

Ser Val Thr Val Ser Ser
        115

<210> SEQ ID NO 175
<211> LENGTH: 119
<212> TYPE: PRT
<213> ORGANISM: Artificial Sequence
<220> FEATURE:
<223> OTHER INFORMATION: Synthetic

<400> SEQUENCE: 175

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Phe
             20                  25                  30

Gly Met His Trp Val Arg Gln Ala Pro Gly Lys Gly Leu Glu Trp Val
         35                  40                  45

Ser Tyr Ile Thr Ser Gly Asn Ser Pro Ile Tyr Phe Thr Asp Thr Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ser Tyr Tyr Gly Asn Ser Met Asp Tyr Trp Gly Gln Gly
                100                 105                 110

Thr Leu Val Thr Val Ser Ser
        115

<210> SEQ ID NO 176
<211> LENGTH: 119
<212> TYPE: PRT
<213> ORGANISM: Artificial Sequence
<220> FEATURE:
<223> OTHER INFORMATION: Synthetic

<400> SEQUENCE: 176

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Phe
             20                  25                  30

Gly Met His Trp Val Arg Gln Ala Pro Gly Lys Gly Leu Glu Trp Val
         35                  40                  45

Ala Tyr Ile Thr Ser Gly Asn Ser Pro Ile Tyr Phe Thr Asp Thr Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

-continued

Ala Arg Ser Ser Tyr Tyr Gly Asn Ser Met Asp Tyr Trp Gly Gln Gly
                100                 105                 110

Thr Leu Val Thr Val Ser Ser
        115

<210> SEQ ID NO 177
<211> LENGTH: 119
<212> TYPE: PRT
<213> ORGANISM: Artificial Sequence
<220> FEATURE:
<223> OTHER INFORMATION: Synthetic

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ala Tyr Ile Thr Ser Gly Asn Ser Pro Ile Tyr Phe Thr Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ser Met Asp Tyr Trp Gly Gln Gly
                100                 105                 110

Thr Leu Val Thr Val Ser Ser
        115

<210> SEQ ID NO 178
<211> LENGTH: 113
<212> TYPE: PRT
<213> ORGANISM: Artificial Sequence
<220> FEATURE:
<223> OTHER INFORMATION: Synthetic

<400> SEQUENCE: 178

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Asn Ser
            20                  25                  30

Gly Asn Arg Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Tyr Pro Phe Thr Phe Gly Gly Gly Thr Lys Leu Glu Ile
                100                 105                 110

Lys

<210> SEQ ID NO 179
<211> LENGTH: 113
<212> TYPE: PRT
<213> ORGANISM: Artificial Sequence
<220> FEATURE:

<223> OTHER INFORMATION: Synthetic

<400> SEQUENCE: 179

```
Asp Thr Val Met Thr Gln Ser Pro Asp Ser Leu Ala Val Ser Leu Gly
1               5                   10                  15
Glu Arg Ala Thr Ile Asn Cys Arg Ser Ser Gln Ser Leu Leu Asn Ser
            20                  25                  30
Gly Asn Arg Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Val Gln Ala Glu Asp Val Ala Val Tyr Tyr Cys Gln Asn
                85                  90                  95
Ala Tyr Ser Tyr Pro Phe Thr Phe Gly Gly Gly Thr Lys Leu Glu Ile
            100                 105                 110
Lys
```

<210> SEQ ID NO 180
<211> LENGTH: 113
<212> TYPE: PRT
<213> ORGANISM: Artificial Sequence
<220> FEATURE:
<223> OTHER INFORMATION: Synthetic

<400> SEQUENCE: 180

```
Asp Thr Val Met Thr Gln Ser Pro Asp Ser Leu Ala Val Ser Leu Gly
1               5                   10                  15
Glu Arg Val Thr Leu Asn Cys Arg Ser Ser Gln Ser Leu Leu Asn Ser
            20                  25                  30
Gly Asn Arg Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Val Gln Ala Glu Asp Val Ala Val Tyr Tyr Cys Gln Asn
                85                  90                  95
Ala Tyr Ser Tyr Pro Phe Thr Phe Gly Gly Gly Thr Lys Leu Glu Ile
            100                 105                 110
Lys
```

<210> SEQ ID NO 181
<211> LENGTH: 120
<212> TYPE: PRT
<213> ORGANISM: Artificial Sequence
<220> FEATURE:
<223> OTHER INFORMATION: Synthetic

<400> SEQUENCE: 181

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Thr Tyr
            20                  25                  30
Pro Ile Glu Trp Val Arg Gln Ala Pro Gly Gln Arg Leu Glu Trp Met
        35                  40                  45
```

Gly Asn Phe His Pro Tyr Asn Asp Asp Thr Lys Tyr Asn Glu Lys Phe
        50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Ala Tyr Gly Tyr Pro Tyr Ala Met Asp Tyr Trp Gly Gln
                100                 105                 110

Gly Thr Leu Val Thr Val Ser Ser
            115                 120

<210> SEQ ID NO 182
<211> LENGTH: 120
<212> TYPE: PRT
<213> ORGANISM: Artificial Sequence
<220> FEATURE:
<223> OTHER INFORMATION: Synthetic

<400> SEQUENCE: 182

Gln Val Gln Leu Val Gln Ser Gly Ala Glu Val Val Lys Pro Gly Ala
  1               5                  10                  15

Ser Val Lys Val Ser Cys Lys Ala Ser Gly Tyr Thr Phe Thr Thr Tyr
                 20                  25                  30

Pro Ile Glu Trp Met Arg Gln Ala Pro Gly Gln Arg Leu Glu Trp Met
             35                  40                  45

Gly Asn Phe His Pro Tyr Asn Asp Asp Thr Lys Tyr Asn Glu Lys Phe
        50                  55                  60

Lys Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Ala Tyr Gly Tyr Pro Tyr Ala Met Asp Tyr Trp Gly Gln
                100                 105                 110

Gly Thr Leu Val Thr Val Ser Ser
            115                 120

<210> SEQ ID NO 183
<211> LENGTH: 120
<212> TYPE: PRT
<213> ORGANISM: Artificial Sequence
<220> FEATURE:
<223> OTHER INFORMATION: Synthetic

<400> SEQUENCE: 183

Gln Val Gln Leu Val Gln Ser Gly Ala Glu Val Val Lys Pro Gly Ala
  1               5                  10                  15

Ser Val Lys Val Ser Cys Lys Ala Ser Gly Tyr Thr Phe Thr Thr Tyr
                 20                  25                  30

Pro Ile Glu Trp Met Lys Gln Ala Pro Gly Gln Arg Leu Glu Trp Met
             35                  40                  45

Gly Asn Phe His Pro Tyr Asn Asp Asp Thr Lys Tyr Asn Glu Lys Phe
        50                  55                  60

Lys Gly Arg Val Thr Ile Thr Val Asp Thr Ser Ala Ser Thr Ala Tyr
 65                  70                  75                  80

Met Glu Val Ser Ser Leu Arg Ser Glu Asp Thr Ala Val Tyr Tyr Cys
                 85                  90                  95

Ala Arg Arg Ala Tyr Gly Tyr Pro Tyr Ala Met Asp Tyr Trp Gly Gln
                100                 105                 110

```
Gly Thr Leu Val Thr Val Ser Ser
        115                 120

<210> SEQ ID NO 184
<211> LENGTH: 120
<212> TYPE: PRT
<213> ORGANISM: Artificial Sequence
<220> FEATURE:
<223> OTHER INFORMATION: Synthetic

<400> SEQUENCE: 184

Gln Val Gln Leu Val Gln Ser Gly Ala Glu Val Lys Pro Gly Ala
1               5                   10                  15

Ser Val Lys Met Ser Cys Lys Ala Ser Gly Tyr Thr Phe Thr Thr Tyr
            20                  25                  30

Pro Ile Glu Trp Met Lys Gln Ala Pro Gly Gln Arg Leu Glu Trp Met
        35                  40                  45

Gly Asn Phe His Pro Tyr Asn Asp Asp Thr Lys Tyr Asn Glu Lys Phe
    50                  55                  60

Lys Gly Arg Val Thr Leu Thr Val Asp Thr Ser Ala Ser Thr Val Tyr
65                  70                  75                  80

Leu Glu Val Ser Ser Leu Arg Ser Glu Asp Thr Ala Val Tyr Tyr Cys
                85                  90                  95

Ala Arg Arg Ala Tyr Gly Tyr Pro Tyr Ala Met Asp Tyr Trp Gly Gln
            100                 105                 110

Gly Thr Leu Val Thr Val Ser Ser
        115                 120

<210> SEQ ID NO 185
<211> LENGTH: 113
<212> TYPE: PRT
<213> ORGANISM: Artificial Sequence
<220> FEATURE:
<223> OTHER INFORMATION: Synthetic

<400> SEQUENCE: 185

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Arg Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ile Tyr Pro Tyr Thr Phe Gly Gly Gly Thr Lys Leu Glu Ile
            100                 105                 110

Lys

<210> SEQ ID NO 186
<211> LENGTH: 113
<212> TYPE: PRT
<213> ORGANISM: Artificial Sequence
<220> FEATURE:
<223> OTHER INFORMATION: Synthetic
```

<400> SEQUENCE: 186

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Arg Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ile Tyr Pro Tyr Thr Phe Gly Gly Gly Thr Lys Leu Glu Ile
            100                 105                 110

Lys

<210> SEQ ID NO 187
<211> LENGTH: 113
<212> TYPE: PRT
<213> ORGANISM: Artificial Sequence
<220> FEATURE:
<223> OTHER INFORMATION: Synthetic

<400> SEQUENCE: 187

Asp Ile Val Met Thr Gln Ser Pro Asp Ser Leu Ala Val Ser Leu Gly
1               5                   10                  15

Glu Arg Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Arg Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Asn
                85                  90                  95

Asp Tyr Ile Tyr Pro Tyr Thr Phe Gly Gly Gly Thr Lys Leu Glu Ile
            100                 105                 110

Lys

<210> SEQ ID NO 188
<211> LENGTH: 118
<212> TYPE: PRT
<213> ORGANISM: Artificial Sequence
<220> FEATURE:
<223> OTHER INFORMATION: Synthetic

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Ile Gln Trp Val Arg Gln Ala Pro Gly Gln Arg Leu Glu Trp Met
        35                  40                  45

Gly Phe Ile Asn Pro Tyr Asn Asp Gly Thr Lys Tyr Asn Glu Gln Phe
    50                  55                  60

```
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Tyr Phe Gly Asn Ser Phe Ala Tyr Trp Gly Gln Gly Thr
                100                 105                 110

Leu Val Thr Val Ser Ser
            115
```

<210> SEQ ID NO 189
<211> LENGTH: 118
<212> TYPE: PRT
<213> ORGANISM: Artificial Sequence
<220> FEATURE:
<223> OTHER INFORMATION: Synthetic

<400> SEQUENCE: 189

```
Gln Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Gly Tyr
                 20                  25                  30

Ile Ile Gln Trp Met Arg Gln Ala Pro Gly Gln Arg Leu Glu Trp Met
             35                  40                  45

Gly Phe Ile Asn Pro Tyr Asn Asp Gly Thr Lys Tyr Asn Glu Gln Phe
         50                  55                  60

Lys Gly Arg Val Thr Ile Thr Ser Asp Thr Ser Ala Ser Ala Ala Tyr
 65                  70                  75                  80

Met Glu Leu Ser Ser Leu Arg Ser Glu Asp Thr Ala Val Tyr Tyr Cys
                 85                  90                  95

Ala Arg Ala Tyr Phe Gly Asn Ser Phe Ala Tyr Trp Gly Gln Gly Thr
                100                 105                 110

Leu Val Thr Val Ser Ser
            115
```

<210> SEQ ID NO 190
<211> LENGTH: 118
<212> TYPE: PRT
<213> ORGANISM: Artificial Sequence
<220> FEATURE:
<223> OTHER INFORMATION: Synthetic

<400> SEQUENCE: 190

```
Gln Val Gln Leu Val Gln Ser Gly Ala Glu Val Val Lys Pro Gly Ala
 1               5                  10                  15

Ser Val Lys Val Ser Cys Lys Ala Ser Gly Tyr Thr Phe Thr Gly Tyr
                 20                  25                  30

Ile Ile Gln Trp Met Lys Gln Ala Pro Gly Gln Arg Leu Glu Trp Ile
             35                  40                  45

Gly Phe Ile Asn Pro Tyr Asn Asp Gly Thr Lys Tyr Asn Glu Gln Phe
         50                  55                  60

Lys Gly Arg Ala Thr Ile Thr Ser Asp Thr Ser Ala Ser Ala Ala Tyr
 65                  70                  75                  80

Met Glu Leu Ser Ser Leu Arg Ser Glu Asp Thr Ala Val Tyr Tyr Cys
                 85                  90                  95

Ala Arg Ala Tyr Phe Gly Asn Ser Phe Ala Tyr Trp Gly Gln Gly Thr
                100                 105                 110

Leu Val Thr Val Ser Ser
```

-continued

```
              115

<210> SEQ ID NO 191
<211> LENGTH: 118
<212> TYPE: PRT
<213> ORGANISM: Artificial Sequence
<220> FEATURE:
<223> OTHER INFORMATION: Synthetic

<400> SEQUENCE: 191

Glu Val Gln Leu Val Gln Ser Gly Ala Glu Val Lys Pro Gly Ala
1               5                   10                  15

Ser Val Lys Met Ser Cys Lys Ala Ser Gly Tyr Thr Phe Thr Gly Tyr
                20                  25                  30

Ile Ile Gln Trp Met Lys Gln Ala Pro Gly Gln Arg Leu Glu Trp Ile
            35                  40                  45

Gly Phe Ile Asn Pro Tyr Asn Asp Gly Thr Lys Tyr Asn Glu Gln Phe
        50                  55                  60

Lys Gly Arg Ala Thr Leu Thr Ser Asp Thr Ser Ala Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Phe Gly Asn Ser Phe Ala Tyr Trp Gly Gln Gly Thr
                100                 105                 110

Leu Val Thr Val Ser Ser
            115

<210> SEQ ID NO 192
<211> LENGTH: 113
<212> TYPE: PRT
<213> ORGANISM: Artificial Sequence
<220> FEATURE:
<223> OTHER INFORMATION: Synthetic

<400> SEQUENCE: 192

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Gly Tyr Tyr Phe Pro Phe Thr Phe Gly Gly Gly Thr Lys Leu Glu Ile
                100                 105                 110

Lys

<210> SEQ ID NO 193
<211> LENGTH: 113
<212> TYPE: PRT
<213> ORGANISM: Artificial Sequence
<220> FEATURE:
<223> OTHER INFORMATION: Synthetic

<400> SEQUENCE: 193
```

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Gly Tyr Tyr Phe Pro Phe Thr Phe Gly Gly Gly Thr Lys Leu Glu Ile
            100                 105                 110

Lys

<210> SEQ ID NO 194
<211> LENGTH: 113
<212> TYPE: PRT
<213> ORGANISM: Artificial Sequence
<220> FEATURE:
<223> OTHER INFORMATION: Synthetic

<400> SEQUENCE: 194

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Gly Gln Ala Glu Asp Val Ala Val Tyr Phe Cys Gln Asn
                85                  90                  95

Gly Tyr Tyr Phe Pro Phe Thr Phe Gly Gly Gly Thr Lys Leu Glu Ile
            100                 105                 110

Lys

<210> SEQ ID NO 195
<211> LENGTH: 113
<212> TYPE: PRT
<213> ORGANISM: Artificial Sequence
<220> FEATURE:
<223> OTHER INFORMATION: Synthetic

<400> SEQUENCE: 195

Asp Ile Val Met Thr Gln Ser Pro Asp Ser Leu Ala Val Ser Leu Gly
1               5                   10                  15

Glu Arg Val Thr Met Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Met Tyr Trp Ala Ser Thr Arg Glu Ser Gly Val
    50                  55                  60

Pro Asp Arg Phe Ser Gly Ser Gly Ser Gly Thr Asp Phe Thr Leu Thr

```
            65                  70                  75                  80

Ile Ser Ser Gly Gln Ala Glu Asp Val Ala Val Tyr Phe Cys Gln Asn
                85                  90                  95

Gly Tyr Tyr Phe Pro Phe Thr Phe Gly Gly Gly Thr Lys Leu Glu Ile
            100                 105                 110

Lys

<210> SEQ ID NO 196
<211> LENGTH: 119
<212> TYPE: PRT
<213> ORGANISM: Artificial Sequence
<220> FEATURE:
<223> OTHER INFORMATION: Synthetic

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ser Tyr Ile Thr Ser Gly Gln Ser Pro Ile Tyr Phe Thr Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ser Met Asp Tyr Trp Gly Gln Gly
            100                 105                 110

Thr Leu Val Thr Val Ser Ser
        115

<210> SEQ ID NO 197
<211> LENGTH: 119
<212> TYPE: PRT
<213> ORGANISM: Artificial Sequence
<220> FEATURE:
<223> OTHER INFORMATION: Synthetic

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ser Tyr Ile Thr Ser Gly Glu Ser Pro Ile Tyr Phe Thr Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ser Met Asp Tyr Trp Gly Gln Gly
            100                 105                 110

Thr Leu Val Thr Val Ser Ser
        115
```

```
<210> SEQ ID NO 198
<211> LENGTH: 119
<212> TYPE: PRT
<213> ORGANISM: Artificial Sequence
<220> FEATURE:
<223> OTHER INFORMATION: Synthetic

<400> SEQUENCE: 198
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ser Tyr Ile Thr Ser Gly Glu Ser Pro Ile Tyr Phe Thr Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Gln Ser Met Asp Tyr Trp Gly Gln Gly
            100                 105                 110

Thr Leu Val Thr Val Ser Ser
        115

```
<210> SEQ ID NO 199
<211> LENGTH: 119
<212> TYPE: PRT
<213> ORGANISM: Artificial Sequence
<220> FEATURE:
<223> OTHER INFORMATION: Synthetic

<400> SEQUENCE: 199
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ser Tyr Ile Thr Ser Gly Glu Ser Pro Ile Tyr Phe Thr Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Gln Ser Met Asp Tyr Trp Gly Gln Gly
            100                 105                 110

Thr Leu Val Thr Val Ser Ser
        115

```
<210> SEQ ID NO 200
<211> LENGTH: 119
<212> TYPE: PRT
<213> ORGANISM: Artificial Sequence
<220> FEATURE:
<223> OTHER INFORMATION: Synthetic

<400> SEQUENCE: 200
```

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Thr Phe
            20                  25                  30

Gly Met His Trp Val Arg Gln Ala Pro Gly Lys Gly Leu Glu Trp Val
        35                  40                  45

Ser Tyr Ile Thr Ser Gly Glu Ser Pro Ile Tyr Phe Thr Asp Thr Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Asn Ala Met Asp Tyr Trp Gly Gln Gly
            100                 105                 110

Thr Leu Val Thr Val Ser Ser
        115
```

<210> SEQ ID NO 201
<211> LENGTH: 113
<212> TYPE: PRT
<213> ORGANISM: Artificial Sequence
<220> FEATURE:
<223> OTHER INFORMATION: Synthetic

<400> SEQUENCE: 201

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Glu Ser
            20                  25                  30

Gly Asn Arg Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Ser Tyr Pro Phe Thr Phe Gly Gly Thr Lys Leu Glu Ile
            100                 105                 110

Lys
```

<210> SEQ ID NO 202
<211> LENGTH: 113
<212> TYPE: PRT
<213> ORGANISM: Artificial Sequence
<220> FEATURE:
<223> OTHER INFORMATION: Synthetic

<400> SEQUENCE: 202

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Asn Ala
            20                  25                  30

Gly Asn Arg Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

Ile Ser Ser Leu Gln Ala Glu Asp Val Ala Val Tyr Tyr Cys Gln Asn
                85                  90                  95

Ala Tyr Ser Tyr Pro Phe Thr Phe Gly Gly Gly Thr Lys Leu Glu Ile
            100                 105                 110

Lys

<210> SEQ ID NO 203
<211> LENGTH: 113
<212> TYPE: PRT
<213> ORGANISM: Artificial Sequence
<220> FEATURE:
<223> OTHER INFORMATION: Synthetic

<400> SEQUENCE: 203

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Arg Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ile Tyr Pro Tyr Thr Phe Gly Gly Gly Thr Lys Leu Glu Ile
            100                 105                 110

Lys

<210> SEQ ID NO 204
<211> LENGTH: 113
<212> TYPE: PRT
<213> ORGANISM: Artificial Sequence
<220> FEATURE:
<223> OTHER INFORMATION: Synthetic

<400> SEQUENCE: 204

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Glu Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Arg Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ile Tyr Pro Tyr Thr Phe Gly Gly Gly Thr Lys Leu Glu Ile
            100                 105                 110

Lys

<210> SEQ ID NO 205
<211> LENGTH: 118
<212> TYPE: PRT

-continued

<213> ORGANISM: Artificial Sequence
<220> FEATURE:
<223> OTHER INFORMATION: Synthetic

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Ile Gln Trp Val Arg Gln Ala Pro Gly Gln Arg Leu Glu Trp Met
        35                  40                  45

Gly Phe Ile Asn Pro Tyr Asn Asp Asp Thr Lys Tyr Asn Glu Gln Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Tyr Phe Gly Asn Ala Phe Ala Tyr Trp Gly Gln Gly Thr
            100                 105                 110

Leu Val Thr Val Ser Ser
        115

<210> SEQ ID NO 206
<211> LENGTH: 113
<212> TYPE: PRT
<213> ORGANISM: Artificial Sequence
<220> FEATURE:
<223> OTHER INFORMATION: Synthetic

<400> SEQUENCE: 206

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ala
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Tyr Phe Pro Phe Thr Phe Gly Gly Gly Thr Lys Leu Glu Ile
            100                 105                 110

Lys

<210> SEQ ID NO 207
<211> LENGTH: 113
<212> TYPE: PRT
<213> ORGANISM: Artificial Sequence
<220> FEATURE:
<223> OTHER INFORMATION: Synthetic

<400> SEQUENCE: 207

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Glu Ser
            20                  25                  30

```
Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Glu
                 85                  90                  95

Gly Tyr Tyr Phe Pro Phe Thr Phe Gly Gly Gly Thr Lys Leu Glu Ile
                100                 105                 110

Lys

<210> SEQ ID NO 208
<211> LENGTH: 17
<212> TYPE: PRT
<213> ORGANISM: Artificial Sequence
<220> FEATURE:
<223> OTHER INFORMATION: Synthetic

<400> SEQUENCE: 208

Lys Ser Ser Gln Ser Leu Leu Asn Ser Gly Asn Gln Arg Asn Tyr Leu
 1               5                  10                  15

Thr

<210> SEQ ID NO 209
<211> LENGTH: 17
<212> TYPE: PRT
<213> ORGANISM: Artificial Sequence
<220> FEATURE:
<223> OTHER INFORMATION: Synthetic

<400> SEQUENCE: 209

Lys Ser Ser Gln Ser Leu Leu Asn Ser Gly Asn Leu Lys Asn Tyr Leu
 1               5                  10                  15

Thr

<210> SEQ ID NO 210
<211> LENGTH: 17
<212> TYPE: PRT
<213> ORGANISM: Artificial Sequence
<220> FEATURE:
<223> OTHER INFORMATION: Synthetic

<400> SEQUENCE: 210

Lys Ser Ser Gln Ser Leu Leu Asn Ser Gly Asn Gln Lys Asn Tyr Leu
 1               5                  10                  15

Thr

<210> SEQ ID NO 211
<211> LENGTH: 17
<212> TYPE: PRT
<213> ORGANISM: Artificial Sequence
<220> FEATURE:
<223> OTHER INFORMATION: Synthetic

<400> SEQUENCE: 211

Lys Ser Ser Gln Ser Leu Leu Asn Gly Gly Asn Gln Lys Asn Tyr Leu
 1               5                  10                  15

Ala

<210> SEQ ID NO 212
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 212

Lys Ser Asn Gln Ser Leu Leu Asn Ser Gly Asn Gln Lys Lys Tyr Leu
1               5                   10                  15
Thr

<210> SEQ ID NO 213
<211> LENGTH: 17
<212> TYPE: PRT
<213> ORGANISM: Artificial Sequence
<220> FEATURE:
<223> OTHER INFORMATION: Synthetic

<400> SEQUENCE: 213

Lys Ser Ser Gln Ser Leu Phe Asn Ser Gly Asn Gln Arg Asn Tyr Leu
1               5                   10                  15
Thr

<210> SEQ ID NO 214
<211> LENGTH: 17
<212> TYPE: PRT
<213> ORGANISM: Artificial Sequence
<220> FEATURE:
<223> OTHER INFORMATION: Synthetic

<400> SEQUENCE: 214

Arg Ser Ser Met Ser Leu Phe Asn Ser Gly Asn Gln Lys Ser Tyr Leu
1               5                   10                  15
Ser

<210> SEQ ID NO 215
<211> LENGTH: 17
<212> TYPE: PRT
<213> ORGANISM: Artificial Sequence
<220> FEATURE:
<223> OTHER INFORMATION: Synthetic

<400> SEQUENCE: 215

Arg Ser Ile Gln Ser Leu Leu Asn Ser Gly Asn Gln Lys Asn Tyr Leu
1               5                   10                  15
Ser

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Arg Ser Ser Gln Ser Leu Leu Asn Ser Gly Asn Arg Lys Asn Tyr Leu
1               5                   10                  15
Thr

<210> SEQ ID NO 217
<211> LENGTH: 17
<212> TYPE: PRT
<213> ORGANISM: Artificial Sequence
<220> FEATURE:
```

<223> OTHER INFORMATION: Synthetic

<400> SEQUENCE: 217

Arg Ser Thr Gln Ser Leu Phe Asn Ser Gly Asn Gln Lys Asn Tyr Leu
1               5                   10                  15
Thr

<210> SEQ ID NO 218
<211> LENGTH: 17
<212> TYPE: PRT
<213> ORGANISM: Artificial Sequence
<220> FEATURE:
<223> OTHER INFORMATION: Synthetic

<400> SEQUENCE: 218

Lys Pro Ser Gln Ser Leu Leu Asn Ser Gly Asn Gln Lys Asn Tyr Leu
1               5                   10                  15
Ala

<210> SEQ ID NO 219
<211> LENGTH: 17
<212> TYPE: PRT
<213> ORGANISM: Artificial Sequence
<220> FEATURE:
<223> OTHER INFORMATION: Synthetic

<400> SEQUENCE: 219

Arg Ser Thr Gln Ser Leu Phe Asn Ser Gly Asn Gln Arg Asn Tyr Leu
1               5                   10                  15
Thr

<210> SEQ ID NO 220
<211> LENGTH: 17
<212> TYPE: PRT
<213> ORGANISM: Artificial Sequence
<220> FEATURE:
<223> OTHER INFORMATION: Synthetic

<400> SEQUENCE: 220

Lys Ser Ser Gln Ser Leu Leu Asn Ser Gly Asn Gln Lys Asn Tyr Leu
1               5                   10                  15
Ala

<210> SEQ ID NO 221
<211> LENGTH: 17
<212> TYPE: PRT
<213> ORGANISM: Artificial Sequence
<220> FEATURE:
<223> OTHER INFORMATION: Synthetic

<400> SEQUENCE: 221

Lys Ser Ser Gln Ser Val Phe Asn Ser Gly Asn Gln Lys Asn Tyr Leu
1               5                   10                  15
Thr

<210> SEQ ID NO 222
<211> LENGTH: 17
<212> TYPE: PRT
<213> ORGANISM: Artificial Sequence
<220> FEATURE:
<223> OTHER INFORMATION: Synthetic

<400> SEQUENCE: 222

Arg Ser Ser Gln Ser Leu Leu Asn Gly Gly Asn Gln Lys Asn Tyr Leu
1               5                   10                  15

Thr

<210> SEQ ID NO 223
<211> LENGTH: 17
<212> TYPE: PRT
<213> ORGANISM: Artificial Sequence
<220> FEATURE:
<223> OTHER INFORMATION: Synthetic

<400> SEQUENCE: 223

Lys Ser Ser Gln Ser Leu Leu Asn Ser Gly Asn Gln Arg Asn Tyr Leu
1               5                   10                  15

Ser

<210> SEQ ID NO 224
<211> LENGTH: 17
<212> TYPE: PRT
<213> ORGANISM: Artificial Sequence
<220> FEATURE:
<223> OTHER INFORMATION: Synthetic

<400> SEQUENCE: 224

Lys Ser Ser Gln Ser Leu Phe Asn Ser Gly Asn Gln Lys Asn Tyr Leu
1               5                   10                  15

Thr

<210> SEQ ID NO 225
<211> LENGTH: 17
<212> TYPE: PRT
<213> ORGANISM: Artificial Sequence
<220> FEATURE:
<223> OTHER INFORMATION: Synthetic

<400> SEQUENCE: 225

Arg Ser Ser Gln Ser Leu Phe Asn Ser Gly Asn Gln Arg Asn Tyr Leu
1               5                   10                  15

Thr

<210> SEQ ID NO 226
<211> LENGTH: 17
<212> TYPE: PRT
<213> ORGANISM: Artificial Sequence
<220> FEATURE:
<223> OTHER INFORMATION: Synthetic

<400> SEQUENCE: 226

Lys Ser Thr Gln Ser Leu Leu Asn Ser Gly Asn Gln Arg Asn Tyr Leu
1               5                   10                  15

Thr

<210> SEQ ID NO 227
<211> LENGTH: 7
<212> TYPE: PRT
<213> ORGANISM: Artificial Sequence
<220> FEATURE:
<223> OTHER INFORMATION: Synthetic

<400> SEQUENCE: 227

Trp Ala Ser Thr Arg Glu Ser
1               5

```
<210> SEQ ID NO 228
<211> LENGTH: 7
<212> TYPE: PRT
<213> ORGANISM: Artificial Sequence
<220> FEATURE:
<223> OTHER INFORMATION: Synthetic

<400> SEQUENCE: 228

Gly Ala Ser Thr Arg Glu Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Synthetic

<400> SEQUENCE: 229

Arg Ala Ser Ser Arg Glu Ser
1               5

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

Trp Ala Phe Thr Arg Glu Ser
1               5

<210> SEQ ID NO 231
<211> LENGTH: 7
<212> TYPE: PRT
<213> ORGANISM: Artificial Sequence
<220> FEATURE:
<223> OTHER INFORMATION: Synthetic

<400> SEQUENCE: 231

Trp Ser Ser Thr Arg Asp Ser
1               5

<210> SEQ ID NO 232
<211> LENGTH: 7
<212> TYPE: PRT
<213> ORGANISM: Artificial Sequence
<220> FEATURE:
<223> OTHER INFORMATION: Synthetic

<400> SEQUENCE: 232

Trp Ala Ser Thr Arg Asp Ser
1               5

<210> SEQ ID NO 233
<211> LENGTH: 7
<212> TYPE: PRT
<213> ORGANISM: Artificial Sequence
<220> FEATURE:
<223> OTHER INFORMATION: Synthetic

<400> SEQUENCE: 233

Trp Ser Ser Thr Arg Glu Ser
1               5

<210> SEQ ID NO 234
```

<211> LENGTH: 5
<212> TYPE: PRT
<213> ORGANISM: Artificial Sequence
<220> FEATURE:
<223> OTHER INFORMATION: Synthetic

<400> SEQUENCE: 234

Asn Tyr Leu Leu Glu
1               5

<210> SEQ ID NO 235
<211> LENGTH: 5
<212> TYPE: PRT
<213> ORGANISM: Artificial Sequence
<220> FEATURE:
<223> OTHER INFORMATION: Synthetic

<400> SEQUENCE: 235

Ser Tyr Gly Val Ser
1               5

<210> SEQ ID NO 236
<211> LENGTH: 5
<212> TYPE: PRT
<213> ORGANISM: Artificial Sequence
<220> FEATURE:
<223> OTHER INFORMATION: Synthetic

<400> SEQUENCE: 236

Ser Phe Gly Met Asn
1               5

<210> SEQ ID NO 237
<211> LENGTH: 5
<212> TYPE: PRT
<213> ORGANISM: Artificial Sequence
<220> FEATURE:
<223> OTHER INFORMATION: Synthetic

<400> SEQUENCE: 237

Thr Asn Ala Met Asn
1               5

<210> SEQ ID NO 238
<211> LENGTH: 5
<212> TYPE: PRT
<213> ORGANISM: Artificial Sequence
<220> FEATURE:
<223> OTHER INFORMATION: Synthetic

<400> SEQUENCE: 238

Thr Tyr Ser Ile His
1               5

<210> SEQ ID NO 239
<211> LENGTH: 5
<212> TYPE: PRT
<213> ORGANISM: Artificial Sequence
<220> FEATURE:
<223> OTHER INFORMATION: Synthetic

<400> SEQUENCE: 239

Asn Tyr Gly Met Ser
1               5

<210> SEQ ID NO 240
<211> LENGTH: 5

```
<212> TYPE: PRT
<213> ORGANISM: Artificial Sequence
<220> FEATURE:
<223> OTHER INFORMATION: Synthetic

<400> SEQUENCE: 240

Asn Tyr Gly Met Asn
1               5

<210> SEQ ID NO 241
<211> LENGTH: 5
<212> TYPE: PRT
<213> ORGANISM: Artificial Sequence
<220> FEATURE:
<223> OTHER INFORMATION: Synthetic

<400> SEQUENCE: 241

Lys Tyr Gly Met Asn
1               5

<210> SEQ ID NO 242
<211> LENGTH: 5
<212> TYPE: PRT
<213> ORGANISM: Artificial Sequence
<220> FEATURE:
<223> OTHER INFORMATION: Synthetic

<400> SEQUENCE: 242

Thr Tyr Pro Ile Glu
1               5

<210> SEQ ID NO 243
<211> LENGTH: 5
<212> TYPE: PRT
<213> ORGANISM: Artificial Sequence
<220> FEATURE:
<223> OTHER INFORMATION: Synthetic

<400> SEQUENCE: 243

Asn Tyr Leu Ile Glu
1               5

<210> SEQ ID NO 244
<211> LENGTH: 5
<212> TYPE: PRT
<213> ORGANISM: Artificial Sequence
<220> FEATURE:
<223> OTHER INFORMATION: Synthetic

<400> SEQUENCE: 244

Ser Tyr Gly Val His
1               5

<210> SEQ ID NO 245
<211> LENGTH: 5
<212> TYPE: PRT
<213> ORGANISM: Artificial Sequence
<220> FEATURE:
<223> OTHER INFORMATION: Synthetic

<400> SEQUENCE: 245

Ser Phe Gly Val His
1               5

<210> SEQ ID NO 246
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 246

Thr Phe Gly Met His
1               5

<210> SEQ ID NO 247
<211> LENGTH: 5
<212> TYPE: PRT
<213> ORGANISM: Artificial Sequence
<220> FEATURE:
<223> OTHER INFORMATION: Synthetic

<400> SEQUENCE: 247

Thr Tyr Gly Val His
1               5

<210> SEQ ID NO 248
<211> LENGTH: 5
<212> TYPE: PRT
<213> ORGANISM: Artificial Sequence
<220> FEATURE:
<223> OTHER INFORMATION: Synthetic

<400> SEQUENCE: 248

Asn Tyr Gly Val Ser
1               5

<210> SEQ ID NO 249
<211> LENGTH: 5
<212> TYPE: PRT
<213> ORGANISM: Artificial Sequence
<220> FEATURE:
<223> OTHER INFORMATION: Synthetic

<400> SEQUENCE: 249

Gly Phe Leu Met His
1               5

<210> SEQ ID NO 250
<211> LENGTH: 5
<212> TYPE: PRT
<213> ORGANISM: Artificial Sequence
<220> FEATURE:
<223> OTHER INFORMATION: Synthetic

<400> SEQUENCE: 250

Lys Tyr Gly Val His
1               5

<210> SEQ ID NO 251
<211> LENGTH: 5
<212> TYPE: PRT
<213> ORGANISM: Artificial Sequence
<220> FEATURE:
<223> OTHER INFORMATION: Synthetic

<400> SEQUENCE: 251

Ser Gly Tyr Phe Trp
1               5

<210> SEQ ID NO 252
<211> LENGTH: 5
<212> TYPE: PRT
<213> ORGANISM: Artificial Sequence
```

```
<220> FEATURE:
<223> OTHER INFORMATION: Synthetic

<400> SEQUENCE: 252

Asn Phe Leu Thr His
1               5

<210> SEQ ID NO 253
<211> LENGTH: 5
<212> TYPE: PRT
<213> ORGANISM: Artificial Sequence
<220> FEATURE:
<223> OTHER INFORMATION: Synthetic

<400> SEQUENCE: 253

Gly Tyr Ile Ile Gln
1               5

<210> SEQ ID NO 254
<211> LENGTH: 5
<212> TYPE: PRT
<213> ORGANISM: Artificial Sequence
<220> FEATURE:
<223> OTHER INFORMATION: Synthetic

<400> SEQUENCE: 254

Ser Tyr Gly Ala His
1               5

<210> SEQ ID NO 255
<211> LENGTH: 17
<212> TYPE: PRT
<213> ORGANISM: Artificial Sequence
<220> FEATURE:
<223> OTHER INFORMATION: Synthetic

<400> SEQUENCE: 255

Glu Ile Asn Pro Gly Asn Gly Gly Ser Asn Tyr Asn Glu Lys Phe Lys
1               5                   10                  15

Gly

<210> SEQ ID NO 256
<211> LENGTH: 16
<212> TYPE: PRT
<213> ORGANISM: Artificial Sequence
<220> FEATURE:
<223> OTHER INFORMATION: Synthetic

<400> SEQUENCE: 256

Val Ile Trp Gly Asp Gly Asn Thr Ile Tyr His Ser Ala Leu Lys Ser
1               5                   10                  15

<210> SEQ ID NO 257
<211> LENGTH: 17
<212> TYPE: PRT
<213> ORGANISM: Artificial Sequence
<220> FEATURE:
<223> OTHER INFORMATION: Synthetic

<400> SEQUENCE: 257

Phe Ile Ser Gly Gly Ser Asn Thr Ile His Tyr Leu Asp Thr Val Lys
1               5                   10                  15

Gly

<210> SEQ ID NO 258
```

```
<211> LENGTH: 19
<212> TYPE: PRT
<213> ORGANISM: Artificial Sequence
<220> FEATURE:
<223> OTHER INFORMATION: Synthetic

<400> SEQUENCE: 258

Arg Ile Arg Ser Lys Ser Asn Asn Tyr Ala Thr Tyr Tyr Ala Asp Ser
1               5                   10                  15

Val Lys Asp

<210> SEQ ID NO 259
<211> LENGTH: 17
<212> TYPE: PRT
<213> ORGANISM: Artificial Sequence
<220> FEATURE:
<223> OTHER INFORMATION: Synthetic

<400> SEQUENCE: 259

Tyr Ile Asn Pro Ser Thr Ile Tyr Thr Asn Tyr Asn Gln Lys Phe Lys
1               5                   10                  15

Tyr

<210> SEQ ID NO 260
<211> LENGTH: 17
<212> TYPE: PRT
<213> ORGANISM: Artificial Sequence
<220> FEATURE:
<223> OTHER INFORMATION: Synthetic

<400> SEQUENCE: 260

Thr Phe Ser Tyr Gly Asp Ser His Asn Tyr Tyr Ser Asp Ser Val Lys
1               5                   10                  15

Gly

<210> SEQ ID NO 261
<211> LENGTH: 17
<212> TYPE: PRT
<213> ORGANISM: Artificial Sequence
<220> FEATURE:
<223> OTHER INFORMATION: Synthetic

<400> SEQUENCE: 261

Trp Ile Asn Ala Asn Thr Gly Glu Pro Thr Tyr Ala Glu Glu Phe Lys
1               5                   10                  15

Gly

<210> SEQ ID NO 262
<211> LENGTH: 17
<212> TYPE: PRT
<213> ORGANISM: Artificial Sequence
<220> FEATURE:
<223> OTHER INFORMATION: Synthetic

<400> SEQUENCE: 262

Trp Ile Ser Thr Asn Thr Gly Glu Pro Thr Tyr Ala Glu Glu Phe Lys
1               5                   10                  15

Gly

<210> SEQ ID NO 263
<211> LENGTH: 17
<212> TYPE: PRT
<213> ORGANISM: Artificial Sequence
<220> FEATURE:
```

<223> OTHER INFORMATION: Synthetic

<400> SEQUENCE: 263

Asn Phe His Pro Tyr Asn Asp Asp Thr Lys Tyr Asn Glu Lys Phe Lys
1               5                   10                  15

Gly

<210> SEQ ID NO 264
<211> LENGTH: 17
<212> TYPE: PRT
<213> ORGANISM: Artificial Sequence
<220> FEATURE:
<223> OTHER INFORMATION: Synthetic

<400> SEQUENCE: 264

Val Ile Asn Pro Gly Arg Ser Gly Thr Asn Tyr Asn Glu Lys Phe Lys
1               5                   10                  15

Gly

<210> SEQ ID NO 265
<211> LENGTH: 16
<212> TYPE: PRT
<213> ORGANISM: Artificial Sequence
<220> FEATURE:
<223> OTHER INFORMATION: Synthetic

<400> SEQUENCE: 265

Val Ile Trp Ala Gly Gly Ser Thr Asn Tyr Asp Ser Ala Leu Met Ser
1               5                   10                  15

<210> SEQ ID NO 266
<211> LENGTH: 16
<212> TYPE: PRT
<213> ORGANISM: Artificial Sequence
<220> FEATURE:
<223> OTHER INFORMATION: Synthetic

<400> SEQUENCE: 266

Val Ile Trp Ala Gly Gly Ser Thr Asn Tyr Asn Ser Ala Leu Met Ser
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Synthetic

<400> SEQUENCE: 267

Val Ile Trp Ala Gly Arg Thr Asn Tyr Asn Ser Ala Leu Met Ser
1               5                   10                  15

<210> SEQ ID NO 268
<211> LENGTH: 17
<212> TYPE: PRT
<213> ORGANISM: Artificial Sequence
<220> FEATURE:
<223> OTHER INFORMATION: Synthetic

<400> SEQUENCE: 268

Tyr Ile Thr Ser Gly Asn Ser Pro Ile Tyr Phe Thr Asp Thr Val Lys
1               5                   10                  15

Gly

```
<210> SEQ ID NO 269
<211> LENGTH: 16
<212> TYPE: PRT
<213> ORGANISM: Artificial Sequence
<220> FEATURE:
<223> OTHER INFORMATION: Synthetic

<400> SEQUENCE: 269

Val Met Leu Ser Asp Gly Asn Thr Val Tyr Asn Ser Ser Leu Lys Ser
1               5                   10                  15

<210> SEQ ID NO 270
<211> LENGTH: 16
<212> TYPE: PRT
<213> ORGANISM: Artificial Sequence
<220> FEATURE:
<223> OTHER INFORMATION: Synthetic

<400> SEQUENCE: 270

Val Ile Trp Gly Asp Gly Asn Thr Asn Tyr Gln Ser Ala Leu Arg Ser
1               5                   10                  15

<210> SEQ ID NO 271
<211> LENGTH: 16
<212> TYPE: PRT
<213> ORGANISM: Artificial Sequence
<220> FEATURE:
<223> OTHER INFORMATION: Synthetic

<400> SEQUENCE: 271

Val Ile Arg Gly Asp Gly Asn Thr Asn Tyr Gln Ser Ala Leu Arg Ser
1               5                   10                  15

<210> SEQ ID NO 272
<211> LENGTH: 17
<212> TYPE: PRT
<213> ORGANISM: Artificial Sequence
<220> FEATURE:
<223> OTHER INFORMATION: Synthetic

<400> SEQUENCE: 272

Tyr Ile Asn Pro Tyr Asn Asp Gly Thr Lys Tyr Ser Glu Lys Phe Lys
1               5                   10                  15

Gly

<210> SEQ ID NO 273
<211> LENGTH: 16
<212> TYPE: PRT
<213> ORGANISM: Artificial Sequence
<220> FEATURE:
<223> OTHER INFORMATION: Synthetic

<400> SEQUENCE: 273

Val Ile Trp Thr Gly Gly Asn Thr Asp Tyr Asn Pro Ala Leu Ile Pro
1               5                   10                  15

<210> SEQ ID NO 274
<211> LENGTH: 16
<212> TYPE: PRT
<213> ORGANISM: Artificial Sequence
<220> FEATURE:
<223> OTHER INFORMATION: Synthetic

<400> SEQUENCE: 274

Tyr Ile Ser Tyr Asp Gly Ser Asn Asn Tyr Asn Pro Ser Leu Lys Asn
1               5                   10                  15
```

<210> SEQ ID NO 275
<211> LENGTH: 16
<212> TYPE: PRT
<213> ORGANISM: Artificial Sequence
<220> FEATURE:
<223> OTHER INFORMATION: Synthetic

<400> SEQUENCE: 275

Val Ile Trp Ala Gly Gly Asn Thr Asn Tyr Asn Ser Ala Leu Met Ser
1               5                   10                  15

<210> SEQ ID NO 276
<211> LENGTH: 17
<212> TYPE: PRT
<213> ORGANISM: Artificial Sequence
<220> FEATURE:
<223> OTHER INFORMATION: Synthetic

<400> SEQUENCE: 276

Glu Ile Asn Pro Thr Asn Gly Arg Thr Tyr Tyr Asn Glu Lys Phe Lys
1               5                   10                  15

Arg

<210> SEQ ID NO 277
<211> LENGTH: 17
<212> TYPE: PRT
<213> ORGANISM: Artificial Sequence
<220> FEATURE:
<223> OTHER INFORMATION: Synthetic

<400> SEQUENCE: 277

Tyr Ile Asn Pro Asn Thr Ile Tyr Thr Asn Tyr Asn Gln Lys Phe Lys
1               5                   10                  15

Tyr

<210> SEQ ID NO 278
<211> LENGTH: 17
<212> TYPE: PRT
<213> ORGANISM: Artificial Sequence
<220> FEATURE:
<223> OTHER INFORMATION: Synthetic

<400> SEQUENCE: 278

Phe Ile Asn Pro Tyr Asn Asp Gly Thr Lys Tyr Asn Glu Gln Phe Lys
1               5                   10                  15

Gly

<210> SEQ ID NO 279
<211> LENGTH: 16
<212> TYPE: PRT
<213> ORGANISM: Artificial Sequence
<220> FEATURE:
<223> OTHER INFORMATION: Synthetic

<400> SEQUENCE: 279

Val Ile Trp Ala Gly Gly Ser Thr Asn Tyr Asp Ser Thr Leu Met Ser
1               5                   10                  15

<210> SEQ ID NO 280
<211> LENGTH: 17
<212> TYPE: PRT
<213> ORGANISM: Artificial Sequence
<220> FEATURE:
<223> OTHER INFORMATION: Synthetic

```
<400> SEQUENCE: 280

Tyr Ile Asn Pro Tyr Asn Asp Gly Thr Lys Tyr Ser Glu Arg Phe Lys
1               5                   10                  15
Gly

<210> SEQ ID NO 281
<211> LENGTH: 9
<212> TYPE: PRT
<213> ORGANISM: Artificial Sequence
<220> FEATURE:
<223> OTHER INFORMATION: Synthetic

<400> SEQUENCE: 281

Ile Tyr Tyr Gly Asn Ser Phe Ala Tyr
1               5

<210> SEQ ID NO 282
<211> LENGTH: 10
<212> TYPE: PRT
<213> ORGANISM: Artificial Sequence
<220> FEATURE:
<223> OTHER INFORMATION: Synthetic

<400> SEQUENCE: 282

Gln Gly Leu Tyr Gly His Ala Met Asp Tyr
1               5                   10

<210> SEQ ID NO 283
<211> LENGTH: 9
<212> TYPE: PRT
<213> ORGANISM: Artificial Sequence
<220> FEATURE:
<223> OTHER INFORMATION: Synthetic

<400> SEQUENCE: 283

Leu Ala Leu Gly Asn Ala Met Asp Tyr
1               5

<210> SEQ ID NO 284
<211> LENGTH: 12
<212> TYPE: PRT
<213> ORGANISM: Artificial Sequence
<220> FEATURE:
<223> OTHER INFORMATION: Synthetic

<400> SEQUENCE: 284

Gly Ala Tyr Tyr Gly Asn Ser Lys Ala Phe Asp Tyr
1               5                   10

<210> SEQ ID NO 285
<211> LENGTH: 11
<212> TYPE: PRT
<213> ORGANISM: Artificial Sequence
<220> FEATURE:
<223> OTHER INFORMATION: Synthetic

<400> SEQUENCE: 285

Glu Gly Tyr Gly Arg Gly Asn Ala Met Asp Tyr
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 286

Phe Gly Arg Gly Asn Thr Met Asp Tyr
1               5

<210> SEQ ID NO 287
<211> LENGTH: 9
<212> TYPE: PRT
<213> ORGANISM: Artificial Sequence
<220> FEATURE:
<223> OTHER INFORMATION: Synthetic

<400> SEQUENCE: 287

Leu Thr Arg Gly Asn Ser Phe Asp Tyr
1               5

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Leu Val Arg Gly Asn Ser Phe Asp Phe
1               5

<210> SEQ ID NO 289
<211> LENGTH: 11
<212> TYPE: PRT
<213> ORGANISM: Artificial Sequence
<220> FEATURE:
<223> OTHER INFORMATION: Synthetic

<400> SEQUENCE: 289

Arg Ala Tyr Gly Tyr Pro Tyr Ala Met Asp Tyr
1               5                   10

<210> SEQ ID NO 290
<211> LENGTH: 10
<212> TYPE: PRT
<213> ORGANISM: Artificial Sequence
<220> FEATURE:
<223> OTHER INFORMATION: Synthetic

<400> SEQUENCE: 290

Thr Arg Tyr Gly Gly Asn Ala Met Asp Tyr
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Synthetic

<400> SEQUENCE: 291

Ser Leu Tyr Gly Asn Ser Leu Asp Ser
1               5

<210> SEQ ID NO 292
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 292

Ser Leu Tyr Gly Asn Ser Phe Asp Tyr
1               5

<210> SEQ ID NO 293
<211> LENGTH: 10
<212> TYPE: PRT
<213> ORGANISM: Artificial Sequence
<220> FEATURE:
<223> OTHER INFORMATION: Synthetic

<400> SEQUENCE: 293

Asp Arg Tyr Gly Gly Asn Ser Leu Asp Tyr
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Synthetic

<400> SEQUENCE: 294

Ser Ser Tyr Tyr Gly Asn Ser Met Asp Tyr
1               5                   10

<210> SEQ ID NO 295
<211> LENGTH: 10
<212> TYPE: PRT
<213> ORGANISM: Artificial Sequence
<220> FEATURE:
<223> OTHER INFORMATION: Synthetic

<400> SEQUENCE: 295

His Lys Ala Tyr Gly Asn Ala Met Asp Tyr
1               5                   10

<210> SEQ ID NO 296
<211> LENGTH: 9
<212> TYPE: PRT
<213> ORGANISM: Artificial Sequence
<220> FEATURE:
<223> OTHER INFORMATION: Synthetic

<400> SEQUENCE: 296

Val Gly Arg Gly Asn Ala Met Asp His
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic

<400> SEQUENCE: 297

Leu Asp Tyr Gly Asn Ala Met Asp Tyr
1               5

<210> SEQ ID NO 298
<211> LENGTH: 10
<212> TYPE: PRT
<213> ORGANISM: Artificial Sequence
<220> FEATURE:
<223> OTHER INFORMATION: Synthetic

<400> SEQUENCE: 298
```

Asn Gly Tyr Tyr Gly Asn Ala Met Asp Tyr
1               5                   10

<210> SEQ ID NO 299
<211> LENGTH: 6
<212> TYPE: PRT
<213> ORGANISM: Artificial Sequence
<220> FEATURE:
<223> OTHER INFORMATION: Synthetic

<400> SEQUENCE: 299

Phe Arg Phe Phe Ala Tyr
1               5

<210> SEQ ID NO 300
<211> LENGTH: 11
<212> TYPE: PRT
<213> ORGANISM: Artificial Sequence
<220> FEATURE:
<223> OTHER INFORMATION: Synthetic

<400> SEQUENCE: 300

His Gly Tyr Gly Lys Gly Asn Ala Met Asp Asn
1               5                   10

<210> SEQ ID NO 301
<211> LENGTH: 9
<212> TYPE: PRT
<213> ORGANISM: Artificial Sequence
<220> FEATURE:
<223> OTHER INFORMATION: Synthetic

<400> SEQUENCE: 301

Ile Tyr Tyr Gly Asn Ser Met Asp Tyr
1               5

<210> SEQ ID NO 302
<211> LENGTH: 9
<212> TYPE: PRT
<213> ORGANISM: Artificial Sequence
<220> FEATURE:
<223> OTHER INFORMATION: Synthetic

<400> SEQUENCE: 302

Ser Leu Tyr Gly Asn Ser Phe Asp His
1               5

<210> SEQ ID NO 303
<211> LENGTH: 9
<212> TYPE: PRT
<213> ORGANISM: Artificial Sequence
<220> FEATURE:
<223> OTHER INFORMATION: Synthetic

<400> SEQUENCE: 303

Ala Tyr Phe Gly Asn Ser Phe Ala Tyr
1               5

<210> SEQ ID NO 304
<211> LENGTH: 17
<212> TYPE: PRT
<213> ORGANISM: Artificial Sequence
<220> FEATURE:
<223> OTHER INFORMATION: Synthetic

<400> SEQUENCE: 304

```
Lys Ser Ser Gln Ser Leu Leu Asn Ala Gly Asn Gln Lys Asn Tyr Leu
1               5                   10                  15

Thr

<210> SEQ ID NO 305
<211> LENGTH: 17
<212> TYPE: PRT
<213> ORGANISM: Artificial Sequence
<220> FEATURE:
<223> OTHER INFORMATION: Synthetic

<400> SEQUENCE: 305

Lys Ser Ser Gln Ser Leu Leu Glu Ser Gly Asn Gln Lys Asn Tyr Leu
1               5                   10                  15

Thr

<210> SEQ ID NO 306
<211> LENGTH: 17
<212> TYPE: PRT
<213> ORGANISM: Artificial Sequence
<220> FEATURE:
<223> OTHER INFORMATION: Synthetic

<400> SEQUENCE: 306

Phe Ile Asn Pro Tyr Asn Asp Asp Thr Lys Tyr Asn Glu Gln Phe Lys
1               5                   10                  15

Gly

<210> SEQ ID NO 307
<211> LENGTH: 9
<212> TYPE: PRT
<213> ORGANISM: Artificial Sequence
<220> FEATURE:
<223> OTHER INFORMATION: Synthetic

<400> SEQUENCE: 307

Ala Tyr Phe Gly Asn Ala Phe Ala Tyr
1               5

<210> SEQ ID NO 308
<211> LENGTH: 17
<212> TYPE: PRT
<213> ORGANISM: Artificial Sequence
<220> FEATURE:
<223> OTHER INFORMATION: Synthetic

<400> SEQUENCE: 308

Arg Ser Ser Gln Ser Leu Leu Glu Ser Gly Asn Arg Lys Asn Tyr Leu
1               5                   10                  15

Thr

<210> SEQ ID NO 309
<211> LENGTH: 17
<212> TYPE: PRT
<213> ORGANISM: Artificial Sequence
<220> FEATURE:
<223> OTHER INFORMATION: Synthetic

<400> SEQUENCE: 309

Arg Ser Ser Gln Ser Leu Leu Asn Ala Gly Asn Arg Lys Asn Tyr Leu
1               5                   10                  15

Thr
```

```
<210> SEQ ID NO 310
<211> LENGTH: 17
<212> TYPE: PRT
<213> ORGANISM: Artificial Sequence
<220> FEATURE:
<223> OTHER INFORMATION: Synthetic

<400> SEQUENCE: 310

Tyr Ile Thr Ser Gly Gln Ser Pro Ile Tyr Phe Thr Asp Thr Val Lys
1               5                   10                  15
Gly

<210> SEQ ID NO 311
<211> LENGTH: 17
<212> TYPE: PRT
<213> ORGANISM: Artificial Sequence
<220> FEATURE:
<223> OTHER INFORMATION: Synthetic

<400> SEQUENCE: 311

Tyr Ile Thr Ser Gly Glu Ser Pro Ile Tyr Phe Thr Asp Thr Val Lys
1               5                   10                  15
Gly

<210> SEQ ID NO 312
<211> LENGTH: 10
<212> TYPE: PRT
<213> ORGANISM: Artificial Sequence
<220> FEATURE:
<223> OTHER INFORMATION: Synthetic

<400> SEQUENCE: 312

Ser Ser Tyr Tyr Gly Gln Ser Met Asp Tyr
1               5                   10

<210> SEQ ID NO 313
<211> LENGTH: 10
<212> TYPE: PRT
<213> ORGANISM: Artificial Sequence
<220> FEATURE:
<223> OTHER INFORMATION: Synthetic

<400> SEQUENCE: 313

Ser Ser Tyr Tyr Gly Glu Ser Met Asp Tyr
1               5                   10

<210> SEQ ID NO 314
<211> LENGTH: 10
<212> TYPE: PRT
<213> ORGANISM: Artificial Sequence
<220> FEATURE:
<223> OTHER INFORMATION: Synthetic

<400> SEQUENCE: 314

Ser Ser Tyr Tyr Gly Asn Ala Met Asp Tyr
1               5                   10
```